United States Patent [19]

Rühter et al.

[11] Patent Number: 5,602,137
[45] Date of Patent: Feb. 11, 1997

[54] PYRIMIDINE COMPOUNDS AND THEIR USE AS PHARMACEUTICALS

[75] Inventors: Gerd Rühter; Theo Schotten, both of Hamburg; Wolfgang Stenzel, Reinbek; Michael Paal, Hamburg, all of Germany

[73] Assignee: Beiersdorf-Lilly GmbH, Hamburg, Germany

[21] Appl. No.: 451,799

[22] Filed: May 26, 1995

Related U.S. Application Data

[62] Division of Ser. No. 254,803, Jun. 6, 1994.

[30] Foreign Application Priority Data

Jun. 10, 1993 [EP] European Pat. Off. ............ 93304513

[51] Int. Cl.$^6$ ................. A61K 31/505; C07D 239/70
[52] U.S. Cl. ................ 514/258; 514/257; 514/81; 544/251; 544/244; 544/263
[58] Field of Search ................... 544/244, 263, 544/251; 514/81, 258, 257, 267

[56] References Cited

U.S. PATENT DOCUMENTS 5,358,950  10/1994  Bru-Magniez et al. .............. 514/258

FOREIGN PATENT DOCUMENTS

| 2078058 | 3/1993 | Canada . |
|---|---|---|
| 0323841 | 7/1989 | European Pat. Off. . |
| 0400974 | 12/1990 | European Pat. Off. . |
| 0412848 | 2/1991 | European Pat. Off. . |
| 0419048 | 3/1991 | European Pat. Off. . |
| 0490587 | 6/1992 | European Pat. Off. . |
| 0500136 | 8/1992 | European Pat. Off. . |
| 0502725 | 9/1992 | European Pat. Off. . |
| 0505111 | 9/1992 | European Pat. Off. . |
| 2448542 | 9/1980 | France . |
| 9318035 | 9/1993 | WIPO . |
| 9317023 | 9/1993 | WIPO . |
| 9317682 | 9/1993 | WIPO . |
| 9317681 | 9/1993 | WIPO . |
| 9317024 | 9/1993 | WIPO . |

OTHER PUBLICATIONS

Liebigs, *Annalen der Chemie:* 1966, Cover page & pp. 127–132.

*Primary Examiner*—Joseph McKane
*Assistant Examiner*—Richard S. Myers, Jr.
*Attorney, Agent, or Firm*—Sprung Horn Kramer & Woods

[57] ABSTRACT

Compounds for treating cardiovascular or circulatory disorders of the formula

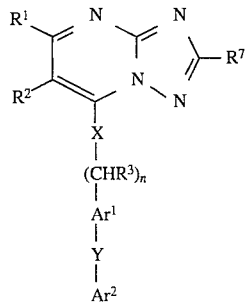

and pharmaceutically acceptable salts thereof wherein $R^1$, $R^2$, $R^3$, $R^7$, $Ar^1$, $Ar^2$, X, Y, and n are defined herein.

10 Claims, No Drawings

PYRIMIDINE COMPOUNDS AND THEIR USE AS PHARMACEUTICALS

This is a division of application Ser. No. 08/254,803, filed on Jun. 6, 1994, now allowed.

The invention relates to novel azolo-fused pyrimidine compounds and their use as pharmaceuticals.

The compounds of the invention are of the formula:

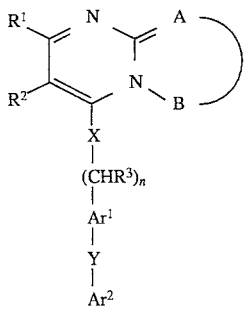

in which
$R^1$ is either $R^{1a}$ selected from
  a) hydrogen,
  b) $C_{1-8}$-alkyl, $C_{3-8}$-cycloalkyl, $C_{4-8}$-cycloalkylalkyl, or $C_{4-8}$-alkylcycloalkyl, which optionally may be substituted by one or more fluoro or chloro substituents, or by a single hydroxy, $C_{1-4}$-alkoxy, or $C_{1-4}$-alkylthio,
  c) phenyl or phenyl-$C_{1-3}$-alkyl, in which the phenyl group optionally may be substituted,
  d) $C_{2-8}$-alkenyl, $C_{3-8}$-cycloalkenyl, or $C_{2-8}$-alkynyl, which optionally may be substituted by phenyl, or
$R^{1b}$ selected from
  a) $C_{1-6}$-alkylthio, $C_{3-6}$-cycloalkylthio, $C_{1-6}$-alkoxy, $C_{3-6}$-cycloalkoxy, mono-$C_{1-6}$-alkylamino, or mono-$C_{3-6}$-cycloalkylamino, in which an alkyl group optionally may be substituted by phenyl or by one or more fluoro substituents,
  b) phenylthio or phenoxy, in which the phenyl group optionally may be substituted,
  c) di-$C_{1-4}$-alkylamino, in which the alkyl groups may be the same or different or together form a polymethylene ring with three, four, five, or six carbon atoms, which optionally may be interrupted by an oxygen atom and optionally may be substituted by one or more fluoro substituents,
  d) mono-phenylamino or mono-$C_{1-4}$-alkyl-monophenylamino, in which the phenyl group optionally may be substituted and the alkyl groups optionally may be substituted by one or more fluoro substituents, or
  e) halo,
$R^2$ is
  a) hydrogen,
  b) $C_{1-8}$-alkyl, which optionally may be substituted by one or more fluoro substituents,
  c) optionally substituted phenyl,
$R^1$ and $R^2$ together form a polymethylene chain containing three, four or five carbon atoms, which optionally may be interrupted by an oxygen or sulfur atom,
$R^3$ is hydrogen or $C_{1-4}$-alkyl, and n is 0 or 1,
X is O, S, or $NR^4$, and
$R^4$ is
  a) hydrogen,
  b) $C_{1-8}$-alkyl, $C_{3-8}$-cycloalkyl, $C_{4-8}$-cycloalkylalkyl, or $C_{4-8}$-alkylcycloalkyl, which optionally may be substituted by phenyl or by one or more fluoro substituents,
  c) optionally substituted phenyl,
  d) $(CH_2)_m COOR^{22}$,
  e) $(CH_2)_m CONR^{23} R^{24}$,
  f) $(CH_2)_m COOP^1$, in which $P^1$ is a carboxy-protecting group,
  g) $(CH_2)_m CN$,
  h) $(CH_2)_m$(5-tetrazolyl), and m is 1 or 2 in groups d), e), f), g) or h)
=A—B—together with the pyrimidine ring forms
  a) a pyrazolo[1,5-a]pyrimidine of formula (A),

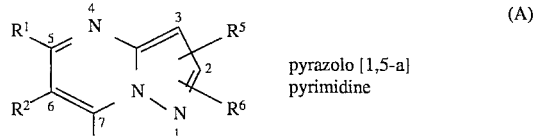

pyrazolo [1,5-a] pyrimidine b) a [1,2,4]triazolo[1,5-a]pyrimidine of formula (B),

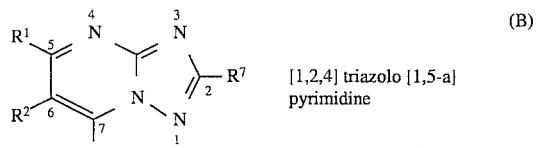

[1,2,4] triazolo [1,5-a] pyrimidine c) an imidazo[1,5-a]pyrimidine of formula (C),

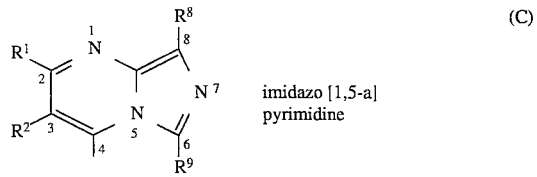

imidazo [1,5-a] pyrimidine or d) an imidazo[1,2-a]pyrimidine of formula (D),

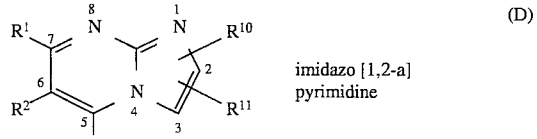

imidazo [1,2-a] pyrimidine in which
$R^5$ is
  a) hydrogen,
  b) $C_{1-8}$-alkyl, $C_{3-8}$-cycloalkyl, $C_{4-8}$-cycloalkylalkyl, or $C_{4-8}$-alkylcycloalkyl, which optionally may be substituted by one or more fluoro or chloro substituents,
  c) phenyl-$C_{1-3}$-alkyl,
  d) hydroxy, $C_{1-6}$-alkoxy, $C_{3-6}$-cycloalkoxy, $C_{1-3}$-phenylalkoxy, or phenoxy, in which the phenyl groups are optionally substituted and the alkyl and cycloalkyl groups optionally are substituted by one or more fluorine atoms,
  e) halo,
  f) mercapto,
  g) $C_{1-6}$-alkylthio, $C_{1-6}$-alkylsulfinyl, $C_{1-6}$-alkylsulfonyl, $C_{3-6}$-cycloalkylthio, $C_{3-6}$-cycloalkylsulfinyl, or $C_{3-6}$-cycloalkylsulfonyl, which optionally may be substituted by one or more fluorine atoms,
  h) phenylthio, phenylsulfinyl, phenylsulfonyl, phenyl-$C_{1-3}$-alkylthio, phenyl-$C_{1-3}$-alkylsulfinyl, or phenyl-$C_{1-3}$-sulfonyl, in which the phenyl groups optionally may be substituted,
  i) optionally substituted phenyl,
  j) cyano,
  k) $COOR^{22}$,
  l) $CONR^{23}R^{24}$,
  m) 5-tetrazolyl, n) COOP$^1$, in which P$^1$ is a carboxy-protecting group,
o) SO$_3$H,
p) SO$_2$NR$^{23}$R$^{24}$,
q) nitro or nitroso, with the proviso that these groups are not connected to C-2 of the heterocycle,
r) NR$^{23}$R$^{24}$,
s) C$_{1-6}$-alkanoyl or 1-hydroxy-C$_{1-6}$-alkyl, which optionally may be substituted by one or more fluorine atoms,
t) benzoyl or phenylhydroxymethyl, in which the phenyl group optionally may be substituted,
u) NH(C$_{1-6}$-alkanoyl) or NH(C$_{1-6}$-alkylsulfonyl), in which the alkyl groups optionally may be substituted by one or more fluorine atoms,
v) NH(benzoyl) or NH(benzenesulfonyl), in which the phenyl group optionally may be substituted, R$^6$ is
a) hydrogen,
b) C$_{1-8}$-alkyl, C$_{3-8}$-cycloalkyl, C$_{4-8}$-cycloalkylalkyl, or C$_{4-8}$-alkylcycloalkyl, which optionally may be substituted by one or more fluoro or chloro substituents,
c) halo,
d) optionally substituted phenyl,
e) C$_{1-6}$-alkylthio, C$_{1-6}$-alkylsulfinyl, C$_{1-6}$-alkylsulfonyl, C$_{3-6}$-cycloalkylthio, C$_{3-6}$-cycloalkylsulfinyl, or C$_{3-6}$-cycloalkylsulfonyl, which optionally may be substituted by one or more fluorine atoms, R$^5$ and R$^6$ together may form a polymethylene chain containing three, four, or five carbon atoms,
R$^7$ has the meaning as defined for R$^5$ with the exception of nitro and nitroso,
R$^8$ is
a) hydrogen,
b) C$_{1-8}$-alkyl, C$_{3-8}$-cycloalkyl, C$_{4-8}$-cycloalkylalkyl, or C$_{4-8}$-alkylcycloalkyl, which optionally may be substituted by one or more fluoro or chloro substituents,
c) halo,
d) optionally substituted phenyl,
e) nitro,
f) cyano,
g) 5-tetrazolyl,
h) COOR$^{22}$,
i) CONR$^{23}$R$^{24}$,
j) COOP$^1$, in which P$^1$ is a carboxy-protecting group,
k) NR$^{23}$R$^{24}$,
l) NH(C$_{1-6}$-alkanoyl) or NH(C$_{1-6}$-alkylsulfonyl), in which the alkyl groups optionally may be substituted by one or more fluorine atoms,
m) NH(benzoyl) or NH(benzenesulfonyl), in which the phenyl group optionally may be substituted, R$^9$ is
a) hydrogen,
b) C$_{1-8}$-alkyl, C$_{3-8}$-cycloalkyl, C$_{4-8}$-cycloalkylalkyl, or C$_{4-8}$-alkylcycloalkyl, which optionally may be substituted by one or more fluoro or chloro substituents,
c) an optionally substituted phenyl group,
d) cyano,
e) COOR$^{22}$,
f) CONR$^{23}$R$^{24}$,
g) 5-tetrazolyl,
h) COOP$^1$, in which P$^1$ is a carboxy-protecting group,
i) formyl,
j) hydroxymethyl, R$^{10}$ has independently the same meaning as R$^5$,
R$^{11}$ has independently the same meaning as R$^6$,
Ar$^1$ is a group selected from
a) 1,4-phenylene of formula (E),

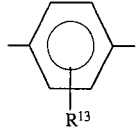

b) 1,4-substituted pyridine of formula (F) or formula (G),

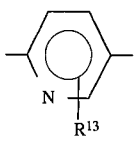

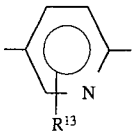

or c) benzofuran, benzothiophene, or indole of formula (H),

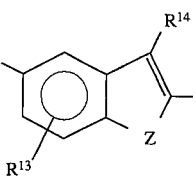

in which the group Z is O, S, or NR$^{12}$, and R$^{12}$ is hydrogen or C$_{1-4}$-alkyl,
and in each of the groups Ar$^1$ the substituent
R$^{13}$ is
a) hydrogen,
b) halo,
c) C$_{1-4}$-alkyl,
d) C$_{1-4}$-alkoxy,
e) trifluoromethyl,
f) nitro, R$^{14}$ is
a) hydrogen,
b) C$_{1-6}$-alkyl, C$_{3-6}$-cycloalkyl, C$_{4-6}$-cycloalkylalkyl, or C$_{4-6}$-alkylcycloalkyl, which optionally may be substituted by one or more fluoro or chloro substituents,
c) C$_{2-6}$-alkenyl or C$_{3-6}$-cycloalkenyl,
d) halo,
e) cyano,
f) nitro,
g) C$_{1-6}$-alkanoyl, in which the alkyl group optionally may be substituted by one or more fluorine atoms,
h) C$_{1-6}$-alkoxy,
i) COOR$^{22}$,
j) CONR$^{23}$R$^{24}$, Ar$^2$ is a group selected from a) phenyl of formula (I),

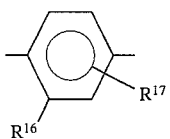

b) pyridine of formula (J),

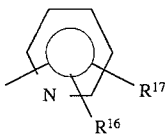

c) 1-pyrrolyl of formula (K),

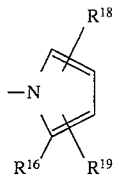

or d) a five-membered heterocycle of formula (L),

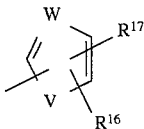

in which the group V is O, S, SO, $SO_2$, or $NR^{15}$, the group W is CH or N, and $R^{15}$ is hydrogen or $C_{1-4}$-alkyl, with the proviso that in groups $Ar^2$ of formula (J) and (L) the substituent $R^{16}$ and the group Y are in ortho positions, and in each of the groups $Ar^2$ the substituent $R^{16}$ is hydrogen, an acidic group, $COOP^1$, in which $P^1$ is a carboxy-protecting group, or a group selected from
a) cyano,
b) a protected 5-tetrazolyl of formula (M),

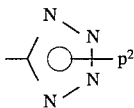

in which the group $P^2$ is a protecting group,
c) $COO(C_{1-4}$-alkyl),
d) nitro,
e) amino,
f) mercapto,
g) $SO_2Cl$,
h) $SO_2(OC_{1-4}$-alkyl),
i) $PO(OC_{1-4}$-alkyl)$_2$, $R^{17}$ has independently the same meaning as $R^{13}$, $R^{18}$ and $R^{19}$ are independently selected from
a) hydrogen,
b) $C_{1-6}$-alkyl, $C_{3-6}$-cycloalkyl, $C_{4-6}$-cycloalkylalkyl, or $C_{4-6}$-alkylcycloalkyl, which optionally may be substituted by one or more fluoro or chloro substituents,
c) $C_{2-6}$-alkenyl or $C_{3-6}$-cycloalkenyl,
d) halo,
e) nitro,
f) cyano,
g) $C_{1-4}$-alkylthio, Y is a group selected from a) C—C single bond, $CHR^{20}$, $CHR^{20}CH_2$, $OCHR^{20}$, $OCHR^{20}CH_2$, $SCHR^{20}$, $SCHR^{20}CH_2$, $NR^{21}CHR^{20}$, $NR^{21}CHR^{20}CH_2$, $CH_2CHR^{20}$, $CH_2CHR^{20}CH_2$,
b) O, S, $SO_2$, $NR^{21}$, CO, CONH, NHCO, $CH_2O$, $CH_2S$, $CH_2NR^{21}$, with the proviso that when Y is (b) $Ar^1$ is 1,4-phenylene of formula (E) and $Ar^2$ is phenyl of formula (I), $R^{20}$ is hydrogen or
a) COOH,
b) $COOP^1$, in which $P^1$ is a carboxy-protecting group,
c) $COO(C_{1-4}$-alkyl),
d) 5-tetrazolyl,
e) cyano,
f) a protected 5-tetrazolyl of formula (M), with the proviso that one of the substituents $R^{16}$ and $R^{20}$ is hydrogen and the other is a substituent other than hydrogen, $R^{21}$ and $R^{22}$ are independently selected from hydrogen or $C_{1-6}$-alkyl, and $R^{23}$ and $R^{24}$ are independently selected from hydrogen or $C_{1-4}$-alkyl, or together may form a polymethylene chain containing three, four or five carbon atoms, which optionally may be interrupted by an oxygen atom;

or a salt thereof.

Compounds of the above formula I, in which $R^{16}$ or $R^{20}$ is an acidic substituent or a group $COOP^1$, and pharmaceutical salts thereof, are useful as pharmaceuticals.

They are antagonists of angiotensin II receptors in mammals, and are indicated for use in the treatment and prophylaxis of, for example, hypertension, congestive heart failure, ocular hypertension, renal failure, and CNS disorders. Compounds of formula I in which $R^{16}$ or $R^{20}$ is other than an acidic substituent or $COOP^1$, that is, the remaining compounds of formula I, are intermediates in the synthesis of the pharmaceutically active compounds.

The renin-angiotensin system (RAS) is important in regulating blood pressure in mammals (M. J. Antonaccio, J. J. Wright, in "Cardiovascular Pharmacology", 3rd edition, Raven Press, New York, 1990, p. 201). Within this system the octapeptide angiotensin II is a potent vasoconstrictor producing hypertension by acting via receptors in the cardiovascular tissue. This hormone is produced from human angiotensinogen, which first is cleaved by the enzyme renin to angiotensin I and further degraded by the angiotensin converting enzyme (ACE). Inhibitors for both enzymes have been developed and clinically tested during the last few years (Ann. Rep. Med. Chem. 1991, 26, 63; J. Hypertension 1990, 8, S 149). ACE inhibitors, e.g. captopril or enalapril, have become important drugs for treating hypertension and congestive heart failure. However, their major reported side effect is dry cough (Br. Medical J. 1987, 294, 1521; J. Hypertension 1989, 7, S 308). Therefore, it was envisaged that the development of drugs blocking receptors of angiotensin II, which are divided into several subtypes, mainly into $AT_1$—and $AT_2$—receptors (the former are supposed to be responsible for its cardiovascular effects), might bring benefits. The first reported angiotensin II antagonists were peptides, namely saralasine, but these showed low receptor subtype selectivity, lack of oral activity and partial agonist properties. However, today many orally active, subtype specific angiotensin II antagonists are known.

In the above formula I, the term "$C_{1-8}$-alkyl" means a straight or branched saturated alkyl group and includes methyl, ethyl, n-propyl, isopropyl, n-butyl, sec-butyl, isobutyl, tert-butyl, n-pentyl, isopentyl, n-hexyl, n-heptyl, n-octyl.

The term "$C_{3-8}$-cycloalkyl" includes cyclopropyl, cyclobutyl, cyclopentyl, cyclohexyl.

The term "$C_{4-8}$-cycloalkylalkyl" means a straight or branched saturated alkyl group, which is substituted by a saturated cycloalkyl, and includes cyclopropylmethyl, cyclopentylmethyl, cyclohexylmethyl, 2-cyclohexylethyl.

The term "$C_{4-8}$-alkylcycloalkyl" means a saturated cycloalkyl group, which is substituted by a straight or branched saturated alkyl, and includes 1-methylcyclopropyl, 2-methylcyclopropyl, 1-methylcyclopentyl, 1-methylcyclohexyl, 4,4-dimethylcyclohexyl.

The term "phenyl-$C_{1-3}$-alkyl" means a straight or branched saturated alkyl, which is substituted by phenyl, and includes benzyl, 2-phenylethyl, 1-phenylethyl.

The term "$C_{2-8}$-alkenyl" means a straight or branched alkenyl group with at least one C=C double bond and includes 1-propenyl, 2-propenyl, 3-propenyl, 2-butene-1-yl, 1-butene-1-yl, 2-methyl-1-propenyl, 2-methyl-3-propenyl.

The term "$C_{3-8}$-cycloalkenyl" includes 1-cyclopentenyl, 2-cyclopentenyl, 1-cyclohexenyl, 2-cyclohexenyl.

The term "$C_{2-8}$-alkynyl" includes 1-propynyl, 3-propynyl, 1-butynyl, 2-butyne-1-yl, 1-hexynyl.

The term "$C_{1-6}$-alkoxy" includes methoxy, ethoxy, propyloxy, isopropyloxy, n-butyloxy, isobutyloxy, sec-butyloxy, tert-butyloxy, n-pentyloxy, iso-pentyloxy.

The term "$C_{3-6}$-cycloalkoxy" includes cyclopropyloxy, cyclobutyloxy, cyclopentyloxy, cyclohexyloxy.

The term "phenyl-$C_{1-3}$-alkoxy" means a $C_{1-3}$-alkoxy group, which is substituted by phenyl, and includes phenylmethoxy, 2-phenylethoxy, 1-phenylethoxy.

The term "$C_{1-6}$-alkanoyl" includes formyl, acetyl, propionyl, butyryl, 2-methylpropionyl, pentanoyl, 2-methylbutyryl, 3-methylbutyryl, pivaloyl.

The term "1-hydroxy-$C_{1-6}$-alkyl" means a $C_{1-6}$-alkyl group, which is substituted by hydroxy at C-1, and includes hydroxymethyl, 1-hydroxyethyl, 1-hydroxypropyl, 1-hydroxybutyl, 1-hydroxy-2-methylpropyl, 1-hydroxypentyl.

The term "phenylhydroxymethyl" means a methyl group, which is substituted by hydroxy and by phenyl.

The term "$C_{1-6}$-alkylthio" includes methylthio, ethylthio, propylthio, isopropylthio, n-butylthio.

The term "$C_{3-6}$-cycloalkylthio" includes cyclopentylthio, cyclohexylthio.

The term "phenyl-$C_{1-3}$-alkylthio" means a $C_{1-3}$-alkylthio group, which is substituted by phenyl, and includes phenylmethylthio.

The term "$C_{1-6}$-alkylsulfinyl" includes methylsulfinyl, ethylsulfinyl, propylsulfinyl, isopropylsulfinyl, n-butylsulfinyl.

The term "$C_{1-6}$-alkylsulfonyl" includes methylsulfonyl, ethylsulfonyl, propylsulfonyl, isopropylsulfonyl, n-butylsulfonyl.

The term "mono-$C_{1-4}$-alkylamino" means an amino group, which is substituted by one straight or branched alkyl, and includes methylamino, ethylamino, propylamino, isopropylamino, n-butylamino, sec-butylamino, isobutylamino, tert-butylamino.

The term "di-$C_{1-4}$-alkylamino" means an amino group, which is substituted by two straight or branched alkyl groups, which are the same or different, and includes dimethylamino, N-methyl-N-ethylamino, diethylamino, dipropylamino, diisopropylamino, N-methyl-N-butylamino, pyrrolidino, piperidino.

The term "mono-$C_{1-4}$-alkyl-monophenylamino" includes N-phenyl-N-methylamino, N-phenyl-N-ethylamino, N-phenyl-N-butylamino.

The term "halo" means fluoro, chloro, bromo, or iodo.

The term "optionally substituted phenyl" means a phenyl group, which is unsubstituted or may be preferably substituted by one or more halo such as fluoro, chloro, bromo or iodo, $C_{1-4}$-alkyl, $C_{1-4}$-alkoxy, $C_{1-4}$-alkylthio, $C_{1-4}$-alkylsulfinyl, $C_{1-4}$-alkylsulfonyl, cyano, nitro, trifluoromethyl, or hydroxy, and includes for example, phenyl, 2-methylphenyl, 3-methylphenyl, 4-methylphenyl, 2,4-dimethylphenyl, 4-ethylphenyl, 2-methoxyphenyl, 3-methoxyphenyl, 4-methoxyphenyl, 2,4-dimethoxyphenyl, 2-chlorophenyl, 3-chlorophenyl, 4-chlorophenyl, 2,4-dichlorophenyl, 3,5-dichlorophenyl, 4-fluorophenyl, pentafluorophenyl, 4-bromophenyl, 4-methylthiophenyl, 4-trifluoromethylphenyl, 4-cyanophenyl, 4-nitrophenyl, 4-hydroxyphenyl.

The term "optionally by one or more fluoro substituents substituted $C_{1-8}$-alkyl" includes the term "$C_{1-8}$-polyfluoroalkyl", which includes trifluoromethyl, pentafluoroethyl, heptafluoropropyl, nonafluoro-n-butyl.

The term "acidic group" means a group, which is capable forming an anion by donating a proton. Preferred acidic groups are those, which are known to those skilled in the art as bioisosteres of a carboxylic acid (A. Burger, Prog. Drug Res. 1991, 37, 287), and which give compounds of formula I having $pK_a$ values between one and eleven, preferred between two and eight, more preferred between four and seven. Examples of acidic groups include 5-tetrazolyl, carboxylic acid, sulfonic acid, phosphonic acid, or trifluoromethaneamide.

The term "carboxy-protecting group" means a group, which is commonly used for the protection of a carboxylic acid (T. W. Greene, P. G. M. Wuts, "Protective Groups in Organic Synthesis", 2nd Ed., p. 227 ff.). In particular, it means a protecting group $P^1$, which is readily cleaved in vivo. Therefore, compounds of formula I containing those protected carboxylic acids $COOP^1$ may be useful as prodrugs. Substituents $P^1$, which are useful for forming of a prodrug, are known ("Bioreversible Carriers in Drug Design: Theory and Application", E. B. Roche, Ed., Pergamon Press, 1987, p. 14 ff.). Preferred groups $COOP^1$ are alkylesters, in which the alkyl group $P^1$ is substituted by an activating group, which preferably is connected to the C-1 of the alkyl group.

Preferred $P^1$ groups include $C_{1-6}$-alkyl, which is substituted by halogen atoms, such as trifluoromethyl or 2,2,2-trichloroethyl;

$C_{1-6}$-alkyl, which is substituted by hydroxy groups, such as 2-hydroxyethyl or 2,3-dihydroxypropyl;

$C_{1-6}$-alkyl, which is substituted by an alkoxy or an alkoxyalkoxy group both containing between one and six carbon atoms, such as methoxymethyl, 2-methoxyethyl, or (2-methoxyethoxy)methyl;

phenacyl, in which the phenyl group optionally may be substituted, preferably the unsubstituted phenacyl group;

($C_{1-6}$-alkyl)OCO($C_{1-6}$-alkyl) or ($C_{3-6}$-cycloalkyl)O-CO($C_{1-6}$-alkyl) such as methoxycarbonylmethyl, ethoxycarbonylmethyl, isopropoxycarbonylmethyl, or cyclohexyloxycarbonylmethyl;

$C_{1-6}$-alkyl, which is substituted by $C_{1-6}$-alkylthio, $C_{1-6}$-alkylsulfonyl, or an optionally substituted phenylthio or phenylsulfonyl, such as (methylthio)methyl, (phenylthio)methyl, (methylsulfonyl)methyl, 2-(methylsulfonyl)ethyl, 2-(phenylsulfonyl)ethyl, or 2-(4-methylphenylsulfonyl)ethyl;

($C_{1-6}$-alkyl)COO($C_{1-6}$-alkyl) or ($C_{3-6}$-cycloalkyl) COO($C_{1-6}$-alkyl) such as acetoxymethyl, propionyloxymethyl, butyryloxymethyl, pivaloyloxymethyl, cyclopentanoyloxymethyl, cyclohexanoyloxymethyl, 1-(acetoxy)ethyl, 1-(propionyloxy)ethyl, 1-(butyryloxy)ethyl, 1-(pivaloyloxy)ethyl, 1-(cyclopentanoyloxy)ethyl, 1-(cyclohexanoyloxy)ethyl, 2-(acetoxy) ethyl, 2-(propionyloxy)ethyl, 2-(butyryloxy)ethyl, 2-(pivaloyloxy)ethyl, 2-(cyclopentanoyloxy)ethyl, 2-(cyclohexanoyloxy)ethyl, 1-(acetoxy)propyl, 1-(propionyloxy)propyl, 1-(butyryloxy)propyl, 1-(pivaloyloxy)propyl, 1-(cyclopentanoyloxy)propyl, 1-(cyclohexanoyloxy)propyl, 1-(acetoxy)butyl, 1-(propionyloxy)butyl, 1-(butyryloxy)butyl, 1-(pivaloyloxy)butyl, 1-(cyclopentanoyloxy)butyl, or 1-(cyclohexanoyloxy)butyl;

($C_{1-6}$-alkyl)OCOO($C_{1-6}$-alkyl) or ($C_{3-6}$-cycloalkyl)OCOO($C_{1-6}$-alkyl) such as methoxycarbonyloxymethyl, ethoxycarbonyloxymethyl, propoxycarbonyloxymethyl, isopropoxycarbonyloxymethyl, butoxycarbonyloxymethyl, pentoxycarbonyloxymethyl, cyclopentoxycarbonyloxymethyl, cyclohexyloxycarbonyloxymethyl, 1-(methoxycarbonyloxy)ethyl, 1-(ethoxycarbonyloxy)ethyl, 1-(propoxycarbonyloxy)ethyl, 1-(isopropoxycarbonyloxy) ethyl, 1-(butoxycarbonyloxy)ethyl, 1-(cyclohexyloxycarbonyloxy)ethyl, 2-(methoxycarbonyloxy)ethyl, 2-(ethoxycarbonyloxy)ethyl, 2-(propoxycarbonyloxy) ethyl, 2-(isopropoxycarbonyloxy) ethyl, 2-(butoxycarbonyloxy)ethyl, 2-(cyclohexyloxycarbonyloxy)ethyl, 1-(methoxycarbonyloxy)propyl, 1-(ethoxycarbonyloxy) propyl, 1-(propoxycarbonyloxy)propyl, 1-(isopropoxycarbonyloxy)propyl, 1-(butoxycarbonyloxy) propyl, 1-(cyclohexyloxycarbonyloxy)propyl, 1-(methoxycarbonyloxy)butyl, 1-(ethoxycarbonyloxy) butyl, 1-(propoxycarbonyloxy)butyl, 1-(isopropoxycarbonyloxy)butyl, 1-(butoxycarbonyloxy)butyl, or 1-(cyclohexyloxycarbonyloxy)butyl;

(5-($C_{1-6}$-alkyl)-2-oxo-1,3-dioxolene-4-yl)methyl or (5-phenyl-2-oxo-1,3-dioxolene-4-yl)methyl, in which the phenyl optionally may be substituted, such as (5-phenyl-2-oxo-1,3-dioxolene-4-yl)methyl, (5-(4-methoxyphenyl)-2-oxo-1,3-dioxolene-4-yl)methyl, (5-methyl-2-oxo-1,3-dioxolene-4-yl)methyl, (5-ethyl-2-oxo-1,3-dioxolene-4-yl)methyl, (5-propyl-2-oxo-1,3-dioxolene-4-yl)methyl, or (5-butyl-2-oxo-1,3-dioxolene-4-yl)methyl;

3-phthalidyl, in which the aromatic ring optionally may be substituted.

Particularly preferred $P^1$ groups include methoxymethyl, methoxycarbonylmethyl, ethoxycarbonylmethyl, acetoxymethyl, pivaloyloxymethyl, 1-(pivaloyloxy)ethyl, methoxycarbonyloxymethyl, ethoxycarbonyloxymethyl, 1-(methoxycarbonyloxy)ethyl, 1-(ethoxycarbonyloxy)ethyl, isopropoxycarbonyloxy methyl, 1-(isopropoxycarbonyloxy) ethyl, (5-methyl-2-oxo-1,3-dioxolene-4-yl)methyl, 3-phthalidyl, most particularly preferred pivaloyloxymethyl or ethoxycarbonyloxymethyl.

Protective $P^2$ groups for the protection of a tetrazole of formula (M) include triphenylmethyl, tert.-butyl, $C_{1-4}$-alkoxymethyl, methylthiomethyl, 4-nitrophenyl, tri($C_{1-4}$-alkyl)stannyl, triphenylstannyl, 2-(trimethylsilyl)ethyl, benzenesulfonyl, 4-methylbenzenesulfonyl, 2-cyanoethyl, benzyl, 4-methoxybenzyl, 2,4,6-trimethylbenzyl, 4-nitrobenzyl. Preferred protective groups $P^2$ are triphenylmethyl, trimethylstannyl, or tri(n-butyl)stannyl.

Preferred $R^1$ substituents are hydrogen, $C_{1-6}$-alkyl or $C_{3-6}$-cycloalkyl, which optionally may be substituted by one or more fluorine atoms, or $C_{1-5}$-alkylthio. Most preferred values of $R^1$ are methyl, ethyl, propyl, cyclopropyl, n-butyl, trifluoromethyl, pentafluoroethyl, 2,2,2-trifluoroethyl, methylthio, or ethylthio, and especially methyl or ethyl.

Preferred $R^2$ substituents are hydrogen or $C_{1-4}$-alkyl, and mostly preferred are hydrogen, methyl and ethyl, especially hydrogen.

Preferred $R^3$ substituents are hydrogen and methyl, and hydrogen is particularly preferred.

Preferred X groups are S or $NR^4$ and most preferred are S, NH, NMe, NEt, N(n-Pr), N(n-Bu), $NCH_2COOH$, $NCH_2COOMe$, $NCH_2COOEt$, $NCH_2CONH_2$, $NCH_2CONHMe$, $NCH_2CONMe_2$, $NCH_2CN$ and $NCH_2$(5-tetrazolyl). Particularly preferred are NH, NMe, $NCH_2COOH$, $NCH_2COOMe$, $NCH_2COOEt$ and $NCH_2CONH_2$, and especially NH and $NCH_2COOH$.

Preferred substitution patterns of the $R^5$ and $R^6$ substituents in the five-membered ring of pyrazolo[1,5-a]pyrimidines of formula (A) are 2,3-dihydrogen, 2-methyl, 2-ethyl, 2,3-dimethyl, 2-ethyl-3-methyl, 3-methyl, 3-ethyl, 3-propyl, 3-butyl, 3-trifluoromethyl, 3-nitro, 3-cyano, 3-methoxycarbonyl, 3-ethoxycarbonyl, 3-chloro, 3-bromo, 3-methylthio, 3-ethylthio, 3-methylsulfonyl, 3-ethylsulfonyl, 3-trifluoromethylsulfonyl, 3-chloro-2-methyl, 3-bromo-2-methyl, 2-methyl-3-nitro, 2-amino, 2-cyano, 2-methylthio, 2-hydroxymethyl, 2-hydroxycarbonyl, 2-methoxycarbonyl, 2-ethoxycarbonyl, 2-trifluoromethanesulfonylamino, mostly preferred 2,3-dihydrogen, 2-methyl, 3-methyl, 3-ethyl, 3-propyl, 3-cyano, 3-nitro, 3-chloro, 2-methylthio, particularly preferred both substituents are hydrogen.

Preferred $R^7$ substituents are hydrogen, methyl, ethyl, methylthio, dimethylamino, and especially hydrogen.

Preferred $R^8$ substituents are hydrogen, $C_{1-4}$-alkyl, halo, cyano, nitro, COOMe, or COOEt, and especially hydrogen, methyl, ethyl, propyl, cyano, chloro, bromo, or nitro, and particularly hydrogen.

Preferred $R^9$ substituents are hydrogen, methyl, cyano, COOMe, COOEt, $CONH_2$, (pivaloyloxymethoxy)carbonyl, 5-tetrazolyl, formyl, or hydroxymethyl, and especially hydrogen, cyano, hydroxymethyl, formyl, COOEt, or COOH, particularly hydrogen or COOH.

Preferred substitution patterns of the $R^{10}$ and $R^{11}$ substituents in the five-membered ring of imidazo[1,2-a]pyrimidines of formula (D) are 2,3-dihydrogen, 2-methyl, 2-ethyl, 2-methoxycarbonyl, 2-ethoxycarbonyl, 2-hydroxycarbonyl, 2-hydroxymethyl, 3-methoxycarbonyl, 3-ethoxycarbonyl, 3-hydroxycarbonyl, 3-hydroxymethyl, 3-formyl, 3-cyano, 3-nitro, 3-chloro, 3-bromo, 3-((pivaloyloxymethoxy)carbonyl), 3-(5-tetrazolyl), 3-aminocarbonyl, 3-$SO_3H$, 3-aminosulfonyl, 3-(trifluoromethanesulfonylamino), 3-methoxycarbonyl-2-methyl, 3-ethoxycarbonyl-2-methyl, 3-hydroxycarbonyl-2-methyl, 3-hydroxymethyl-2-methyl, 3-formyl-2-methyl, 2-methyl-3-nitro, 2-methyl-3-((pivaloyloxymethoxy)carbonyl), 2-methyl-3-(5-tetrazolyl), 3-aminocarbonyl-2-methyl, or 2-methyl-3-(trifluoromethanesulfonylamino), mostly preferred 2,3-dihydrogen, 2-methyl, 2-hydroxycarbonyl, 2-hydroxymethyl, 3-ethoxycarbonyl, 3-hydroxycarbonyl, 3-hydroxymethyl, 3-formyl, 3-$SO_3H$, 3-(trifluoromethanesulfonylamino), or 3-aminosulfonyl, particularly preferred 2,3-dihydrogen or 3-hydroxycarbonyl.

Preferred fused pyrimidines are pyrazolo[1,5-a]pyrimidine of formula (A), imidazo[1,5-a]pyrimidine of formula (C), or imidazo[1,2-a]pyrimidine of formula (D), and mostly preferable pyrazolo[1,5a]pyrimidine of formula (A).

Preferred $R^{12}$ and $R^{13}$ substituents are hydrogen or methyl, mostly preferable hydrogen Preferred $R^{14}$ substituents are hydrogen, $C_{1-3}$-alkyl, cyano, halo, trifluoromethyl, or $C_{1-3}$-alkoxy, most preferably methyl, ethyl, cyano, trifluoromethyl, chloro, bromo, or methoxy, and especially chloro, bromo, particularly bromo.

Preferred $Ar^1$ groups are 1,4-phenylene of formula (E), 1,4-substituted pyridine of formula (F) or (G), or benzothiophene or benzofuran of formula (H), most preferably an unsubstituted 1,4-phenylene of formula (E), an unsubstituted pyridine of formula (F) or (G), 3-chlorobenzofuran or 3-bromobenzofuran of formula (H), and especially 1,4-phenylene or 3-bromobenzofuran of formula (E) or (H), respectively.

Preferred $R^{15}$ substituents are hydrogen or methyl, most preferably hydrogen.

Preferred acidic substituents $R^{16}$ are COOH, (pivaloyloxymethoxy)carbonyl, 5-tetrazolyl, $NHSO_2CF_3$, $SO_3H$, or $PO(OH)_2$, and especially 5-tetrazolyl.

Preferred $R^{17}$ substituents are hydrogen, methyl, fluoro, chloro, or bromo, and especially preferred hydrogen.

Preferred $R^{18}$ and $R^{19}$ substituents are hydrogen, $C_{1-3}$-alkyl, halo, or cyano, most preferably hydrogen, methyl, fluoro, chloro, bromo, or trifluoromethyl, and hydrogen is particularly preferred. In preferred pyrroles of formula (K) the substituents $R^{18}$ or $R^{19}$ are 5-fluoro, 5-chloro, 5-bromo, 4-chloro, 4-bromo, 5-methyl, 5-trifluoromethyl, 3,5-dichloro, or 3,5-dibromo, most preferably 4-bromo, or 5-bromo. A particularly preferred value is that in which $R^{18}$ and $R^{19}$ are both hydrogen.

Preferred $Ar^2$ groups are a phenyl group of formula (I), most preferably one in which $R^{17}$ is hydrogen, a pyridine group of formula (J), most preferably one in which $R^{17}$ is hydrogen, a pyrrole of formula (K), most preferably one in which $R^{17}$ is hydrogen, or 5-halo, 5-methyl, 5-trifluoromethyl, 4-bromo, 4-chloro, 3,5-dichloro, or 3,5-dibromo, a furan of formula (L), most preferably furan-3-yl, which bears $R^{16}$ at C-4 and $R^{17}$ is hydrogen, or a thiophene of formula (L), mostly preferably 3-thienyl, which bears $R^{16}$ at C-2 or at C-4 and $R^{17}$ is hydrogen, or is 2-bromo or 2-methyl. Particularly preferred groups $Ar^2$ are those in which $R^{17}$ is hydrogen, and which are phenyl, pyrrol-1-yl, or 3-thienyl of formula (I), (K), or (L), respectively.

Preferred Y groups are C—C single bond, CH(5-tetrazolyl), CH(COOH), CH(5-tetrazolyl)CH$_2$, CH(COOH)CH$_2$, OCH(5-tetrazolyl), OCH(COOH), OCH(5-tetrazolyl)CH$_2$, OCH(COOH)CH$_2$, NHCH(5-tetrazolyl), NHCH(COOH), NHCH(5-tetrazolyl)CH$_2$, NHCH(COOH)CH$_2$, CH2CH(5-tetrazolyl), CH$_2$CH(COOH), O, CO, or NHCO, mostly preferable Y groups are C—C single bond, CH(5-tetrazolyl)CH$_2$, CH(COOH)CH$_2$, OCH(5-tetrazolyl), OCH(COOH), or O, especially C—C single bond.

Preferred $Ar^1$-Y-$Ar^2$ groups are 2'-(tetrazol-5-yl)biphenyl-4-yl, biphenyl-4-yl-2'-carboxylic acid, biphenyl-4-yl-2'-sulfonic acid, biphenyl-4-yl-2'-phosphonic acid, 2'-(trifluoromethanesulfonylamino)biphenyl-4-yl, 4-(3-(tetrazol-5-yl)pyridine-2-yl)phenyl, 4-(4-(tetrazol-5-yl)pyridine-3-yl)phenyl, 4-(3-(tetrazol-5-yl)pyridine-4-yl)phenyl, 4-(2-(tetrazol-5-yl)pyridine-3-yl)phenyl, 2-(2-(tetrazol-5-yl)phenyl)pyridine-5-yl, 5-(2-(tetrazol-5-yl)phenyl)pyridine-2-yl, 4-(2-(tetrazol-5-yl)phenoxy)phenyl, 4-(2-(tetrazol-5-yl)benzoyl)phenyl,4-(phthalamido)phenyl, 2-(N-(phenyl-4-yl)aminocarbonyl)benzenesulfonic acid, 4-(2-(tetrazol-5-yl)-3-thienyl)phenyl, 4-(4-tetrazol-5-yl)-3-thienyl)phenyl, 4-(2-bromo-4-(tetrazol-5-yl)-3-thienyl)phenyl, 4-(2-methyl-4-(tetrazol-5-yl)-3-thienyl)phenyl, 4-(4-tetrazol-5-yl)furan-3-yl)phenyl, 4-(2-(tetrazol-5-yl)pyrrol-1-yl)phenyl, 4-(5-bromo-2-(tetrazol-5-yl)pyrrol-1-yl)phenyl, 4-(5-chloro-2-(tetrazol-5-yl)pyrrol-1-yl)phenyl, 4-(5-methyl-2-(tetrazol-5-yl)pyrrol-1-yl)phenyl, 4-(5-fluoro-2-(tetrazol-5-yl)pyrrol-1-yl)phenyl, 4-(2-(tetrazol-5-yl)-5-trifluoromethylpyrrol-1-yl)phenyl, 4-(4-bromo-2-(tetrazol-5-yl)pyrrol-1-yl)phenyl, 4-(4-chloro-2-(tetrazol-5-yl)pyrrol-1-yl)phenyl, 4-(3,5-dichloro-2-(tetrazol-5-yl)pyrrol-1-yl)phenyl, 4-(3,5-dibromo-2-(tetrazol-5-yl)pyrrol-1-yl)phenyl, 3-bromo-2-(2-(tetrazol-5-yl)phenyl)benzofuran-5-yl, 3-chloro-2-(2-(tetrazol-5-yl)phenyl)benzofuran-5-yl, 3-methyl-2-(2-(tetrazol-5-yl)phenyl)benzofuran-5-yl, 3-bromo-2-(2-(tetrazol-5-yl)phenyl)benzothien-5-yl, α-(phenoxy-4-yl)benzeneacetic acid, 4-((phenyl)(tetrazol-5-yl)methoxy)phenyl, 2-(phenyl-4-yl)-3-phenylpropionic acid, 4-(2-phenyl-1-(tetrazol-5-yl)ethyl)phenyl, 4-(2-phenyl-2-(tetrazol-5-yl)ethyl)phenyl, 2-phenyl-3-(phenyl-4-yl)propionic acid, α-(N-(phenyl-4-yl)amino)benzeneacetic acid, or 4-(N-(phenyl)(tetrazol-5-yl)methyl)aminophenyl, mostly preferred 2'-(tetrazol-5-yl)biphenyl-4-yl, biphenyl-4-yl-2'-carboxylic acid, biphenyl-4-yl-2'-sulfonic acid, biphenyl-4-yl-2'-phosphonic acid, 2'-(trifluoromethanesulfonylamino)biphenyl-4-yl, 4-(3-(tetrazol-5-yl)pyridine-2-yl)phenyl, 4-(4-(tetrazol-5-yl)pyridine-3-yl))phenyl, 4-(3-(tetrazol-5-yl)pyridine-4-yl)phenyl, 4-(2-(tetrazol-5-yl)pyridine-3-yl)phenyl, 2-(2-(tetrazol-5-yl)phenyl)pyridine-5-yl, 5-(2-(tetrazol-5-yl)phenyl)pyridine-2-yl, 4-(2-(tetrazol-5-yl)-3-thienyl)phenyl, 4-(4-(tetrazol-5-yl)-3-thienyl)phenyl, 4-(2-(tetrazol-5-yl)pyrrol-1-yl)phenyl, or 3-bromo-2-(2-(tetrazol-5-yl)phenyl)benzofuran-5-yl, particularly preferred 2'-(tetrazol-5-yl)biphenyl-4-yl, 4-(2-(tetrazol-5-yl)pyrrol-1-yl)phenyl, or 3-bromo-2-(2-(tetrazol-5-yl)phenyl)benzofuran-5-yl, most particularly preferred 2'-(tetrazol-5-yl)biphenyl-4-yl.

It will be appreciated that the compounds of the invention can contain an asymmetric carbon atom which gives rise to enantiomers. The compounds are normally prepared as racemates and can conveniently be used as such, but individual enantiomers can be isolated by conventional techniques if so desired. Such racemates and individual enantiomers form part of the present invention.

It will also be understood that salts of the compounds of the invention can be prepared, and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example, pharmaceutically-acceptable salts, or are useful for identification, characterisation or purification.

Particularly preferred compounds of formula I of the present invention include:

1. 5-Methyl-7-[(2'-(tetrazol-5-yl)biphenyl-4-yl)methylamino]pyrazolo[1,5-a]pyrimidine
2. 5-Methyl-7-[N-methyl-N-((2'-(tetrazol-5-yl)biphenyl-4-yl)methyl)amino]pyrazolo[1,5-a]pyrimidine
3. 5-Ethyl-7-[(2'-(tetrazol-5-yl)biphenyl-4-yl)methylamino]pyrazolo[1,5-a]pyrimidine
4. 5-Ethyl-7-[N-methyl-N-((2'-(tetrazol-5-yl)biphenyl-4-yl)methyl)amino]pyrazolo[1,5-a]pyrimidine
5. 5-Propyl-7-[(2'-(tetrazol-5-yl)biphenyl-4-yl)methylamino]pyrazolo[1,5-a]pyrimidine
6. 7-[N-Methyl-N-((2'-(tetrazol-5-yl)biphenyl-4-yl)methyl)amino]-5-propylpyrazolo[1,5-a]pyrimidine
7. 5-Butyl-7-[(2'-(tetrazol-5-yl)biphenyl-4-yl)methylamino]pyrazolo[1,5-a]pyrimidine
8. 5-Butyl-7-[(N-methyl-N-((2'-(tetrazol-5-yl)biphenyl-4-yl)methyl)amino]pyrazolo[1,5-a]pyrimidine
9. 5-Cyclopropyl-7-[(2'-(tetrazol-5-yl)biphenyl-4-yl)methylamino]pyrazolo[1,5-a]pyrimidine
10. 5-Cyclopropyl-7-[(N-methyl-N-((2'-(tetrazol-5-yl)biphenyl-4-yl)methyl)amino]pyrazolo[1,5-a]pyrimidine
11. 5-Isopropyl-7-[(2'-(tetrazol-5-yl)biphenyl-4-yl)methylamino]pyrazolo[1,5-a]pyrimidine
12. 5-Isopropyl-7-[(N-methyl-N-((2'-(tetrazol-5-yl)biphenyl-4-yl)methyl)amino]pyrazolo[1,5-a]pyrimidine
13. 7-[(N-Ethyl-N-((2'-(tetrazol-5-yl)biphenyl-4-yl)methyl)amino]-5-methylpyrazolo[1,5-a]pyrimidine
14. 5-Methyl-7-[(N-propyl-N-((2'-(tetrazol-5-yl)biphenyl-4-yl)methyl)amino]pyrazolo[1,5-a]pyrimidine
15. 7-[(N-Butyl-N-((2'-(tetrazol-5-yl)biphenyl-4-yl)methyl)amino]-5-methylpyrazolo[1,5-a]pyrimidine
16. 5-Ethyl-7-[N-ethyl-N-((2'-(tetrazol-5-yl)biphenyl-4-yl)methyl)amino]pyrazolo[1,5-a]pyrimidine
17. 5-Ethyl-7-[N-propyl-N-((2'-(tetrazol-5-yl)biphenyl-4-yl)methyl)amino]pyrazolo[1,5-a]pyrimidine
18. 7-[N-Butyl-N-((2'-(tetrazol-5-yl)biphenyl-4-yl)methyl)amino]-5ethylpyrazolo[1,5-a]pyrimidine
19. 7-[(2'-(Tetrazol-5-yl)biphenyl-4-yl)methylamino]-5-trifluoromethylpyrazolo[1,5-a]pyrimidine
20. 7-[N-Methyl-N-((2'-(tetrazol-5-yl)biphenyl-4-yl)methyl) amino]-5-trifluoromethylpyrazolo[1,5-a]pyrimidine
21. 5-Methylthio-7-[(2'-(tetrazol-5-yl)biphenyl-4-yl)methylamino]pyrazolo[1,5-a]pyrimidine
22. 5-Ethylthio-7-[(2'-(tetrazol-5-yl)biphenyl-4-yl)methylamino]pyrazolo[1,5-a]pyrimidine
23. 5-Methyl-7-[(2'-(tetrazol-5-yl)biphenyl-4-yl)methoxy]pyrazolo[1,5a]pyrimidine
24. 5-Ethyl-7-[(2'-(tetrazol-5-yl)biphenyl-4-yl)methoxy]pyrazolo[1,5-a]pyrimidine
25. 5-Methyl-7-[(2'-(tetrazol-5-yl)biphenyl-4-yl)methylthio]pyrazolo[1,5-a]pyrimidine
26. 5-Ethyl-7-[(2'-(tetrazol-5-yl)biphenyl-4-yl)methylthio]pyrazolo[1,5-a]pyrimidine
27. 5-propyl-7-[(2'-(tetrazol-5-yl)biphenyl-4-yl)methylthio]pyrazolo[1,5-a]pyrimidine
28. 5-Butyl-7-[(2'-(tetrazol-5-yl)biphenyl-4-yl)methylthio]pyrazolo[1,5-a]pyrimidine
29. 5-Cyclopropyl-7-[(2'-(tetrazol-5-yl)biphenyl-4-yl)methylthio]pyrazolo[1,5-a]pyrimidine
30. 5-Isopropyl-7-[(2'-(tetrazol-5-yl)biphenyl-4-yl)methylthio]pyrazolo[1,5-a]pyrimidine
31. 7-[(2'-(Tetrazol-5-yl)biphenyl-4-yl)methylthio]-5-trifluoromethylpyrazolo[1,5-a]pyrimidine
32. 5-Methyl-7-[(2'-(tetrazol-5-yl)biphenyl-4-yl)amino]pyrazolo[1,5-a]pyrimidine
33. 5-Ethyl-7-[(2'-(tetrazol-5-yl)biphenyl-4-yl)amino]pyrazolo[1,5a]pyrimidine
34. 5-Cyclopropyl-7-[(2'-(tetrazol-5-yl)biphenyl-4-yl)amino]pyrazolo[1,5-a]pyrimidine
35. 7-[(2'-(Tetrazol-5-yl)biphenyl-4-yl)amino]-5-trifluoromethylpyrazolo[1,5-a]pyrimidine
36. 5-Ethyl-7-[N-methyl-N-(2'-(tetrazol-5-yl)biphenyl-4-yl)amino]pyrazolo [1,5-a]pyrimidine
37. 4'-[(5-Methylpyrazolo[1,5-a]pyrimidine-7-yl)amino]biphenyl-2-carboxylic acid
38. 4'-[(5-Ethylpyrazolo[1,5-a]pyrimidine-7-yl)amino]biphenyl-2-carboxylic acid
39. 4'-[(5-Methylpyrazolo[1,5-a]pyrimidine-7-yl)amino]biphenyl-2-sulfonic acid
40. 4'-[(5-Ethylpyrazolo[1,5-a]pyrimidine-7-yl)amino]biphenyl-2-sulfonic acid
41. 4'-[(5-Methylpyrazolo[1,5-a]pyrimidine-7-yl)amino]biphenyl-2-phosphonic acid
42. 4'-[(5-Ethylpyrazolo[1,5-a]pyrimidine-7-yl)amino]biphenyl-2-phosphonic acid
43. 5-Ethyl-7-[(2'-(trifluoromethanesulfonamido)biphenyl-4-yl)amino]pyrazolo[1,5-a]pyrimidine
44. 5-Methyl-7-[(2'-(tetrazol-5-yl)biphenyl-4-yl)methylamino]-1,2,4]triazolo[1,5-a]pyrimidine
45. 5-Ethyl-7-[(2'-(tetrazol-5-yl)biphenyl-4-yl)methylamino]-1,2,4]triazolo[1,5-a]pyrimidine
46. 5-Ethyl-7-[N-methyl-N-((2'-(tetrazol-5-yl)biphenyl-4-yl)methyl)amino]-1,2,4]triazolo[1,5-a]pyrimidine
47. 5-Ethyl-2-methyl-7-[(2'-(tetrazol-5-yl)biphenyl-4-yl)methylamino]-1,2,4]triazolo [1,5-a]pyrimidine
48. 2,5-Diethyl-7-[(2'-(tetrazol-5-yl)biphenyl-4-yl)methylamino]-1,2,4]triazolo[1,5-a]pyrimidine
49. 5-Ethyl-2-methylthio-7-[(2'-(tetrazol-5-yl)biphenyl-4-yl)methylamino]-1,2,4]triazolo [1,5-a]pyrimidine
50. 2-Amino-5-ethyl-7-[(2'-(tetrazol-5-yl)biphenyl-4-yl)methylamino]-1,2,4]triazolo[1,5-a]pyrimidine
51. 5-Ethyl-7-[(2'-(tetrazol-5-yl)biphenyl-4-yl)methylamino]-2-trifluoromethanesulfonamido-[1,2,4]triazolo [1,5-a]pyrimidine
52. 3-Chloro-5-methyl-7-[(2'-(tetrazol-5-yl)biphenyl-4-yl)methylamino]pyrazolo[1,5-a]pyrimidine
53. 3-Chloro-5-ethyl-7-[(2'-(tetrazol-5-yl)biphenyl-4-yl)methylamino]pyrazolo[1,5-a]pyrimidine
54. 3-Chloro-7-[(2'-(tetrazol-5-yl)biphenyl-4-yl)methylamino]-5-trifluoromethylpyrazolo[1,5-a]pyrimidine
55. 3-Bromo-5-methyl-7-[(2'-(tetrazol-5-yl)biphenyl-4-yl)methylamino]pyrazolo[1,5-a]pyrimidine
56. 3-Bromo-5-ethyl-7-[(2'-(tetrazol-5-yl)biphenyl-4-yl)methylamino]pyrazolo[1,5-a]pyrimidine
57. 5-Methyl-3-nitro-7-[(2'-(tetrazol-5-yl)biphenyl-4-yl)methylamino]pyrazolo[1,5-a]pyrimidine
58. 5-Ethyl-3-nitro-7-[(2'-(tetrazol-5-yl)biphenyl-4-yl)methylamino]pyrazolo[1,5-a]pyrimidine
59. 3-Cyano-5-methyl-7-[(2'-(tetrazol-5-yl)biphenyl-4-yl)methylamino]pyrazolo[1,5-a]pyrimidine
60. 3-Cyano-5-ethyl-7-[(2'-(tetrazol-5-yl)biphenyl-4-yl)methylamino]pyrazolo[1,5-a]pyrimidine
61. 3,5-Dimethyl-7-[(2'-(tetrazol-5-yl)biphenyl-4-yl)methylamino]pyrazolo[1,5-a]pyrimidine
62. 3-Methyl-5-ethyl-7-[(2'-(tetrazol-5-yl)biphenyl-4-yl)methylamino]pyrazolo[1,5-a]pyrimidine
63. 5-Methyl-3-ethyl-7-[(2'-(tetrazol-5-yl)biphenyl-4-yl)methylamino]pyrazolo[1,5-a]pyrimidine
64. 3,5-Diethyl-7-[(2'-(tetrazol-5-yl)biphenyl-4-yl)methylamino]pyrazolo[1,5-a]pyrimidine
65. 5-Methyl-3-propyl-7-[(2'-(tetrazol-5-yl)biphenyl-4-yl)methylamino]pyrazolo[1,5-a]pyrimidine
66. 5-Ethyl-3-propyl-7-[(2'-(tetrazol-5-yl)biphenyl-4-yl)methylamino]pyrazolo[1,5-a]pyrimidine 67. 5-Ethyl-7-[(2'-(tetrazol-5-yl)biphenyl-4-yl)methylamino]-3-trifluoromethylpyrazolo[1,5-a]pyrimidine
68. 2-Methylthio-5-ethyl-7-[(2'-(tetrazol-5-yl)biphenyl-4-yl)methylamino]pyrazolo[1,5-a]pyrimidine
69. 2-Methyl-5-ethyl-7-[(2'-(tetrazol-5-yl)biphenyl-4-yl)methylamino]pyrazolo[1,5-a]pyrimidine
70. 5-Ethyl-7-[(2'-(tetrazol-5-yl)biphenyl-4-yl)methylamino]-2-trifluoromethanesulfonamidopyrazolo[1,5-a]pyrimidine
71. 5-Ethyl-5-methylsulfonyl-7-[(2'-(tetrazol-5-yl)biphenyl-4-yl)methylamino]pyrazolo[1,5-a]pyrimidine
72. 2-Cyano-5-ethyl-7-[(2'-(tetrazol-5-yl)biphenyl-4-yl)methylamino]pyrazolo[1,5-a]pyrimidine
73. 5-Ethyl-7-[(2'-(tetrazol-5-yl)biphenyl-4-yl)methylamino]pyrazolo[1,5-a]pyrimidine-2-carboxylic acid
74. 2,3-Dimethyl-5-ethyl-7-[(2'-(tetrazol-5-yl)biphenyl-4-yl)methylamino]pyrazolo[1,5-a]pyrimidine
75. 2,5-Diethyl-3-methyl-7-[(2'-(tetrazol-5-yl)biphenyl-4-yl)methylamino]pyrazolo[1,5-a]pyrimidine
76. 2-Aminocarbonyl-5-ethyl-7-[(2'-(tetrazol-5-yl)biphenyl-4-yl)methylamino]pyrazolo[1,5-a]pyrimidine
77. 2-Aminosulfonyl-5-ethyl-7-[(2'-(tetrazol-5-yl)biphenyl-4-yl)methylamino]pyrazolo[1,5-a]pyrimidine
78. 5-Ethyl-7-[(2'-(tetrazol-5-yl)biphenyl-4-yl)methylamino]-3-(trifluoromethylsulfonyl)pyrazolo[1,5-a]pyrimidine
79. 2-Amino-5-ethyl-7-[(2'-(tetrazol-5-yl)biphenyl-4-yl)methylamino]pyrazolo[1,5-a]pyrimidine
80. 3,5-Dimethyl-7-[N-methyl-N-((2'-(tetrazol-5-yl)biphenyl-4-yl)methyl)amino]pyrazolo[1,5-a]pyrimidine
81. 5-Ethyl-3-methyl-7-[N-methyl-N-((2'-(tetrazol-5-yl)biphenyl-4-yl)methyl)amino]pyrazolo[1,5-a]pyrimidine
82. 3,5-Diethyl-7-[N-methyl-N-((2'-(tetrazol-5-yl)biphenyl-4-yl)methyl)amino]pyrazolo[1,5-a]pyrimidine
83. 3-Cyano-5-methyl-7-[N-methyl-N-((2'-(tetrazol-5-yl)biphenyl-4-yl)methyl)amino]pyrazolo[1,5-a]pyrimidine
84. 3-Cyano-5-ethyl-7-[N-methyl-N-((2'-(tetrazol-5-yl)biphenyl-4-yl)methyl)amino]pyrazolo[1,5-a]pyrimidine
85. 5-Methyl-3-nitro-7-[N-methyl-N-((2'-(tetrazol-5-yl)biphenyl-4-yl)methyl)amino]pyrazolo[1,5-a]pyrimidine
86. 5-Ethyl-3-nitro-7-[N-methyl-N-((2'-(tetrazol-5-yl)biphenyl-4-yl)methyl)amino]pyrazolo[1,5-a]pyrimidine
87. 3-Chloro-5-ethyl-7-[N-methyl-N-((2'-(tetrazol-5-yl)biphenyl-4-yl)methyl)amino]pyrazolo[1,5-a]pyrimidine
88. 3-Bromo-5-ethyl-7-[N-methyl-N-((2'-(tetrazol-5-yl)biphenyl-4-yl)methyl)amino]pyrazolo[1,5-a]pyrimidine
89. 4'-[N-((5-Methylpyrazolo[1,5-a]pyrimidine-7-yl)methyl)amino]biphenyl-2-carboxylic acid
90. 4'-[N-((5-Ethylpyrazolo[1,5-a]pyrimidine-7-yl)methyl)amino]biphenyl-2-carboxylic acid
91. 4'-[N-((5-Methylpyrazolo[1,5-a]pyrimidine-7-yl)methyl)amino]biphenyl-2-sulfonic acid
92. 4'-[N-((5-Ethylpyrazolo[1,5-a]pyrimidine-7-yl)methyl)amino]biphenyl-2-sulfonic acid
93. 4'-[N-((5-Ethylpyrazolo[1,5-a]pyrimidine-7-yl)methyl)amino]biphenyl-2-phosphonic acid
94. 5-Ethyl-7-[(2'-(trifluoromethanesulfonylamido)biphenyl-4-yl)methylamino]pyrazolo[1,5-a]pyrimidine
95. Pivaloyloxymethyl 4'-[N-((5-Ethylpyrazolo[1,5-a]pyrimidine-7-yl)methyl)amino]biphenyl-2-carboxylate
96. 5-Ethyl-7-[((4-phthalamido)phenyl)amino]pyrazolo[1,5-a]pyrimidine
97. 2-[(N-(4-(5-Ethylpyrazolo[1,5-a]pyrimidine-7-yl)amino)phenyl)aminocarbonyl]benzene sulfonic acid
98. 2-Methyl-4-[(2'-(tetrazol-5-yl)biphenyl-4-yl)methylamino]imidazo[1,5-a]pyrimidine
99. 2-Ethyl-4-[(2'-(tetrazol-5-yl)biphenyl-4-yl)methylamino]imidazo[1,5-a]pyrimidine
100. 2-Ethyl-4-[(2'-(tetrazol-5-yl)biphenyl-4-yl)methylamino]imidazo[1,5-a]pyrimidine-6-carboxylic acid
101. 2-Methyl-4-[(2'-(tetrazol-5-yl)biphenyl-4-yl)methylamino]imidazo[1,5-a]pyrimidine-6-carboxylic acid
102. 2-Ethyl-8-methyl-4-[(2'-(tetrazol-5-yl)biphenyl-4-yl)methylamino]imidazo[1,5-a]pyrimidine-6-carboxylic acid
103. 6-Aminocarbonyl-2-ethyl-4-[(2'-(tetrazol-5-yl)biphenyl-4-yl)methylamino]imidazo[1,5-a]pyrimidine
104. 2-Ethyl-8-nitro-4-[(2'-(tetrazol-5-yl)biphenyl-4-yl)methylamino]imidazo[1,5-a]pyrimidine
105. 8-Cyano-2-ethyl-4-[(2'-(tetrazol-5-yl)biphenyl-4-yl)methylamino]imidazo[1,5-a]pyrimidine
106. 2-Ethyl-8-methyl-4-[(2'-(tetrazol-5-yl)biphenyl-4-yl)methylamino]imidazo[1,5-a]pyrimidine
107. 2,8-Diethyl-4-[(2'-(tetrazol-5-yl)biphenyl-4-yl)methylamino]imidazo[1,5-a]pyrimidine
108. 7-Methyl-5-[(2'-(tetrazol-5-yl)biphenyl-4-yl)methylamino]imidazo[1,2-a]pyrimidine-2-carboxylic acid
109. 7-Ethyl-5-[(2'-(tetrazol-5-yl)biphenyl-4-yl)methylamino]imidazo[1,2-a]pyrimidine-2-carboxylic acid
110. 7-Methyl-5-[(2'-(tetrazol-5-yl)biphenyl-4-yl)methylamino]imidazo[1,2-a]pyrimidine-3-carboxylic acid
111. 7-Ethyl-5-[(2'-(tetrazol-5-yl)biphenyl-4-yl)methylamino]imidazo[1,2-a]pyrimidine-3-carboxylic acid
112. 7-Ethyl-3-formyl-5-[(2'-(tetrazol-5-yl)biphenyl-4-yl)methylamino]imidazo[1,2-a]pyrimidine
113. 7-Ethyl-3-hydroxymethyl-5-[(2'-(tetrazol-5-yl)biphenyl-4-yl)methylamino]imidazo[1,2-a]pyrimidine
114. 3-Cyano-7-ethyl-5-[(2'-(tetrazol-5-yl)biphenyl-4-yl)methylamino]imidazo[1,2-a]pyrimidine
115. 3-Aminocarbonyl-7-ethyl-5-[(2'-(tetrazol-5-yl)biphenyl-4-yl)methylamino]imidazo[1,2-a]pyrimidine
116. Methyl 7-Ethyl-5-[(2'-(tetrazol-5-yl)biphenyl-4-yl)methylamino]imidazo[1,2-a]pyrimidine-3-carboxylate
117. Ethyl 7-Ethyl-5-[(2'-(tetrazol-5-yl)biphenyl-4-yl)methylamino]imidazo[1,2-a]pyrimidine-3-carboxylate
118. 5-Methyl-7-[(5-(2-(tetrazol-5-yl)phenyl)pyridine-2-yl)methylamino]pyrazolo[1,5-a]pyrimidine
119. 5-Ethyl-7-[(5-(2-(tetrazol-5-yl)phenyl)pyridine-2-yl)methylamino]pyrazolo[1,5-a]pyrimidine
120. 5-Methyl-7-[(2-(2-(tetrazol-5-yl)phenyl)pyridine-5-yl)methylamino]pyrazolo[1,5-a]pyrimidine
121. 5-Ethyl-7-[(2-(2-(tetrazol-5-yl)phenyl)pyridine-5-yl)methylamino]pyrazolo[1,5-a]pyrimidine
122. 5-Methyl-7-[(4-(2-(tetrazol-5-yl)pyridine-3-yl)phenyl)methylamino]pyrazolo[1,5-a]pyrimidine
123. 5-Ethyl-7-[(4-(2-(tetrazol-5-yl)pyridine-3-yl)phenyl)methylamino]pyrazolo[1,5-a]pyrimidine
124. 5-Methyl-7-[(4-(3-(tetrazol-5-yl)pyridine-4-yl)phenyl)methylamino]pyrazolo[1,5-a]pyrimidine
125. 5-Ethyl-7-[(4-(3-(tetrazol-5-yl)pyridine-4-yl)phenyl)methylamino]pyrazolo[1,5-a]pyrimidine
126. 5-Methyl-7-[(4-(4-(tetrazol-5-yl)pyridine-3-yl)phenyl)methylamino]pyrazolo[1,5-a]pyrimidine
127. 5-Ethyl-7-[(4-(4-(tetrazol-5-yl)pyridine-3-yl)phenyl)methylamino]pyrazolo[1,5-a]pyrimidine
128. 5-Methyl-7-[(4-(3-(tetrazol-5-yl)pyridine-2-yl)phenyl)methylamino]pyrazolo[1,5-a]pyrimidine
129. 5-Ethyl-7-[(4-(3-(tetrazol-5-yl)pyridine-2-yl)phenyl)methylamino]pyrazolo[1,5-a]pyrimidine
130. 5-Methyl-7-[(4-(2-(tetrazol-5-yl)phenoxy)phenyl)methylamino]pyrazolo[1,5-a]pyrimidine
131. 5-Ethyl-7-[(4-(2-(tetrazol-5-yl)phenoxy)phenyl)methylamino]pyrazolo[1,5-a]pyrimidine 132. 5-Methyl-7-[(4-(2-(tetrazol-5-yl)benzoyl)phenyl)methylamino]pyrazolo[1,5-a]pyrimidine
133. 5-Ethyl-7-[(4-(2-(tetrazol-5-yl)benzoyl)phenyl)methylamino]pyrazolo[1,5a]pyrimidine
134. 5-Methyl-7-[(4-(2-(tetrazol-5-yl)-3-thienyl)phenyl)methylamino]pyrazolo[1,5-a]pyrimidine
135. 5-Ethyl-7-[(4-(2-(tetrazol-5-yl)-3-thienyl)phenyl)methylamino]pyrazolo[1,5-a]pyrimidine
136. 5-Methyl-7-[(4-(4-(tetrazol-5-yl)-3-thienyl)phenyl)methylamino]pyrazolo[1,5-a]pyrimidine
137. 5-Ethyl-7-[(4-(4-(tetrazol-5-yl)-3-thienyl)phenyl)methylamino]pyrazolo[1,5-a]pyrimidine
138. 5-Methyl-7-[(4-(4-(tetrazol-5-yl)furan-3-yl)phenyl)methylamino]pyrazolo[1,5-a]pyrimidine
139. 5-Ethyl-7-[(4-(4-(tetrazol-5-yl)furan-3-yl)phenyl)methylamino]pyrazolo[1,5-a]pyrimidine
140. 5-Ethyl-7-[(4-(2-methyl-4-(tetrazol-5-yl)-3-thienyl)phenyl)methylamino]pyrazolo[1,5-a]pyrimidine
141. 7-[(4-(2-Bromo-4-(tetrazol-5-yl)-3-thienyl)phenyl)methylamino]-5-ethylpyrazolo[1,5-a]pyrimidine
142. α-[4-(N-(5-Methylpyrazolo[1,5-a]pyrimidine-7-yl)methylamino)phenoxy]benzeneacetic acid
143. α-[4-(N-(5-Ethylpyrazolo[1,5-a]pyrimidine-7-yl)methylamino)phenoxy]benzeneacetic acid
144. 5-Methyl-7-[(4-((phenyl)(tetrazol-5-yl)methoxy)phenyl)methylamino]pyrazolo[1,5-a]pyrimidine
145. 5-Ethyl-7-[(4-((phenyl)(tetrazol-5-yl)methoxy)phenyl)methylamino]pyrazolo[1,5-a]pyrimidine
146. 5-Methyl-7-[(4-(N-((phenyl)(tetrazol-5-yl)methyl)amino)phenyl)methylamino]pyrazolo[1,5-a]pyrimidine
147. 5-Ethyl-7-[(4-(N-((phenyl)(tetrazol-5-yl)methyl)amino)phenyl)methylamino]pyrazolo[1,5-a]pyrimidine
148. 5-Methyl-7-[(4-(2-(phenyl)-2-(tetrazol-5-yl)ethyl)phenyl)methylamino]pyrazolo[1,5-a]pyrimidine
149. 5-Ethyl-7-[(4-(2-(phenyl)-2-(tetrazol-5-yl)ethyl)phenyl)methylamino]pyrazolo[1,5-a]pyrimidine
150. 3-[4-(N-(5-Ethylpyrazolo[1,5-a]pyrimidine-7-yl)methylamino)phenyl]-2-phenylpropionic acid
151. α-Amino-N-[4-(N'-(5-Ethylpyrazolo[1,5-a]pyrimidine-7-yl)methylamino)phenyl]benzeneacetic acid
152. 2-[4-(N-(5-Methylpyrazolo[1,5-a]pyrimidine-7-yl)methylamino)phenyl]-3-phenylpropionic acid
153. 2-[4-(N-(5-Ethylpyrazolo[1,5-a]pyrimidine-7-yl)methylamino)phenyl]-3-phenylpropionic acid
154. 5-Methyl-7-[(4-(2-(phenyl)-1-(tetrazol-5-yl)ethyl)phenyl)methylamino]pyrazolo[1,5-a]pyrimidine
155. 5-Ethyl-7-[(4-(2-(phenyl)-1-(tetrazol-5-yl)ethyl)phenyl)methylamino]pyrazolo[1,5-a]pyrimidine
156. α-[4-(N-(5-Ethylpyrazolo[1,5-a]pyrimidine-7-yl)amino)phenoxy]benzeneacetic acid
157. 5-Ethyl-7-[N-(4-((phenyl)(tetrazol-5-yl)methoxy)phenyl)amino]pyrazolo[1,5-a]pyrimidine
158. 2-[4-(N-(5-Ethylpyrazolo[1,5-a]pyrimidine-7-yl)amino)phenoxy]-3-phenylpropionic acid
159. 5-Ethyl-7-[N-(4-(2-(phenyl)-1-(tetrazol-5-yl)ethoxy)phenyl)amino]pyrazolo[1,5-a]pyrimidine
160. 5-Methyl-7-[(4-(2-(tetrazol-5-yl)pyrrol-1-yl)phenyl)methylamino]pyrazolo[1,5-a]pyrimidine
161. 5-Ethyl-7-[(4-(2-(tetrazol-5-yl)pyrrol-1-yl)phenyl)methylamino]pyrazolo[1,5-a]pyrimidine
162. 7-[(4-(5-Bromo-2-(tetrazol-5-yl)pyrrol-1-yl)phenyl)methylamino]-5-methylpyrazolo[1,5-a]pyrimidine
163. 7-[(4-(5-Bromo-2-(tetrazol-5-yl)pyrrol-1-yl)phenyl)methylamino]-5-ethylpyrazolo[1,5-a]pyrimidine
164. 7-[(4-(5-Chloro-2-(tetrazol-5-yl)pyrrol-1-yl)phenyl)methylamino]-5-ethylpyrazolo[1,5-a]pyrimidine
165. 5-Ethyl-7-[(4-(5-methyl-2-(tetrazol-5-yl)pyrrol-1-yl)phenyl)methylamino]pyrazolo[1,5-a]pyrimidine
166. 5-Ethyl-7-[(4-(5-fluoro-2-(tetrazol-5-yl)pyrrol-1-yl)phenyl)methylamino]pyrazolo[1,5-a]pyrimidine
167. 5-Ethyl-7-[(4-(2-(tetrazol-5-yl)-5-trifluoromethylpyrrol-1-yl)phenyl)methylamino]pyrazolo[1,5-a]pyrimidine
168. 7-[(4-(4-Bromo-2-(tetrazol-5-yl)pyrrol-1-yl)phenyl)methylamino]-5-ethylpyrazolo[1,5-a]pyrimidine
169. 7-[(4-(4-Chloro-2-(tetrazol-5-yl)pyrrol-1-yl)phenyl)methylamino]-5-ethylpyrazolo[1,5-a]pyrimidine
170. 7-[(4-(3,5-Dichloro-2-(tetrazol-5-yl)pyrrol-1-yl)phenyl)methylamino]-5-ethylpyrazolo[1,5-a]pyrimidine
171. 7-[(4-(3,5-Dibromo-2-(tetrazol-5-yl)pyrrol-1-yl)phenyl)methylamino]-5-ethylpyrazolo[1,5-a]pyrimidine
172. 5-Methyl-7-[N-methyl-N-((4-(2-(tetrazol-5-yl)pyrrol-1-yl)phenyl)methyl)amino]pyrazolo[1,5-a]pyrimidine
173. 5-Ethyl-7-[N-methyl-N-((4-(2-(tetrazol-5-yl)pyrrol-1-yl)phenyl)methyl)amino]pyrazolo[1,5-a]pyrimidine
174. 7-[(3-Bromo-2-(2-(tetrazol-5-yl)phenyl)benzofuran-5-yl)methylamino]-5-methylpyrazolo[1,5-a]pyrimidine
175. 7-[(3-Bromo-2-(2-(tetrazol-5-yl)phenyl)benzofuran-5-yl)methylamino]-5-ethylpyrazolo[1,5-a]pyrimidine
176. 7-[(3-Bromo-2-(2-(tetrazol-5-yl)phenyl)benzofuran-5-yl)methylamino]-5-propylpyrazolo[1,5-a]pyrimidine
177. 7-[(3-Bromo-2-(2-(tetrazol-5-yl)phenyl)benzofuran-5-yl)methylamino]-5-butylpyrazolo[1,5-a]pyrimidine
178. 7-[(3-Bromo-2-(2-(tetrazol-5-yl)phenyl)benzofuran-5-yl)methylamino]-5cyclopropylpyrazolo 1,5-a]pyrimidine
179. 7-[(3-Bromo-2-(2-(tetrazol-5-yl)phenyl)benzofuran-5-yl)methylamino]-3-chloro-5-methylpyrazolo[1,5-a]pyrimidine
180. 7-[(3-Bromo-2-(2-(tetrazol-5-yl)phenyl)benzofuran-5-yl)methylamino]-3-chloro-5-ethylpyrazolo[1,5-a]pyrimidine
181. 7-[(3-Bromo-2-(2-(tetrazol-5-yl)phenyl)benzofuran-5-yl)methylamino]-5-methyl-3-nitropyrazolo[1,5-a]pyrimidine
182. 7-[(3-Bromo-2-(2-(tetrazol-5-yl)phenyl)benzofuran-5-yl)methylamino]-5-ethyl-3-nitropyrazolo[1,5-a]pyrimidine
183. 7-[(3-Bromo-2-(2-(tetrazol-5-yl)phenyl)benzofuran-5-yl)methylamino]-3-cyano-5-ethylpyrazolo[1,5-a]pyrimidine
184. 7-[(3-Bromo-2-(2-(tetrazol-5-yl)phenyl)benzofuran-5-yl)methylamino]-5-ethyl-3-methylpyrazolo[1,5-a]pyrimidine
185. 3-Bromo-7-[(3-Bromo-2-(2-(tetrazol-5-yl)phenyl)benzofuran-5-yl)methylamino]-5-ethylpyrazolo[1,5-a]pyrimidine
186. 7-[(3-Bromo-2-(2-(tetrazol-5-yl)phenyl)benzofuran-5-yl)methylamino]-3,5-diethylpyrazolo[1,5-a]pyrimidine
187. 3-Cyano-5-ethyl-7-[(4-(2-(tetrazol-5-yl)pyrrol-1-yl)phenyl)methylamino]pyrazolo[1,5-a]pyrimidine
188. 3-Bromo-5-ethyl-7-[(4-(2-(tetrazol-5-yl)pyrrol-1-yl)phenyl)methylamino]pyrazolo[1,5-a]pyrimidine
189. 3-Chloro-5-methyl-7-[(4-(2-(tetrazol-5-yl)pyrrol-1-yl)phenyl)methylamino]pyrazolo[1,5-a]pyrimidine
190. 3-Cyano-5-ethyl-7-[(4-(2-(tetrazol-5-yl)pyrrol-1-yl)phenyl)methylamino]pyrazolo[1,5-a]pyrimidine
191. 5-Ethyl-7-[(4-(2-(tetrazol-5-yl)pyrrol-1-yl)phenyl)methylamino]-3-nitropyrazolo[1,5-a]pyrimidine
192. 5-Ethyl-7-[(4-(2-(tetrazol-5-yl)pyrrol-1-yl)phenyl)methylamino]-3-methylpyrazolo[1,5-a]pyrimidine
193. 4-[(3-Bromo-2-(2-(tetrazol-5-yl)phenyl)benzofuran-5-yl)methylamino]-2-methylimidazo[1,5-a]pyrimidine
194. 4-[(3-Bromo-2-(2-(tetrazol-5-yl)phenyl)benzofuran-5-yl)methylamino]-2-ethylimidazo[1,5-a]pyrimidine
195. 4-[(3-Bromo-2-(2-(tetrazol-5-yl)phenyl)benzofuran-5-yl)methylamino]-2-ethyl-8-methylimidazo[1,5-a]pyrimidine 196. 4-[(3-Bromo-2-(2-(tetrazol-5-yl)phenyl)benzofuran-5-yl)methylamino]-2-ethylimidazo[1,5-a]pyrimidine-6-carboxylic acid
197. 4-[(3-Bromo-2-(2-(tetrazol-5-yl)phenyl)benzofuran-5-yl)methylamino]-2-methylimidazo[1,5-a]pyrimidine-6-carboxylic acid
198. 2-Methyl-4-[(4-(2-(tetrazol-5-yl)pyrrol-1-yl)phenyl)methylaminpo]imidazo[1,5-a]pyrimidine
199. 2-Ethyl-4-[(4-(2-(tetrazol-5-yl)pyrrol-1-yl)phenyl)methylamino]imidazo[1,5-a]pyrimidine
200. 2-Methyl-4-[(4-(2-(tetrazol-5-yl)pyrrol-1-yl)phenyl)methylamino]imidazo[1,5-a]pyrimidine-6-carboxylic acid
201. 2-Ethyl-4-[(4-(2-(tetrazol-5-yl)pyrrol-1-yl)phenyl)methylamino]imidazo[1,5-a]pyrimidine-6-carboxylic acid
202. 2-Ethyl-4-[(4-(2-(tetrazol-5-yl)pyrrol-1-yl)phenyl)methylamino]-8-methylimidazo[1,5-a]pyrimidine
203. 5-[(3-Bromo-2-(2-(tetrazol-5-yl)phenyl)benzofuran-5-yl)methylamino]-7-methylimidazo[1,2-a]pyrimidine-2-carboxylic acid
204. 5-[(3-Bromo-2-(2-(tetrazol-5-yl)phenyl)benzofuran-5-yl)methylamino]-7-ethylimidazo[1,2-a]pyrimidine-2-carboxylic acid
205. 5-[(3-Bromo-2-(2-(tetrazol-5-yl)phenyl)benzofuran-5-yl)methylamino]-7-methylimidazo[1,2-a]pyrimidine-3-carboxylic acid
206. 5-[(3-Bromo-2-(2-(tetrazol-5-yl)phenyl)benzofuran-5-yl)methylamino]-7-ethylimidazo[1,2-a]pyrimidine-3-carboxylic acid
207. 5-[(3-Bromo-2-(2-(tetrazol-5-yl)phenyl)benzofuran-5-yl)methylamino]-7-ethyl-3-formylimidazo[1,2-a]pyrimidine
208. 5-[(3-Bromo-2-(2-(tetrazol-5-yl)phenyl)benzofuran-5-yl)methylamino]-7-ethyl-3-hydroxymethylimidazo[1,2-a]pyrimidine
209. 5-[(3-Bromo-2-(2-(tetrazol-5-yl)phenyl)benzofuran-5-yl)methylamino]-7-ethylimidazo[1,2-a]pyrimidine
210. 7-Methyl-5-[(4-(2-(tetrazol-5-yl)pyrrol-1-yl)phenyl)methylamino]imidazo[1,5-a]pyrimidine-3-carboxylic acid
211. 7-Ethyl-5-[(4-(2-(tetrazol-5-yl)pyrrol-1-yl)phenyl)methylamino]imidazo[1,5-a]pyrimidine-3-carboxylic acid
212. 7-Ethyl-5-[(4-(2-(tetrazol-5-yl)pyrrol-1-yl)phenyl)methylamino]imidazo[1,5-a]pyrimidine-2-carboxylic acid
213. 3-Cyano-7-ethyl-5-[(4-(2-(tetrazol-5-yl)pyrrol-1-yl)phenyl)methylamino]imidazo[1,5-a]pyrimidine
214. 7-Ethyl-5-[(4-(2-(tetrazol-5-yl)pyrrol-1-yl)phenyl)methylamino]-3-formylimidazo[1,5-a]pyrimidine
215. 7-Ethyl-5-[(4-(2-(tetrazol-5-yl)pyrrol-1-yl)phenyl)methylamino]-3-hydroxymethylimidazo[1,5-a]pyrimidine
216. 2-[N-(5-Methylpyrazolo[1,5-a]pyrimidine-7-yl)-N-((2'-(tetrazol-5-yl)biphenyl-4-yl)methyl)amino]acetic acid
217. 2-[N-(5-Ethylpyrazolo[1,5-a]pyrimidine-7-yl)-N-((2'-(tetrazol-5-yl)biphenyl-4-yl)methyl)amino]acetic acid
218. Ethyl 2-[N-(5-Methylpyrazolo[1,5-a]pyrimidine-7-yl)-N-((2'-(tetrazol-5-yl)biphenyl-4-yl)methyl)amino]acetate
219. Ethyl 2-[N-(5-Ethylpyrazolo[1,5-a]pyrimidine-7-yl)-N-((2'-(tetrazol-5-yl)biphenyl-4-yl)methyl)amino]acetate
220. Methyl 2-[N-(5-Methylpyrazolo[1,5-a]pyrimidine-7-yl)-N-((2'-(tetrazol-5-yl)biphenyl-4-yl)methyl)amino]acetate
221. Methyl 2-[N-(5-Ethylpyrazolo[1,5-a]pyrimidine-7-yl)-N-((2'-(tetrazol-5-yl)biphenyl-4-yl)methyl)amino]acetate
222. 2-[N-(5-Methylpyrazolo[1,5-a]pyrimidine-7-yl)-N-((2'-(tetrazol-5-yl)biphenyl-4-yl)methyl)amino]acetamide
223. 2-[N-(5-Ethylpyrazolo[1,5-a]pyrimidine-7-yl)-N-((2'-(tetrazol-5-yl)biphenyl -4-yl)methyl)amino]acetamide
224. N,N-Dimethyl-2-[N-(5-Ethylpyrazolo[1,5-a]pyrimidine-7-yl)-N-((2'-(tetrazol-5-yl)biphenyl-4-yl)methyl)amino]acetamide
225. 2-[N-(5-Ethylpyrazolo[1,5-a]pyrimidine-7-yl)-N-((2'-(tetrazol-5-yl)biphenyl-4-yl)methyl)amino]-N-methylacetamide
226. 2-[N-(5-Ethylpyrazolo[1,5-a]pyrimidine-7-yl)-N-((2'-(tetrazol-5-yl)biphenyl-4-yl)methyl)amino]acetonitrile
227. 5-[(N-(5-Ethylpyrazolo[1,5-a]pyrimidine-7-yl)-N-((2'-(tetrazol-5-yl)biphenyl-4-yl)methyl)amino)methyl]tetrazole
228. Pivaloyloxymethyl 2-[N-(5-Ethylpyrazolo[1,5-a]pyrimidine-7-yl)-N-((2'-(tetrazol-5-yl)biphenyl-4-yl)methyl)amino]acetate
229. 2-[N-((3-Bromo-2-(2-(tetrazol-5-yl)phenyl)benzofuran-5-yl)methyl)-N-(5-methylpyrazolo[1,5-a]pyrimidine-7-yl)amino]acetic acid
230. 2-[N-((3-Bromo-2-(2-(tetrazol-5-yl)phenyl)benzofuran-5-yl)methyl)-N-(5-ethylpyrazolo[1,5-a]pyrimidine-7-yl)amino]acetic acid
231. Ethyl 2-[N-((3-Bromo-2-(2-(tetrazol-5-yl)phenyl)benzofuran-5-yl)methyl)-N-(5-ethylpyrazolo[1,5-a]pyrimidine-7-yl)amino]acetate
232. Methyl 2-[N-((3-Bromo-2-(2-(tetrazol-5-yl)phenyl)benzofuran-5-yl)methyl-N-(5-ethylpyrazolo[1,5-a]pyrimidine-7-yl)amino]acetate
233. 2-[N-(5-Methylpyrazolo[1,5-a]pyrimidine-7-yl)-N-((4-(2-(tetrazol-5-yl)pyrrol-1-yl)phenyl)methyl)amino]acetic acid
234. 2-[N-(5-Ethylpyrazolo[1,5-a]pyrimidine-7-yl)-N-((4-(2-(tetrazol-5-yl)pyrrol-1-yl)phenyl)methyl)amino]acetic acid
235. Methyl 2-[N-(5-Ethylpyrazolo[1,5-a]pyrimidine-7-yl)-N-((4-(2-(tetrazol-5-yl)pyrrol-1-yl)phenyl)methyl)amino]acetate
236. Ethyl 2-[N-(5-Ethylpyrazolo[1,5-a]pyrimidine-7-yl)-N-((4-(2-(tetrazol-5-yl)pyrrol-1-yl)phenyl)methyl)amino]acetate
237. 2-[N-(5-Ethylpyrazolo[1,5-a]pyrimidine-7-yl)-N-((4-(2-(tetrazol-5-yl)pyrrol-1-yl)phenyl)methyl)amino]acetamide
238. 2-[N-(3-Chloro-5-methylpyrazolo[1,5-a]pyrimidine-7-yl)-N-((2'-(tetrazol-5-yl)biphenyl-4-yl)methyl)amino]acetic acid
239. 2-[N-(3-Chloro-5-ethylpyrazolo[1,5-a]pyrimidine-7-yl)-N-((2'-(tetrazol-5-yl)biphenyl-4-yl)methyl)amino]acetic acid
240. Ethyl 2-[N-(3-Chloro-5-ethylpyrazolo[1,5-a]pyrimidine-7-yl)-N-((2'-(tetrazol-5-yl)biphenyl -4-yl)methyl)amino]acetate
241. Ethyl 2-[N-(3-Chloro-5-methylpyrazolo[1,5-a]pyrimidine-7-yl)-N-((2'-(tetrazol-5-yl)biphenyl-4-yl)methyl)amino]acetate
242. 2-[N-(5-Ethyl-3-methylpyrazolo[1,5-a]pyrimidine-7-yl)-N-((2'-(tetrazol-5-yl)biphenyl-4-yl)methyl)amino]acetic acid
243. 2-[N-(3,5-Diethylpyrazolo[1,5-a]pyrimidine-7-yl)-N-((2'-(tetrazol-5-yl)biphenyl-4-yl)methyl)amino]acetic acid
244. 2-[N-(5-Ethyl-3-propylpyrazolo[1,5-a]pyrimidine-7-yl)-N-((2'-(tetrazol-5-yl)biphenyl-4-yl)methyl)amino]acetic acid
245. 2-[N-(5-Ethyl-3-nitropyrazolo[1,5-a]pyrimidine-7-yl)-N-((2'-(tetrazol-5-yl)biphenyl-4-yl)methyl)amino]acetic acid
246. 2-[N-(3-Cyano-5-ethylpyrazolo [1,5-a]pyrimidine-7-yl)-N-((2'-(tetrazol-5-yl)biphenyl-4-yl)methyl)amino] acetic acid 247. 2-[N-(3-Bromo-5-ethylpyrazolo[1,5-a]pyrimidine-7-yl)-N-((2'-(tetrazol-5-yl)biphenyl-4-yl)methyl)amino]acetic acid 248. 2-[N-(2,5-Diethyl-3-methylpyrazolo[1,5-a]pyrimidine-7-yl)-N-((2'-(tetrazol-5-yl)biphenyl-4-yl)methyl)amino]acetic acid 249. 2-[N-(5-Ethylpyrazolo[1,5-a]pyrimidine-7-yl)-N-(2'-(tetrazol-5-yl)biphenyl-4-yl)amino]acetic acid 250. Methyl 2-[N-(5-Ethylpyrazolo[1,5-a]pyrimidine-7-yl)-N-(2'-(tetrazol-5-yl)biphenyl-4-yl)amino]acetate 251. Ethyl 2-[N-(5-Ethylpyrazolo[1,5-a]pyrimidine-7-yl)-N-(2'-(tetrazol-5-yl)biphenyl-4-yl)amino]acetate 252. 2-[N-(5-Ethylpyrazolo[1,5-a]pyrimidine-7-yl)-N-(2'-(tetrazol-5-yl)biphenyl-4-yl)amino]acetamide The most preferred compounds are as follows:

5-Methyl-7-[(2'-(tetrazol-5-yl)biphenyl-4-yl)methylamino]pyrazolo[1,5-a]pyrimidine 5-Ethyl-7-[2'-(tetrazol-5-yl)biphenyl-4-yl)methylamino]pyrazolo[1,5-a]pyrimidine 3-Chloro-5-ethyl-7-[(2'-(tetrazol-5-yl)biphenyl-4-yl)methylamino]pyrazolo[1,5-a]pyrimidine 7-[(3-Bromo -2-(2-tetrazol-5-yl)phenyl)benzofuran-5-yl)methylamino]-5-ethylpyrazolo [1,5-a]pyrimidine 2-[N-(5-Methylpyrazolo[1,5-a]pyrimidine-7-yl)-N-((2'-(tetrazol-5-yl)biphenyl-4-yl)methyl)amino]acetic acid 2-[N-(5-Ethylpyrazolo[1,5-a]pyrimidine-7-yl)-N-((2'-(tetrazol-5-yl)biphenyl-4-yl)methyl)amino]acetic acid.

This invention also includes processes for preparing compounds of the formula (I) above. The principal processes are as follows:

1) reacting a compound of the formula (II)

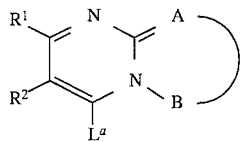
(II)

in which $L^a$ is a leaving group, with a compound of the formula (III)

$HX(CHR^3)_n-Ar^1-Y-Ar^2$ (III)

2) reacting a compound of the formula (IV)

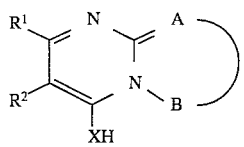
(IV)

with a compound of the formula (V)

$L^bCHR^3-Ar^1-Y-Ar^2$ (V)

in which $L^b$ is a leaving group.

3) reacting a compound of the formula (IX)

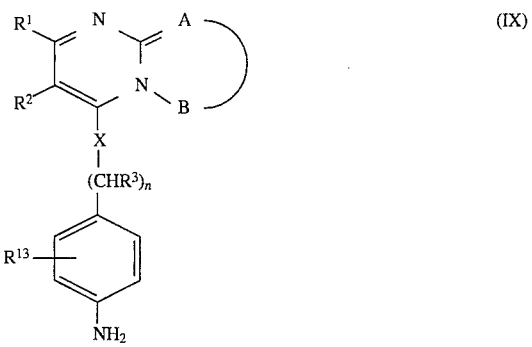
(IX)

with a compound of the formula X, XI or XII (Scheme 2, below).

4) converting a compound of the formula (I) in which $R^{16}$ or $R^{20}$ is cyano to give a compound of the formula (I) in which $R^{16}$ or $R^{20}$ is COOH.

5) reacting a compound of the formula (I) in which $R^{16}$ or $R^{20}$ is cyano with an azide to give a compound of the formula (I) in which $R^{16}$ or $R^{20}$ is tetrazolyl.

6) oxidising a compound of the formula (I) in which $R^{16}$ is mercapto to give a compound in which $R^{16}$ is $SO_3H$.

7) reacting a compound of the formula (I) in which $R^{16}$ is amino with trifluoromethane sulfonyl chloride or with trifluorosulfonic acid anhydride to give a compound in which $R^{16}$ is $NHSO_2CF_3$.

8) removing a protecting group, or hydrolysing an ester to give the unprotected free acid.

The reactions of process steps (1) and (2) are summarised in the following scheme:

Scheme 1

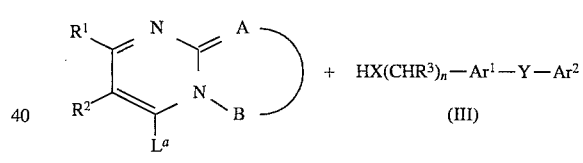

Compounds of formula I, in which $R^{16}$ or $R^{20}$ are acidic substituents according to their general meaning, are prepared from appropriate precursors of formula I by standard methods. In particular, carboxylic acids ($R^{16}$, $R^{20}$=COOH) are prepared from their corresponding esters or other derivatives, in which the carboxylic acid is protected, or from the corresponding nitriles ($R^{16}$, $R^{20}$=COO($C_{1-4}$-alkyl), $COOP^1$, or cyano). Tetrazoles ($R^{16}$, $R^{20}$=5-tetrazolyl) are prepared from corresponding nitriles or protected tetrazoles, in which $R^{16}$ or $R^{20}$ is cyano or a group of formula (M), sulfonic acids ($R^{16}$=SO$_3$H) from their esters ($R^{16}$=SO$_2$(OC$_{1-4}$-alkyl)), their chlorides ($R^{16}$=SO$_2$Cl), or their thiols ($R^{16}$=mercapto), phosphonic acids ($R^{16}$=PO(OH)$_2$) from their esters ($R^{16}$=PO(OC$_{1-4}$-alkyl)$_2$), trifluoromethanesulfonamides ($R^{16}$=NHSO$_2$CF$_3$) from the corresponding nitro via the amino derivatives ($R^{16}$=NO$_2$ or NH$_2$). These processes may also be carried out in an earlier stage of the synthesis of compounds of formula I during the preparation of compounds of formula III or formula V (Scheme 1), however, tetrazoles ($R^{16}$, $R^{20}$=5-tetrazolyl) or carboxylic acids ($R^{16}$, $R^{20}$=COOH) of formula I are preferably prepared in this stage of the sequence. It is obvious to those skilled in the art, that substituents $R^2$, $R^5$, $R^7$, $R^9$, $R^{10}$, or $R^{14}$ in compounds of formula I having the same meaning are or may also be transferred to acidic substituents of the meaning of $R^{16}$ or $R^{20}$ during the described processes.

Esters of formula I ($R^{16}$, $R^{20}$=COO(C$_{1-4}$-alkyl)) are cleaved to their carboxylic acids ($R^{16}$, $R^{20}$=COOH) using standard methods (R. Sustmann, H. G. Korth, in Houben-Weyl, "Methoden der Organischen Chemie", Vol. E 5, p. 223 ff.; T. W. Greene, P. G. M. Wuts, "Protective Groups in Organic Synthesis", 2nd Ed., p. 227 ff.). Preferred methods use alkali hydroxides, particularly sodium or potassium hydroxide, in water or mixtures of water and alcohols at room temperature or at elevated temperatures up to the boiling point of the mixture. Preferred alcohols contain the same C$_{1-4}$-alkyl as the ester substituent $R^{16}$ or $R^{20}$. tert.-Butyl esters ($R^{16}$, $R^{20}$=COOC(CH$_3$)$_3$) may be cleaved by using acidic conditions of the reaction, preferred by using trifluoroacetic acid in solvents such as dichloromethane or chloroform. The conversion of nitriles of formula I ($R^{16}$, $R^{20}$=cyano) to carboxylic acids I ($R^{16}$, $R^{20}$=COOH) requires heating of the nitriles in alkali hydroxide solutions.

Compounds of formula I, in which one of the substituents, in particular the substituents $R^{16}$ or $R^{20}$, is a protected carboxylic acid group COOP$^{16}$, are prepared from the corresponding acids by known methods. In preferred methods the acid is alkylated in the presence of a base by an appropriate alkylating agent P$^1$Hal, in which the halogen preferably is chlorine, bromine, or iodine. Examples for such alkylating agents are (chloromethyl)methylether, (chloromethyl)(2-methoxyethyl)ether, phenacyl bromide, cyclohexyl 2-chloropropionate, ethyl 2-chloropropionate, 1-chloro-1-(ethoxycarbonyloxy)ethane, 1-chloro-1-(isopropoxycarbonyloxy)ethane, 1-chloro-1-(cyclohexyloxycarbonyloxy)ethane, chloro(ethoxycarbonyloxy) methane, chloro(isopropoxycarbonyloxy)methane, chloro(cyclohexyloxycarbonyloxy)methane, chloromethyl pivaloate, chloromethyl propionate, chloromethyl acetate, 3-phthalidyl bromide, 4-bromomethyl- 5-methyl-2-oxo-1,3-dioxolene. The reaction is carried out in solvents such as acetone, butanone, acetonitrile, DMSO, DMF, or N,N-dimethyl acetamide, preferably at room temperature, in the presence of bases such as potassium carbonate, sodium carbonate, sodium hydride, sodium hydroxide, potassium t-butoxide. In a particular preferred method potassium carbonate in DMF or N,N-dimethyl acetamide is used.

Tetrazoles of the formula I, in which $R^{16}$ or $R^{20}$ is 5-tetrazolyl, may be prepared from nitriles of the formula I ($R^{16}$, $R^{20}$=CN) or carboxylic acids of the formula I ($R^{16}$, $R^{20}$=COOH). The conversion of the nitriles may be carried out directly using inorganic azides, or indirectly by preparation of an intermediate compound I, in which $R^{16}$ or $R^{20}$ is a protected tetrazole of the formula (M), and subsequent removal of the protecting group $P^2$. Those intermediates may be isolated during the process or transferred to the unprotected tetrazole without their isolation. It may be advantageous to convert compounds containing a tetrazole protecting group to compounds with different protecting group $P^2$ during the process.

Preferred methods for the direct conversion to tetrazoles of the formula I use sodium azide in polar solvents such as DMF, N-methylpyrrolidinone, 1,3-dimethylimidazolidin-2-one, DMSO, diethylsulfoxide at temperatures between 100° C. and 160° C. and are usually catalyzed by ammonium chlorides. Particularly preferred methods are heating of the nitriles with NaN$_3$ in the presents of NH$_4$Cl or LiCl at 120° C. to 140° C. (W. G. Finnegan, R. A. Henry, R. Lofquist, J. Am. Chem. Soc. 1958, 80, 3908; G. F. Holland, J. N. Peteira, J. Med. Chem. 1967, 10, 149), heating in the presence of Et$_3$NHCl in N-methylpyrrolidinone at 150° C. (P. R. Bernstein, E. P. Vacek, Synthesis 1987, 1133), or heating of the nitrile with aluminum azide in boiling tetrahydrofuran (E. R. Wagner, J. Org. Chem. 1973, 38, 2976).

Methods for the preparation of tetrazoles of the formula I, which run through an intermediate I containing a protected tetrazole of the formula (M), are known from the literature: J. V. Duncia, M. E. Pierce, J. B. Santella III, J. Org. Chem. 1991, 56, 2395; Eur. Patent Appl. EP 291,969). Preferred methods are heating of a nitrile I ($R^{16}$, $R^{20}$=cyano) with a tri(C$_{1-4}$-alkyl)stannyl azide or triphenylstannyl azide, particularly with trimethylstannyl azide or tri(n-butyl)stannyl azide, in toluene, xylene, mesitylene, or in DMF. The stannyl protecting group is removed in an additional step using basic or acidic reaction conditions. Preferred are acidic conditions and include stirring in the presence of mineral acids such as hydrochloric acid in inert solvents such as methanol, ethanol, ether, or THF at room temperature or slight warming of the mixture. They include also stirring with saturated aqueous ammonium chloride solution or stirring with silicagel using the above mentioned solvents. Reactions leading to compounds containing the protective group $P^2$=trimethylstannyl may be preferably carried out with preformed trimethylstannyl azide. Tri(n-butyl)stannyl azide preferably is prepared from tri(n-butyl)stannyl chloride and sodium azide, and used in situ for the conversion (International Patent Appl. WO 92/02508). These products are preferably not isolated and converted to the unprotected tetrazole or to compounds of the formula I containing the protective group $P^2$=CPh$_3$, which is removed using basic or acidic conditions. Preferred conditions for this reaction use mineral acids such as hydrochloric acid in solvents such as methanol, ethanol, THF, or dioxane, or aqueous acetic acid, which may contain additional amounts of the above mentioned organic solvents. The reaction is carried out at room temperature, however, heating of the mixture may be necessary in some cases. The protective group $P^2$=CPh3 is preferably introduced in an earlier stage of the sequence leading to corresponding compounds of the formula III or V, and finally is removed from the corresponding compounds of the formula I. Preferred methods for its introduction use triphenylmethyl chloride and amines as base such as triethylamine or pyridine in solvents such as dichloromethane or chloroform.

The other mentioned protective groups $P^2$ of the present invention are also preferably introduced into an earlier intermediate of the sequence. Corresponding compounds, in which $P^2$ is tert.-butyl, benzyl, 4-methylbenzyl, 4-methoxybenzyl, 4-nitrobenzyl, 2,4,6-trimethylbenzyl, 2-cyanoethyl, or 4-nitrophenyl are prepared from corresponding carboxylic acids by known methods. The sequence starts with the preparation of corresponding primary amides by standard methods, which are chlorinated to iminoyl chlorides, preferred by using PCl$_5$, POCl$_3$, or SOCl$_2$. These chlorides react with azides, preferred with sodium, trimethylsilyl, or trimethylstannyl azide, in the presence of a base such as triethylamine to the desired protected tetrazoles. Benzyl protective groups $P^2$ are preferably removed by hydrogenation using standard methods in ethanol, methanol, or ethyl acetate as solvents, which may contain additional amounts of acetic acid, and Raney-Ni or Pd on charcoal as common catalysts. The group 2-cyanoethyl is preferably removed by aqueous sodium hydroxide solution, which may contain an additional amount of an organic solvent such as methanol, ethanol, THF, or dioxane. The protective group $P^2$=4-nitrophenyl is removed by stirring with an alkali metal alkanethiolate or an alkali metal alkanolate, preferred with sodium or potassium methoxide, sodium or potassium ethoxide, or sodium or potassium propanethiolate in polar solvents such as DMF or N-methylpyrrolidinone at room temperature (Eur. Patent Appl. EP 495,626). The above mentioned tetrazole protective groups $P^2$=$C_{1-4}$-alkoxymethyl, methylthiomethyl, 2-(trimethylsilyl)ethyl, benzenesulfonyl, and 4-methylbenzenesulfonyl are introduced and removed by standard procedures (T. W. Greene, P. G. M. Wuts, "Protective Groups in Organic Synthesis", 2nd Edition, John Wiley & Sons).

Preferred methods for the preparation of compounds, in which $R^{16}$ or $R^{20}$ is 5-tetrazolyl, are a) heating of nitriles with sodium azide in the presence of triethylammonium chloride in N-methylpyrrolidinone, b) heating of nitriles with trimethylstannyl azide in toluene and acidic work-up of the mixture with hydrochloric acid, ammonium chloride, or silica gel, c) heating of nitriles with tri(n-butyl)stannyl azide, which is prepared in situ from tri(n-butyl)stannyl chloride and sodium azide, in toluene, and acidic work-up with hydrochloric acid, d) removal of the protecting group $P^2$=$CPh_3$ by aqueous acetic acid, mixtures of aqueous HCl and THF or methanol, or solutions of sodium hydroxide in aqueous methanol at room temperature, e) removal of the protecting group $P^2$=4-nitrophenyl by stirring with sodium propanethiolate, sodium methoxide, or sodium ethoxide in DMF or N-methylpyrrolidinone at room temperature.

Compounds of the formula I, in which $R^{16}$ is $NHSO_2CF_3$, may be prepared from compounds of the formula I, in which $R^{16}$ is nitro, by reduction to the corresponding primary aromatic amine and its subsequent conversion to the trifluoromethyl sulfonamide. The reduction is carried out by standard procedures (R. Hemmer, W. Lürken, in Houben-Weyl, "Methoden der Organischen Chemie", Vol. E 16 d, p. 815 ff.). Preferred methods use metals such as Zn, Sn, or Fe in acids such as aqueous HCl oder aqueous acetic acid, optionally with addition of an organic solvent such as methanol, ethanol or THF. Other preferred methods use metals in lower states of oxidation, e.g. Sn(II) dichloride in HCl or Ti(III) trichloride in acetone. Particularly preferred is the reduction by catalytic hydrogenation, which uses metal catalysts from metals such as Pd, Pt, or Ni, preferably Pd on charcoal or Raney-Ni, or their oxides such as $PtO_2$ in solvents such as methanol, ethanol, THF, or ethyl acetate, optionally with addition of an acid such as acetic acid. Those catalytic reductions may also be carried out with formic acid in the presence of a trialkylamine such as triethylamine or with ammonium formiate instead of elemental hydrogen (S. Ram, R. E. Ehrenkaufer, Synthesis 1988, 91). The reaction of the primary amine I ($R^{16}$=$NH_2$) to the sulfonamide I ($R^{16}$=$NHSO_2CF_3$) is carried out with trifluoromethylsulfonyl chloride or preferably with trifluorosulfonic acid anhydride in a suitable inert solvent such as toluene, dichloromethane, or chloroform at temperatures between $-78°$ C. and room temperature, preferably by mixing the reagents with cooling and warming to room temperature. The addition of an amine such as triethylamine, diisopropylethylamine, pyridine, 2,6-di-tert.butyl-4-methylpyridine, or 4-dimethylaminopyridine as above is preferred.

Sulfonic acids of the formula I ($R^{16}$=$SO_3H$) may be prepared from appropriate intermediates of the formula I by standard methods for the preparation of aromatic sulfonic acids, preferred from the corresponding sulfonyl chlorides I ($R^{16}$=$SO_2Cl$) (S. Pawlenko, in Houben-Weyl, "Methoden der Organischen Chemie", Vol. E 11/2, p. 1055 ff.; ibid., p. 1067 ff.). These are preferably prepared from aromatic amines I ($R^{16}$=$NH_2$), which in a first step are converted to their diazonium salts by standard methods and in a second step are treated with sulfur dioxide in the presence of Cu(II) chloride and acetic acid or with $NaHSO_3$ in the presence of Cu(II) sulfate and HCl (H. Meerwein, G. Dittmar, R. G öllner, K. Hafner, F. Mensch, O. Steinfort, Chem. Ber. 1957, 90, 841; R. V. Hoffman, Org. Synth. 1981, 60, 121). The sulfonyl chlorides are hydrolyzed to the sulfonic acids I ($R^{16}$=$SO_3H$) by heating in an aqueous solution, preferably in an alkaline aqueous solution, which contains alkali carbonates such as sodium carbonate or potassium carbonate, or alkali hydroxides such as sodium hydroxide or potassium hydroxide. The hydrolysis may be supported by forming of an intermediate ester I ($R^{16}$=$SO_2(OC_{1-4}$-alkyl)) of the sulfonic acid, preferably of a methyl or ethyl ester, which may also be prepared from corresponding intermediates of formula III or formula V. The conversion from the sulfonyl chlorides I is carried out by treating with an $C_{1-4}$-alkoxide or with the corresponding alcohol in pyridine, and the subsequent hydrolysis by the above mentioned conditions. Another preferred method for the preparation of a sulfonic acid of the formula I ($R^{16}$=$SO_3H$) is the oxidation of a thiol of the formula I ($R^{16}$=$SH$). This is preferably carried out by using elemental chlorine or sodium hypochlorite in an aqueous solution, by using potassium permanganate, or by using hydrogen peroxide in the presence of acids such as sulfuric acid or methylsulfonic acid, or in the presence of trifluoroacetic acid anhydride.

Phosphonic acids of formula I ($R^{16}$=$PO(OH)_2$), may be prepared by standard methods for the synthesis of aromatic phosphonic acids from appropriate intermediates (B. Gallenkamp, W. Hofer, B.-W. Krüger, F. Maurer, T. Pfister, in Houben-Weyl, "Methoden der Organischen Chemie", Vol. E 2, p. 300 ff.), preferably by hydrolysis of their esters I ($R^{16}$=$PO(OC_{1-4}$-alkyl)$_2$), particularly preferred by hydrolysis of their ethylesters I ($R^{16}$=$PO(OEt)_2$) (ibid., p. 310 ff.). The hydrolysis is preferably carried out using acidic conditions. Preferred acids, which may be used, are inorganic acids such as sulfuric acid, phosphoric acid, or dry hydrochloric acid, carboxylic acids such as formic acid or acetic acid, organic sulfonic acids such as methanesulfonic acid, trifluoromethanesulfonic acid, or 4-toluenesulfonic acid. The reaction is carried out in an inert solvent such as acetonitrile, optionally with addition of water, at temperatures between room temperature and warming of the mixture.

The synthesis of compounds of formula I is shown in Scheme 1. It starts from intermediates of formula III or formula V, respectively, which preferably contain non-acidic substituents $R^{16}$ or $R^{20}$, in particular $R^{16}$, $R^{20}$=cyano or $COO(C_{1-4}$-alkyl), which finally are converted to the acidic substituents by the above described procedures. The alkylation starting from intermediates of formula V is preferred, if X is S. In the other cases the reaction with intermediates of formula III from scheme 1 is preferred.

Leaving groups $L^a$ in compounds of formula II are halo, $OSi(C_{1-4}\text{-alkyl})_3$, $OSO_2(C_{1-4}\text{-alkyl})$, $OSO_2Ph$, in which the phenyl group optionally may be substituted by methyl, chloro, or nitro. Preferred leaving groups $L^a$ are chloro, bromo, $OSO_2Me$, $OSO_2Ph$, $OSO_2(4\text{-MeC}_6H_4)$, $OSiMe_3$, or $OSiMe_2tBu$, particularly preferred chloro, $OSO_2Me$, or $OSO_2(4\text{-MeC}_6H_4)$, most particularly chloro.

Examples of the reaction of azolofused pyrimidines of formula II, particularly of those in which $L^a$ is chloro, with amines, thiols, alcohols, or phenols according to Scheme 1 are known. Compounds of formula II, in which the leaving group $L^a$ is halo, alkyl- or arylsulfonate, react with amines of formula III in an inert solvent, optionally in the presence of an additional base, at temperatures between room temperature and reflux of the mixture. Inert solvents for this reaction are alcohols such as methanol, ethanol, isopropanol, n-butanol, tert-butanol, or ethyleneglycol, ethers such as diethylether, THF, 1,2-dimethoxyethane, aromatic hydrocarbons such as toluene, xylene, benzene, or chlorobenzene, chlorinated hydrocarbons such as chloroform, dichloromethane, or 1,2-dichloroethane, DMF, or acetonitrile, preferred solvents methanol, ethanol, isopropanol, or acetonitrile. As additional bases there may be used tertiary amines such as triethylamine, diisopropylethylamine, dimethylaniline, diethylaniline, or pyridine, inorganic hydrides such as sodium or potassium hydride, or inorganic carbonates such as sodium, potassium, or lithium carbonate. The most preferred bases are triethylamine, potassium or sodium carbonate. Preferred methods are heating in isopropanol, ethanol, or methanol, especially ethanol, optionally in the presence of at least one equivalent of triethylamine or potassium carbonate. Compounds of formula II, in which the leaving group $L^a$ is a trialkylsilylether, react with amines of formula III by heating at 150° C. to 180° C. This may be carried out in an inert solvent, which allows heating to these temperatures, or without any solvent, optionally in the presence of a weak acid such as ammonium sulfate or toluene-4-sulfonic acid. The reaction of compounds of formula II with thiols, alcohols, or phenols of formula III requires the addition of at least one equivalent of a strong base, e.g. an alkali hydroxide such as sodium, potassium, or lithium hydroxide, an alkali alkoxide, preferably a sodium or potassium alkoxide, particularly their methoxide, ethoxide, or isopropoxide, or an alkali hydride such as sodium or potassium hydride, and is carried out in the above mentioned inert solvents including water for those cases in which hydroxides are used, and including mixtures of water and organic solvents optionally in the presence of a phase transfer catalyst for biphasic mixtures. The reaction of thiols of formula III is preferably carried out with potassium or sodium methoxide or potassium or sodium ethoxide in methanol or ethanol, respectively, particularly preferred with sodium ethoxide in ethanol, the reaction of alcohols or phenols of formula III preferably with sodium hydride in DMF, both reactions being carried out at temperatures between room temperature and 120° C.

The alkylation of compounds of formula IV, in which X is S, O, or $NR^4$, with compounds of formula V leads to specific embodiments of formula I, wherein n=1. Leaving groups $L^b$ in compounds of formula V are chloro, bromo, $OSO_2(C_{1-4}\text{-alkyl})$, or $OSO_2Ph$, in which the phenyl group optionally may be substituted by methyl, chloro, or nitro. Preferred leaving groups $L^b$ are chloro, bromo, $OSO_2Me$, $OSO_2Ph$, or $OSO_2(4\text{-MeC}_6H_4)$, and bromo is particularly preferred. The reaction is carried out in inert solvents such as DMF, DMSO, acetonitrile, benzene, toluene, xylene, ether, THF, 1,2-dimethoxyethane, acetone or butanone at temperatures between room temperature and reflux of the mixture and usually requires the presence of at least one equivalent of a base such as pyridine, triethylamine, diisopropylethylamine, 4-dimethylaminopyridine, potassium carbonate, sodium carbonate, potassium hydride, sodium hydride, potassium hydroxide, or sodium hydroxide. In the case of the alkali hydroxides water may be used as solvent and the reaction may be carried out in a biphasic mixture with an organic solvent in the presence of a phase transfer catalyst. Preferred methods for the alkylation of compounds of formula IV are a) refluxing in acetone or butanone in the presence of potassium carbonate, and b) stirring at room temperature in DMF in the presence of sodium hydride as base. Method b) is particularly preferred.

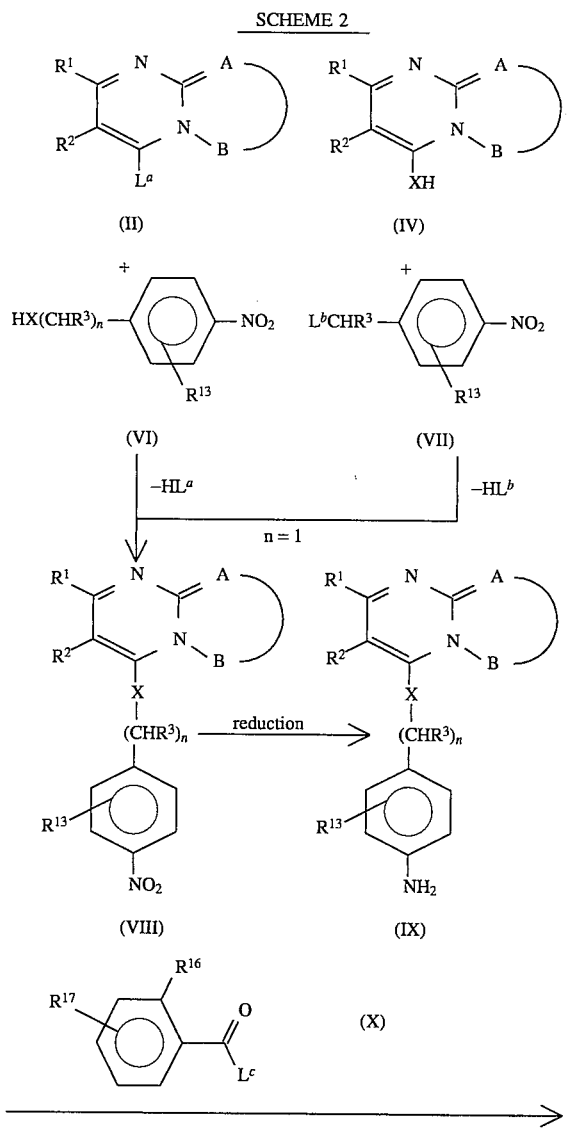

SCHEME 2

SCHEME 2 -continued

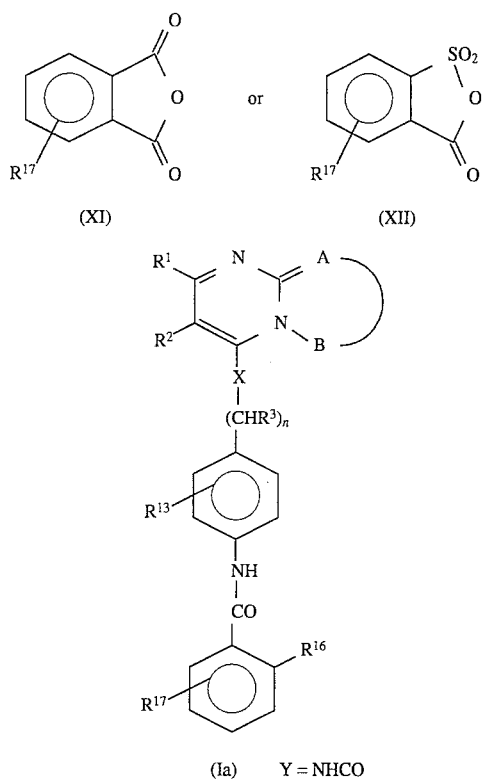

(Ia)   Y = NHCO

In Scheme 2 preferred methods for the synthesis of compounds of formula Ia, which is a specific embodiment of formula I, in which Y is NHCO, are shown. These methods are particularly preferred for compounds of formula Ia, in which $R^{16}$ is COOH or $SO_3H$. The reaction of the intermediates II and IV with nitrobenzenes of formula VI or formula VII, respectively, which are known compounds or may be prepared by known methods, is carried out in the same manner as described above in Scheme 1. The nitro compounds of the formula VIII are reduced to the amino compounds of formula IX by standard methods (R. Hemmer, W. Lürken, in Houben-Weyl, "Methoden der Organischen Chemie", Vol. E 16 d, p. 815 ff.), which are also mentioned above. A preferred method is the reduction by catalytic hydrogenation, which uses Pd on charcoal as a catalyst in solvents such as methanol, ethanol, THF, or ethyl acetate, optionally with addition of an acid such as acetic acid. The amines of formula IX are converted to the amides of the formula Ia by reaction with carboxylic acids X ($L^c$=OH) or other derivatives X, in which $L^c$ is a leaving group, using standard methods, preferably with carboxylic acid chlorides X ($L^c$=Cl)(D. Döpp, H. Döpp, in Houben-Weyl, "Methoden der Organischen Chemie", Vol. E 5, p. 941 ff.). The condensation of carboxylic acids X ($L^c$=OH) with amines of the formula IX is preferably carried out with a reagent for dehydration, particularly in the presence of N,N'-dicyclohexyl carbodiimide. Compounds of formula Ia, in which $R^{16}$ is COOH or $SO_3H$, are preferably prepared by reaction of the amines of formula IX with phthalic acid anhydrides XI or with cyclic anhydrides of 2-sulfobenzoic acid XII, respectively (European Patent Appl. EP 253 310; J. V. Duncia, A. T. Chiu, D. J. Carini, G. B. Gregory, A. L. Johnson, W. A. Price, G. J. Wells, P. C. Wong, J. C. Calabrese, P. B. M. W. M. Timmermans, J. Med. Chem. 1990, 33, 1312). The amine IX is stirred with an equimolar amount or a slight excess of the anhydrides XI or XII in an inert solvent such as diethylether, THF, ethyl acetate, DMF, benzene, toluene, methanol, ethanol, dichloromethane, chloroform, or acetonitrile, optionally in the presence of a base such as sodium hydride, sodium or potassium acetate, sodium or potassium carbonate, pyridine, triethylamine, or ethyldiisopropylamine at room temperature or warming of the mixture. If insoluble inorganic bases are used, it may be advantageous to add a quarternary ammonium salt such as tetrabutyl ammonium chloride, trioctylmethylammonium chloride, or triethylbenzylammonium chloride as a phase transfer catalyst. In preferred methods both compounds are stirred in dichloromethane at room temperature or heated in the presence of potassium carbonate / triethylbenzylammonium chloride.

SCHEME 3

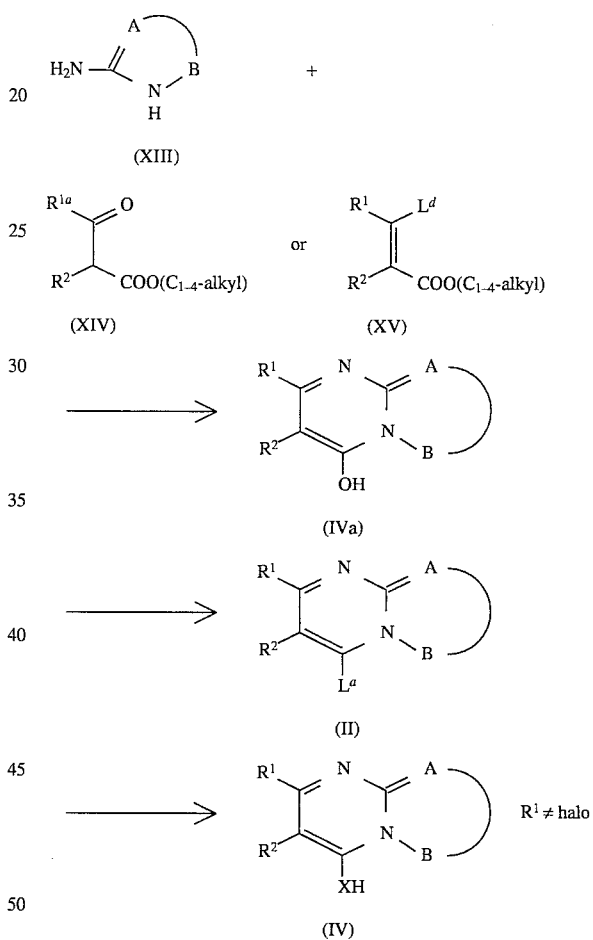

In Scheme 3 methods for the synthesis of the intermediate azolofused pyrimidines II and IV are shown. They start from aminoazoles of the formula XIII, which react with 3-oxoesters of the formula XIV or derivatives XV to fused hydroxypyrimidines of the formula IVa. 3-Oxoesters XIV are used for the synthesis of compounds of formula IVa, in which $R^1$ has the meaning of $R^{1a}$. Compounds of formula IVa, in which $R^1$ has the meaning of $R^{1b}$, may be prepared from compounds of formula XV, in which $R^1$ is $R^{1b}$, particularly in those cases, in which $R^{1b}$ is an amino- or a thiosubstituent according to its general meaning, and if $L^d$ is a thiosubstituent. In general, the leaving group $L^d$ in compounds of the formula XV may have the meaning of $R^{1b}$ including $NH_2$. If $R^1$ is $R^{1a}$, preferred leaving groups $L^d$ are methoxy, ethoxy, amino, methylamino, dimethylamino, anilino, pyrrolidino, piperidino, morpholino, methylthio, or benzylthio, particularly preferred methoxy or ethoxy. If $R^1$ is a thiosubstituent $R^{1b}$, the leaving group $L^d$ has preferably the same meaning as $R^{1b}$. If $R^1$ is an amino substituent $R^{1b}$, $L^d$ is preferably $S(C_{1-4}$-alkyl) or $SCH_2Ph$, particularly preferred $SMe$ or $SCH_2Ph$.

Many examples for the synthesis of fused hydroxypyrimidines IVa and their conversion to derivatives II and IV are known: W. L. Mosby, in "Heterocyclic Systems with Bridgehead Nitrogen Atoms", ed. by A. Weissberger, Interscience Publishers, New York, 1961; J. V. Greenhill, p. 305 ff. (pyrazolopyrimidines), S. W. Schneller, p. 890–891 (triazolopyrimidines), and J. A. Montgomery, J. A. Secrist III, p. 647 ff. (imidazopyrimidines), in "Comprehensive Heterocyclic Chemistry", Vol. 5, Pergamon Press, 1984; M. H. Elnagdi, M. R. H. Elmoghayar, G. E. H. Elgemeie, Adv. Heterocyclic Chem. 1987, 41, 319, in particular: C. F. H. Allen, H. R. Beilfuss, D. M. Burness, G. A. Reynolds, J. F. Tinker, J. A. van Allan, J. Org. Chem. 1959, 24, 779, 787; C. F. H. Allen, G. A. Reynolds, J. F. Tinker, L. A. Williams, J. Org. Chem. 1960, 25,361; Y. Makisumi, Chem. Pharm. Bull. 1962, 10, 612, 620; 1964, 12, 204; W. Ried, K.-P. Peuchert, Liebigs Ann. Chem. 1962, 660 , 104; W. Ried, S. Aboul-Fetouh, Chem. Ztg. 1989, 113, 181; W. A. Kleschick, J. Bordner, J. Heterocyclic Chem. 1989, 26, 1489; K. Esses-Reiter, J. Reiter, J. Heterocyclic Chem. 1987, 24, 1503; J. Reiter, L. Pongo, P. Dvortsak, Tetrahedron 1987, 43, 2497; M. H. Elnagdi, E. M. Kandeel, E. M. Zayed, Z. E. Kandil, J. Heterocyclic Chem. 1977, 14, 155; R. K. Robins, G. R. Revankar, D. E. O'Brien, R. H. Springer, T. Novinson, A. Albert, K. Senga, J. P. Miller, D. G. Streeter, J. Heterocyclic Chem. 1985, 22, 601; R. H. Springer, M. B. Scholten, D. E. O'Brien, T. Novinson, J. P. Miller, R. K. Robins, J. Med. Chem. 1982, 25, 235; K. Senga, T. Novinson, R. H. Springer, R. P. Rao, D. E. O'Brien, R. K. Robins, H. R. Wilson, J. Med. Chem. 1975, 18, 312; K. Senga, T. Novinson, H. R. Wilson, R. K. Robins, J. Med. Chem. 1981, 24, 610; T. Novinson, R. K. Robins, T. R. Matthews, J. Med. Chem. 1977, 20, 296; T. Novinson, B. Bhooshan, T. Okabe, G. R. Revankar, R. K. Robins, K. Senga, H. R. Wilson, J. Med. Chem. 1976, 19, 512; T. Novinson, D. E. O'Brien, R. K. Robins, J. Heterocyclic Chem. 1974, 11, 873; T. Pyl, W. Baufeld, Liebigs Ann. Chem. 1966, 699, 127; Ger. Offen. DE 3 338 292; European Patent Appl. EP 500 137. In particular, the reaction of aminoazoles XIII with ketene-S, S-acetals of formula XV is known: A. Thomas, M. Chakraborty, H. Ila, H. Junjappa, Tetrahedron 1990, 46, 577; T. Eisenächer, R. Pech, R. Böhm, Pharmazie 1992, 47, 580.

The reaction of aminoazoles XIII with the compounds XIV or XV may be carried out under acidic or basic conditions, or, if the esters XIV or XV are liquids and these may be used as a solvent, by heating a mixture of both compounds at temperatures between 120° C. and 200° C., optionally in the presence of an additional inert higher boiling cosolvent. Acidic conditions use heating in carboxylic acids such as acetic acid, or heating in the presence of Lewis acids such as $BF_3$, $ZnCl_2$, $AlCl_3$, or $TiCl_4$ in an inert solvent, preferably in an alcohol containing the same alkyl chain as the esters XIV or XV. It is particularly preferred to use ethanol with ethyl esters XIV or XV. In methods using basic reaction conditions both compounds may be warmed in DMF in the presence of sodium hydride or in the presence of an alkali carbonate such as sodium or potassium carbonate, or may be stirred in aqueous sodium or potassium hydroxide or sodium or potassium carbonate solution containing between 5% and 10% of the base at temperatures between room temperature and 100° C. Preferred basic conditions use sodium or potassium alkoxides in alcohols, which contain the same alkyl chain. Particularly preferred is sodium ethoxide in ethanol and ethyl esters XIV or XV at reflux of the mixture. The reaction of aminoazoles XIII and esters of the formula XIV or formula XV is most preferably carried out by heating in acetic acid.

Fused hydroxypyrimidines IVa are converted to fused halopyrimidines II ($L^a$=halo) by mineral acid halides, preferably to their chloro or bromo derivatives by $POCl_3$, $PCl_{1.5}$, $SOCl_2$, or $POBr_3$, respectively, most preferably by heating in $POCl_3$ at temperatures between 60° C. and 120° C., preferably at reflux, and optionally with addition of an inert solvent such as benzene, toluene, xylene, chlorobenzene, chloroform, or 1,2-dichloroethane. The chlorination may be carried out in the presence of a tertiary amine or amide such as pyridine, N,N-dimethylaniline, N,N-diethylaniline, DMF, or N,N,N',N'-tetramethyl urea. A most preferred method uses heating in $POCl_3$ in the presence of N,N-diethylaniline. Compounds of formula II, in which $L^a$ is $OSO_2(C_{1-4}$-alkyl) or (substituted) $OSO_2Ph$ are prepared from compounds of formula IVa and the corresponding sulfonyl chlorides. The reaction is carried out in the presence of a base such as pyridine, 4-(N,N-dimethylamino) pyridine, potassium carbonate, sodium or potassium hydroxide in inert organic solvents such as chloroform, dichloromethane, toluene, diethylether, or THF. In the case of insoluble inorganic bases a quarternary ammonium salt such as tetrabutylammonium chloride, trioctylmethylammonium chloride, triethylbenzylammonium chloride is added. Compounds of formula II, in which $L^a$ is $OSi(C_{1-4}$-alkyl)$_3$, in particular $OSiMe_3$, are preferably not isolated during the course of the reaction. The silylation of the fused hydroxypyrimidines IVa is carried out by heating at temperatures between 120° C. and 160° C. with an excess of reagents such as hexamethyldisilazane, N,O-bis(trimethylsilyl) acetamide, N,O-bis(trimethylsilyl) trifluoroacetamide, N,N'-bis(trimethylsilyl) urea, or N,O'-bis(trimethylsilyl) carbamate, which may be used as a solvent. The silylation with trimethylsilyl chloride, or trimethylsilyl bromide is carried out in the presence of a base such as pyridine, triethylamine, 4-(N,N-dimethylamino)pyridine in inert solvents such as chloroform, dichloromethane, or toluene.

Compounds of formula IV, in which X is S or $NR^4$, are prepared from compounds of formula II. Preferred compounds II for this conversion are fused chloropyrimidines II ($L^a$=Cl). The reaction with amines $R^4NH_2$ is carried out according to the methods described in Scheme 1. Fused aminopyrimidines IV (X=NH) are prepared with ammonia in an inert solvent, preferably in an alcohol such as methanol, ethanol, or isopropanol. In a preferred modification this reaction is carried out in ethanol by heating in an autoclave. Fused mercaptopyrimidines IV (X=S) are preferably prepared by reaction of compounds II ($L^a$=Cl) with thiourea. Preferred solvents for this reaction are alcohols such as methanol, ethanol, propanol, isopropanol, or butanol, particularly preferred ethanol, and the reaction is preferably carried out by heating at reflux. For this conversion sodium sulfide in water, alcohols, or mixtures thereof, or hydrogen sulfide in basic alcoholic solution, e.g. in methanol or ethanol containing sodium, potassium, or ammonium carbonate may also be used.

The aminoazoles XIII are known compounds or may be prepared by known methods: J. Elguero, p. 273 ff. (aminopyrazoles), M. R. Grimmett, p. 457 ff. (aminoimidazoles), and J. B. Polya, p. 7'ff. (aminotriazoles), in "Comprehensive Heterocyclic Chemistry", Vol. 5, Pergamon Press, 1984; M. H. Elnagdi, F. M. Abdel-Galil, B. Y. Riad, G. E. H. Elgemeie, Heterocycles 1983, 20, 2437; M. H. Elnagdi, M. R. H. Elmoghayar, G. E. H. Elgemeie, Synthesis 1984, 1; M. R. Grimmett, Adv. Heterocyclic Chem. 1980, 27, 241; C. Temple, J. A. Montgomery, in "The Chemistry of Heterocyclic Compounds", ed. by A. Weissberger, E. C. Taylor, Vol. 37 (1,2,4-Triazoles), Wiley-Interscience, New York, 1981. The compounds of formula XIV and formula XV are also known, or they may be prepared by known procedures, e.g. 3-oxoesters XIV according to W. Wierenga, H. I. Skulnick, J. Org. Chem. 1979, 44, 310; ketene-S,S- or ketene-S,N-acetals of formula XV according to methods from E. Schaumann, in Houben-Weyl, "Methoden der Organischen Chemie", Vol. E 11, p. 260 ff., p. 325 ff.,or M. Kolb, Synthesis 1990, 171.

SCHEME 4

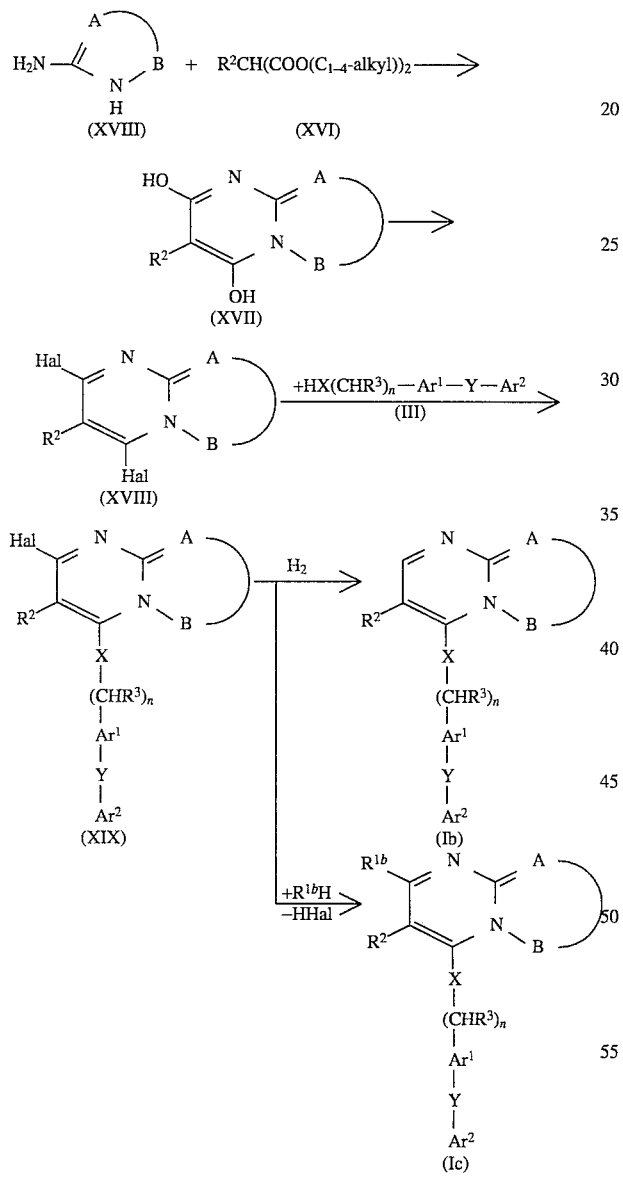

Preferred methods for the synthesis of compounds of formula Ib or formula Ic, which are special embodiments of formula I, in which $R^1$ is hydrogen or the substituent $R^{1b}$, respectively, are shown in Scheme 4. Aminoazoles of formula XIII react with malonic esters XVI to give fused dihydroxypyrimidines XVII, which are halogenated to fused dihalogenopyrimidines XVIII, preferably to fused dichloropyrimidines XVIII (Hal=Cl). Reaction with compounds of formula III leads to compounds of formula XIX, whose remaining halogen atom may be removed by hydrogenation leading to compounds of formula Ib or may be substituted by alcohols, phenols, amines, or thiols $R^{1b}H$ leading to compounds of formula Ic. Examples for the reactions of Scheme 4 are known from the above cited general literature on fused hydroxypyrimidines, in particular: R. H. Springer, M. K. Dimmitt, T. Novinson, D. E. O'Brien, R. K. Robins, L. N. Simon, J. P. Miller, J. Med. Chem. 1976, 19, 291; G. R. Revankar, R. K. Robins, R. L. Tolman, J. Org. Chem. 1974, 39, 1256; T. Novinson, R. K. Robins, T. R. Matthews, J. Med. Chem. 1977, 20, 296; R. K. Robins, G. R. Revankar, D. E. O'Brien, R. H. Springer, T. Novinson, A. Albert, K. Senga, J. P. Miller, D. G. Streeter, J. Heterocyclic Chem. 1985, 22, 601; Y. Makisumi, Chem. Pharm. Bull. 1962, 10, 612; E. Tenor, R. Ludwig, Pharmazie 1971, 26, 534; E. Lippmann, P. Strauch, E. Tenor, Pharmazie 1991, 46, 184.

The reaction of aminoazoles XIII with malonic esters XVI, which are known compounds or may be prepared by known methods, is preferably carried out by using basic conditions. These are described for the similar conversion of 3-oxoesters of formula XIV in Scheme 3. Preferred basic conditions use sodium or potassium alkoxides in alcohols, which contain the same alkyl chain. Particularly preferred is the use of sodium ethoxide in ethanol and ethylesters XVI at reflux of the mixture. The subsequent halogenation to dihalogenides of formula XVIII is also carried out by the methods from Scheme 3, preferably by using $POCl_3$, optionally in the presence of tertiary amines or amides, most particularly preferred by refluxing in $POCl_3$ in the presence of N,N-diethylaniline, leading to dichlorides of formula XVIII (Hal=Cl). The substitution of one halo in compounds of formula XVIII with amines, thiols, alcohols, or phenols of formula III is carried out by methods described in Scheme 1, e.g. by heating of amines of formula III with dichlorides XVIII in alcohols such as methanol, ethanol, propanol, isopropanol, n-butanol, or tert-butanol, preferably in ethanol. It may be advantageous to carry out this reaction at lower temperatures than reflux, e.g. at room temperature or by slight warming of the mixture. The remaining halo in compounds of formula XIX is removed by catalytic hydrogenation, using metal catalysts derived from metals such as Pd, Pt, or Ni, preferably Pd on charcoal or Raney-Ni, or their oxides such as $PtO_2$ in solvents such as methanol, ethanol, THF, or ethyl acetate, optionally with addition of acetic acid and / or sodium acetate. In preferred methods 5% or 10% Pd on charcoal in a mixture of acetic acid and methanol or ethanol at room temperature is used. The reaction of compounds of formula XIX with amines, alcohols, phenols, or thiols $R^{1b}H$ is carried out by methods, which are similar to the substitution of the first halogen atom, however, requires more drastic conditions such as heating in higher boiling solvents and / or under elevated pressure. A preferred method for the substitution with amines $R^{1b}H$ is heating of a chloro derivative XIX (Hal=Cl) with an excess of the amine in solvents such as methanol, ethanol, isopropanol, DMF, acetonitrile, or toluene in an autoclave. Alcohols $R^{1b}H$ react preferably with derivatives of formula XIX by heating with their sodium or potassium alkoxides, which are dissolved in these alcohols, and the reaction is preferably carried out in an autoclave. A preferred process for the reaction with phenols or thiols $R^{1b}H$ involves in a first step the generation of phenolates or thiolates with bases such as sodium hydride in solvents such as DMF and in a second step heating of these reagents with compounds of formula XIX, optionally carried out in an autoclave. The introduction of an amino, alkoxy, or phenoxy substituent $R^{1b}$ may also be carried out using the described conditions by replacement of a substituent $R^{1b}$=alkylthio, preferably by replacement of methylthio, optionally after oxidation to the corresponding sulfone.

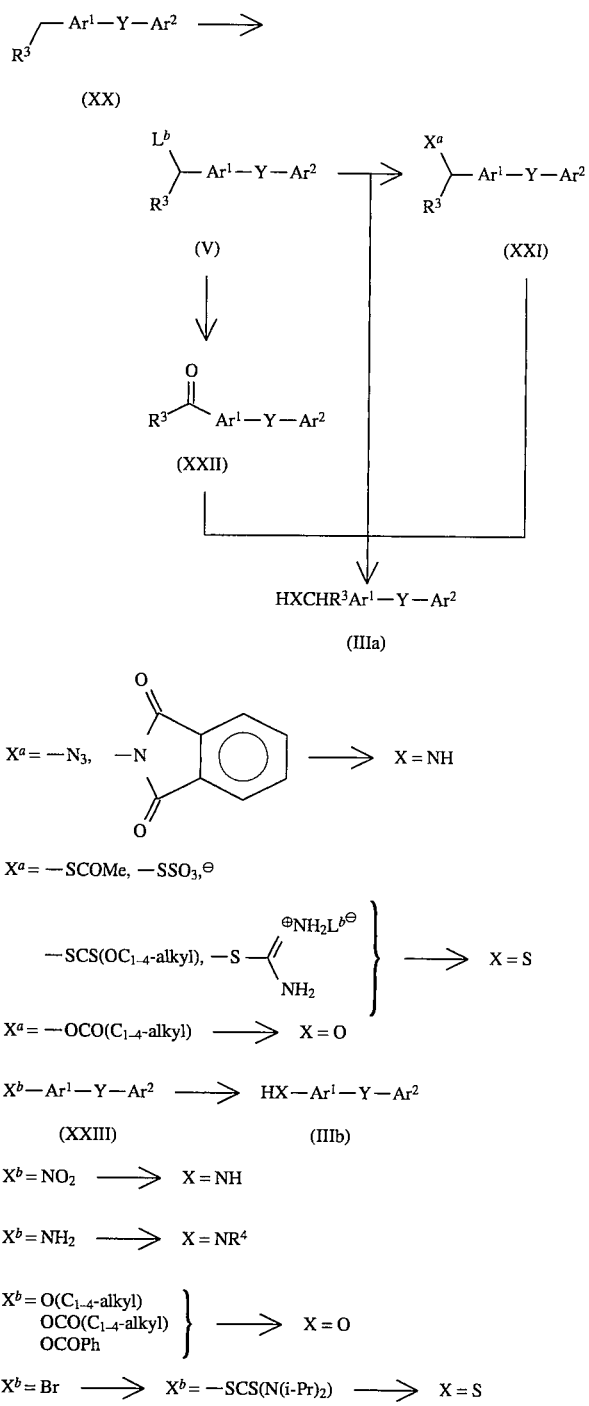

SCHEME 5

Preferred methods for the synthesis of compounds of formula III or formula V from Scheme 1 and from Scheme 4 are summarized in Scheme 5. These compounds are known or may be prepared by known methods. In particular, compounds of formula XX and of formula V ($L^b$=Br) are known, e.g. those, in which $Ar^1$ and $Ar^2$ are phenyl rings of formula (E) or formula (I) (European Patent Appl. EP 253 310; EP 291 969; EP 323 841; EP 324 377; EP 400 835; EP 400 974; EP 401 030; EP 419 048), in which $R^3$ is other than hydrogen and $Ar^1$ and $Ar^2$ are phenyl rings (European Patent Appl. EP 456 442), in which $Ar^1$ and/or $Ar^2$ are pyridinyl rings of formula (F), (G), or (J) (European Patent Appl. EP 504 888; EP 510 813; U.S. Pat. No. 5 149 699), in which $Ar^2$ is a furan or a thiophene of formula (L) (European Patent Appl. EP 510 812), in which $Ar^2$ is a pyrrol of formula (L) or formula (M) (European Patent Appl. EP 480 204, Int. Patent Appl. WO 92/11255, WO 92/15577), in which $Ar^1$ is an indole of formula (H) (European Patent Appl. EP 429 257), a benzothiophene of. formula (H) (European Patent Appl. EP 430 709), or a benzofuran of formula (H) (European Patent Appl. EP 434 249; International Patent Appl. WO 92/09600), or in which Y is a group containing an acidic substituent $R^{20}$ (International Patent Appl. WO 91/11909; European Patent Appl. EP 519 831).

Compounds of formula V, in which the leaving group $L^b$ is chloro or bromo, may be prepared by halogenation of compounds of formula XX, in particular, bromides by bromination with N-bromo succinimide in refluxing tetrachloromethane in the presence of a catalytic amount of dibenzoyl peroxide or azobis isobutyronitrile (AIBN). Compounds of formula V, in which $L^b$ is a sulfonyloxy group, are prepared from benzylalcohols III (X=O) and the corresponding aliphatic or aromatic sulfonyl chlorides by standard procedures.

Compounds of formula IIIa, the special embodiment of formula III, in which n is 1, are prepared from compounds of formula V via suitable intermediates of formula XXI, in which the group $X^a$ is a suitable precursor of the group X, or intermediates of formula XXII. For the preparation of benzylamines IIIa (X=NH) compounds of formula V are treated with an inorganic azide such as lithium or sodium azide in an inert polar solvent such as DMF, N,N-dimethyl acetamide, or DMSO, optionally by heating of the mixture. The resulting azide XXI ($X^a$=N$_3$) is reduced to the benzylamine IIIa by known methods, e.g. by catalytic hydrogenation, preferably with Pd on charcoal as catalyst, by reduction with LiAlH$_4$, or by treating with triphenylphosphine in solvents such as THF, ether, or 1,2-dimethoxyethane. In another preferred method compounds of formula V are reacted with potassium phthalamide in the above mentioned polar solvents, optionally by heating the mixture. The intermediates XXI ($X^a$=1,3-dihydro-1,3-dioxo-2H-isoindol-2-yl) are converted to benzylamines IIIa by standard procedures, preferably by heating with hydrazine in methanol or in ethanol. Secondary benzylamines IIIa (X=NR$^4$) are prepared by heating compounds of formula V with an excess of the amine R$^4$NH$_2$ in solvents such as methanol, ethanol, or THF, or by reaction of the amines with aldehydes or ketones XXII by standard conditions and subsequent reduction with sodium borohydride or sodium cyanoborohydride. The carbonyl compounds XXII may be prepared by oxidation of compounds of formula V, preferably by heating in DMSO in the presence of a base such as sodium bicarbonate or by heating with 2-nitropropane in the presence of a base such as sodium ethoxide in ethanol. Benzylalcohols of formula IIIa (X=O) may be prepared by reduction of carbonyl compounds XXII, e.g. with sodium borohydride in methanol or ethanol, or by addition of Grignard reagents R$^3$MgBr or alkyllithium reagents R$^3$Li to aldehydes XXII (R$^3$=H). In another preferred method compounds of formula V are treated with inorganic salts of lower aliphatic carboxylic acids to intermediates XXI ($X^a$=OOC(C$_{1-4}$-alkyl)), preferably with sodium or potassium acetate to acetates XXI ($X^a$=OOCMe), which are hydrolized by standard procedures, preferably with aqueous alcoholic alkali hydroxide solution or by reduction with sodium or lithium borohydride. Benzylthiols IIIa (X=S) are prepared from compounds of formula V by standard methods such as heating with alkali sulfides such as sodium sulfide, or by heating with thiourea, sodium or potassium thioacetate, sodium thiosulfate, or reaction with carbon disulfide in the presence of an alkali $C_{1-4}$-alkoxide, preferably methoxide or ethoxide, to the corresponding intermediates XXI, which are cleaved to thiols IIIa, preferably by using alkaline standard conditions.

Compounds of formula IIIb, the special embodiment of formula III, in which n is 0, may be prepared from suitable precursors XXIII by conversion of suitable groups $X^b$ to the groups XH. Thus, aromatic amines IIIb (X=NH) may be prepared by reduction of the corresponding nitro compounds XXIII ($X^b$=NO$_2$), preferably by catalytic hydrogenation of the nitro compounds, secondary aromatic amines IIIb (X=NR$^4$) by alkylation of the primary amines or by their acylation with chlorides, anhydrides, or esters of corresponding carboxylic acids and subsequent reduction of the resulting amides with reagents such as LiAlH$_4$. Phenols of formula IIIb (X=O) may be prepared by cleavage of suitable protected phenols such as esters XXIII ($X^b$=OOC($C_{1-4}$-alkyl), OOCPh), preferably acetates ($X^b$=OOCMe), or ethers XXIII ($X^b$=O($C_{1-4}$-alkyl)), preferably methylethers ($X^b$=OMe) using standard procedures. Thiophenols of formula IIIb (X=S) may be prepared by metallation of aromatic bromides of formula X XIII ($X^b$=Br) with reagents such as butyl lithium or tert. butyl lithium at low temperatures, preferably below −50° C., and trapping the aryl lithium compounds with elemental sulfur or with tetraisopropylthiuram disulfide.

Substituents $R^5$, $R^6$, $R^7$, $R^8$, $R^9$, $R^{10}$, or $R^{11}$ in fused pyrimidines of formula (A), (B), (C), or (D) may be converted to other substituents. These conversions may be carried out on compounds of formula I, II, IV, XIII, or on any other compound, which contains one of the fused heterocycles and is presented in the schemes.

A substituent $R^5$ in compounds containing a pyrazolo[1,5-a]pyrimidine of formula (A) or a substituent $R^{10}$ in compounds containing an imidazo[1,2-a]pyrimidine of formula (D), which means hydrogen and which is connected to C-3 of the heterocycle, may be converted to halo, mercapto, nitro, nitroso, $C_{1-8}$-alkylsulfonyl, $C_{1-4}$-perfluoroalkylsulfonyl, phenylsulfonyl, SO$_3$H, SO$_2$NR$^{23}$R$^{24}$, formyl, $C_{1-6}$-alkanoyl, or benzoyl by known or according to known methods: H. Dorn, H. Dilcher, Liebigs Ann. Chem. 1967, 707, 141; T. Novinson, B. Bhooshan, T. Okabe, G. R. Revankar, R. K. Robins, K. Senga, H. R. Wilson, J. Med. Chem. 1976, 19, 512; W. E. Kirkpatrick, T. Okabe, I. W. Hillyard, R. K. Robins, A. T. Dren, T. Novinson, J. Med. Chem. 1977, 20, 386; R. H. Springer, M. B. Scholten, D. E. O'Brien, T. Novinson, J. P. Miller, R. K. Robins, J. Med. Chem. 1982, 25, 235; T. Novinson, R. Hanson, M. K. Dimmitt, L. N. Simon, R. K. Robins, D. E. O'Brien, J. Med. Chem. 1974, 17, 645; T. Novinson, R. K. Robins, D. E. O'Brien, Tetrahedron Lett. 1973, 3149; Y. Rival, G. Grassy, G. Michel, Chem. Pharm. Bull. 1992, 40, 1170; T. Pyl, W. Baufeld, Liebigs Ann. Chem. 1966, 699, 112. Thus, a chlorination is preferably carried out with N-chloro succinimide or with a mineral acid chloride such as sulfuryl chloride, a bromination preferably with N-bromo succinimide or with elemental bromine, an iodination preferably with iodine monochloride in an inert solvent such as acetonitrile, dichloromethane, chloroform, tetrachloromethane, or 1,2-dichloroethane, or in acetic acid, optionally by heating under reflux in these solvents. A nitration may be carried out with concentrated or fuming nitric acid, optionally in the presence of concentrated sulfuric acid, or with any other reagent, which is common in the art for the nitration of an aromatic ring. A nitroso compound ($R^5$, $R^{10}$=nitroso) may be prepared in a similar manner using an alkali nitrite, preferably sodium nitrite, in mineral acids such as hydrochloric acid, in acetic acid, or in mixtures of both. A sulfonic acid ($R^5$, $R^{10}$=SO$_3$H) may be prepared with fuming sulfuric acid, a sulfonamide ($R^5$, $R^{10}$=SO$_2$NR$^{23}$R$^{24}$) with chlorosulfonic acid and treating of the intermediate sulfonyl chloride with an amine HNR$^{23}$R$^{24}$ using standard conditions. A formyl group ($R^5$, $R^{10}$=CHO) is preferably introduced into the heterocycle by POCl$_3$ / DMF, the substituents $R^5$, $R^{10}$=$C_{1-6}$-alkanoyl, benzoyl, $C_{1-8}$-alkylsulfonyl, or phenylsulfonyl by using chlorides of the corresponding carboxylic acids or sulfonic acids, respectively, optionally in the presence of a Lewis acid catalyst selected from aluminum chloride, zinc chloride, tin(IV) chloride, or titanium(IV) chloride. The substituent $R^5$, $R^{10}$=$C_{1-4}$-perfluoroalkylsulfonyl, in particular trifluoromethylsulfonyl, may be introduced by using the corresponding sulfonic acid anhydrides (J. B. Hendrickson, K. W. Bait, J. Org. Chem 1977, 24, 3875). Compounds, in which $R^5$ or $R^{10}$ is mercapto, may be prepared from the unsubstituted derivatives with inorganic isothiocyanates, preferably with potassium isothiocyanate, in the presence of elemental bromine in solvents such as methanol or ethanol or with other isothiocyanates such as Cu(II) isothiocyanate and subsequent hydrolysis of the intermediate by solutions of alkaline hydroxides such as sodium or potassium hydroxide in methanol, ethanol, or isopropanol. These thiols may also be prepared by heating of the corresponding compounds, in which $R^5$ or $R^{10}$ is bromo, with inorganic sulfides such as sodium sulfide in polar solvents such as DMF or N,N-dimethyl acetamide (M. R. H. Elmoghayar, M. K. A. Ibrahim, I. El-Sakka, A. H. H. Elghandour, M. H. Elnagdi, Arch. Pharm. 1983, 316, 697).

In compounds containing a pyrazolo[1,5-a]pyrimidine of formula (A) or a [1,2,4]triazolo[1,5-a]pyrimidine of formula (B), a substituent $R^5$, which is connected to C-2 of the heterocycle, or a substituent $R^7$, respectively, may be convened to other substituents. For example, a hydroxy group may be converted to a halogen, preferably to a chlorine or bromine, by heating with mineral acid halides such as POCl$_3$ or POBr$_3$ (W. Ried, K.-P. Peuchert, L. Ann. Chem. 1965, 682, 136). A substituent $R^5$ or $R^7$, which is a suitable leaving group such as halo, preferably chloro or bromo, $C_{1-6}$-alkylthio or $C_{1-6}$-alkylsulfonyl, preferably methylthio or methylsulfonyl, particularly preferred methylsulfonyl, may be substituted by other substituents $R^5$ or $R^7$. For example, these substituents may be replaced by an $C_{1-8}$-alkoxy, $C_{1-3}$-phenylalkoxy, or a phenoxy, preferably by heating the corresponding alkali alkoxides or phenolates in alcohols of the same alkyl chain or in a polar solvent such as DMF. In a similar manner an amino group NH$_2$ or NR$^{23}$R$^{24}$ may be introduced by heating with ammonia or with the corresponding amine HNR$^{23}$R$^{24}$. A nitrile, in which $R^5$ or $R^7$ means cyano, may be prepared by heating of the corresponding chlorides, bromides, or preferably methylsulfones with inorganic cyanides, preferably with sodium cyanide, potassium cyanide, or copper(I) cyanide, in polar organic solvents such as DMF (J. R. Beck, M. P. Lynch, F. L. Wright, J. Heterocyclic Chem. 1988, 25, 555; J. R. Beck, S. A. Ackmann, M. A. Staszak, F. L. Wright, J. Heterocyclic Chem. 1988, 25, 955). A primary amine $R^5$ or $R^7$=NH$_2$ may be converted to halogens selected from chlorine, bromine, or iodine, to hydrogen, $C_{1-6}$-alkylthio, or phenylthio by methods of diazotization of a primary amine, preferably by using alkyl nitrites such as isoamyl nitrite in inert organic solvents such as dichloromethane, chloroform, or THF (J. R. Beck, R. P. Gajewski, M. P. Lynch, F. L. Wright, J. Heterocyclic Chem. 1987, 24, 267).

It is obvious to those skilled in the art that other conversions of substituents $R^5$, $R^6$, $R^7$, $R^8$, $R^9$, $R^{10}$, or $R^{11}$ connected to the bicyclic heterocycle may be carried out by standard procedures, e.g. esters $COOR^{22}$ or amides $CONR^{23}R^{24}$ may be prepared from carboxylic acids; esters, amides, or nitriles may be hydrolyzed to carboxylic acids; a nitro or a nitroso group may be reduced to a primary amine, which may be converted to an amide or sulfonamide; a formyl group or an alkanoyl group may be reduced to a primary or secondary alcohol; a hydroxy, mercapto, or amino group may be alkylated to an ether, thioether, or primary or secondary amino group; a cyano group may be converted to a 5-tetrazolyl; a formyl group by addition of a Grignard or an alkyl lithium reagent to a secondary alcohol; a thioether may be oxidized to a sulfoxide, a sulfone, or to a sulfonic acid, which may be convened to a sulfonamide via its sulfonyl chloride.

The activity of the compounds of the present invention was determined by the following tests:

Ligand-Receptor Binding Assay of the Angiotensin II Type 1 Receptor

The commercially available NED-014 kit (E.I. Du Pont de Nemours (Germany). GmbH, NEN Division) is used, and the binding assay is carried out as described by S. J. Fluharty and L. P. Reagan, J. Neurochemistry 1989, 52, 1393. 200 µl of homogenized rat liver membrane suspension is incubated for 3–4 hours at room temperature with a buffered solution of 36 pM of the radioligand ($[^{125}I]$-Sar$^1$, Ile$^8$-AII, specific activity: 2200 Ci/mmol) alone and in the presence of various concentrations of the unlabeled test compound. After rinsing the membranes with wash buffer followed by vacuum filtration through a glass fiber filter the activity is determined in a scintillation counter. The affinity constant $K_i$ for binding of the compound to the receptor is determined from its $IC_{50}$ value, which is the concentration blocking the binding of isotopically labeled ligand by 50%, as described by Y. C. Cheng and W. H. Prusoff (Biochem. Pharmacol. 1973, 22, 3099).

In Vitro Test at the Isolated Rabbit Aorta

The test is carried out according to a published method (P. C. Wong, A. T. Chiu, W. A. Price, M. J. M. C. Thoolen, D. J. Carini, A. L. Johnson, R. I. Taber, P. B. M. W. M. Timmermans, J. Pharmacol. Exp. Ther. 1988, 247, 1). Male New Zealand White rabbits (2–3 kg) are anaesthetized with carbon dioxide, debleeded, and laparotomized. A piece (3 cm) of the descending thoracic aorta is removed and conserved at 4° C. in Krebs-Ringer buffer solution (NaCl, 112; KCl, 5; $CaCl_2.2H_2O$, 2.5; $KH_2PO4$, 1; $MgSO_4.7H_2O$, 1.2; $NaHCO_3$, 25; glucose, 11.5 (in millimolar concentrations)), which is bubbled with carbon dioxide. The aorta is cut into helical strips approximately 2 mm wide, which are transferred into an organ bath containing Krebs' bicarbonate solution at 37° C. continuously bubbled with carbon dioxide. The resting tension is set to 5 g, and the strips are allowed to equilibrate for 45– minutes. After this period a cumulative dose-response curve to angiotensin II (3.10$^-$10M to 1.10$^-$7M) is constructed. The bath is changed by several washing procedures until the base line is reached. 45 minutes later the angiotensin II antagonist is added in concentrations of $10^{-5}M$, $10^{-6}M$, $10^{-7}M$, etc. After incubation for 15 minutes the cumulative dose-response curve to angiotensin II is repeated in the presence of the test compound in each case. The responses are expressed as a percentage of the maximal angiotensin II response. The $pA_2$ values of the antagonists are determined from Schild plottings. They are in the range of $pA_2$=5.2–9.2 for the presented examples.

In Vivo Test in. Conscious Renal Artery.-Ligated Hypertensive Sprague-Dawley Rats Male Sprague-Dawley Rats weighing 250–300 g are randomized into a test compound-doses regime and into a control group for an appropriate vehicle control. A number of n=8 animals is used per dose and test compound. The animals are anaesthetized with hexobarbital (Evipan-Sodium, 100 mg/kg, i.p.) and prepared according to the method of J. L. Cangiano, C. Rodriguez-Sargent, and M. Martinez-Maldonado (J. Pharm. Exp. Ther. 1979, 208, 310) by ligating the left renal artery. Six days after this surgical manipulation the activity of the test compound is determined. Again the animals are anaesthetized by injection of hexobarbital (80–100 mg/kg, i.p.), and both the right jugular vein and the carotid artery are cannulated. The catheters are passed subcutaneously to the dorsal side of the neck and exteriorized. 60–90 minutes after anaesthesia the animals have recovered, and their blood pressure and their heart rate are adjusted to a constant level. After 30 minutes registration of both parameters the test compound in DMSO / PEG 10:90 is administered orally or intraveneously through the jugular vein. The blood pressure of the animals is reduced by at least 20% after intraveneous application of 10 mg/kg of a test compounds selected from the presented examples.

Thus, the compounds of the present invention are useful in human and veterinary medicine for the treatment and prophylaxis of cardiovascular and circulatory disorders such as hypertension, in particular essential, malignant, resistant, renal, renovascular, primary and secondary pulmonary hypertension, acute or chronic congestive heart failure, aortic or cardiac insufficiency, postmyocardial infarction, angina pectoris, peripheral ischemic disorders, cardiac and vascular hypertrophy, atherosclerosis, Raynauds's disease, for the treatment and prophylaxis of renal failure such as chronic renal failure, diabetic nephropathy, chronic glumerulonephritis, glumerular sclerosis and scleroderma, nephritis with proteinuria, impaired hyperuricemia, primary and secondary (pulmonary) hyperaldosteronism, for the treatment and prophylaxis of cerebrovascular, cognitive and learning disorders, and other disorders of the central nervous system (CNS) such as Alzheimer's disease. Parkinson's disease, depression, anxiety, (senile) dementia, schizophrenia, cerebral stroke or cerebral apoplexy, alcohol or drug dependency, for the treatment and prophylaxis of elevated intraocular pressure (glaucoma), and other diseases associated with the action of angiotensin II such as pulmonary diseases for example emphysia and edema of the lung or chronic bronchitis, Bartter's syndrome, gastrointestinal, bladder, or gynecological disorders. The compounds may also be used for the treatment of psoriasis, for perioperative organ protection, and for the prevention of postsurgical vascular restenosis.

The invention also includes a pharmaceutical composition comprising a pharmaceutically-acceptable diluent or carrier in association with a compound of formula I, or a pharmaceutically-acceptable salt thereof.

The compounds may be administered by various routes, for example, by the oral or rectal route, topically or parentally, for example by injection, being usually employed in the form of a pharmaceutical composition. Such compositions form pan of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc magnesium stearate and mineral oil. The compositions of the injection may, as it is well known in the art, be formulated so as to provide quick, sustained or delayed release of the active ingredient after administration to the patient. When the compositions are formulated in unit dosage form, it is preferred that each unit dosage form contains from 5 mg to 500 mg, for example, from 25 mg to 200 mg. The term 'unit dosage form' refers to physically discrete unit suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

EXAMPLE 1

5-Ethyl-7-[N-methyl-N-((2'-(tetrazol-5-yl) biphenyl-4-yl)methyl)amino]pyrazolo [1,5-a]pyrimidine Step A:

Preparation of 5-Ethylpyrazolo[1,5-a]pyrimidine-7-ol 119.9 g (1.443 mol) of 3(5)-aminopyrazole (prepared according to G. Ege, P. Arnold, Synthesis 1976, 52) and 188.3 g (1.447 mol) of methyl 3-oxo-n-valerate were dissolved in 400 ml acetic acid and heated for 70 min at a bath temperature of 145° C. After cooling to room temperature colorless crystals separated, which were removed from the mixture by suction, washed with ethanol, and dried in vacuo, m.p. 230°–235° C.

Step B:

Preparation of 7-Chloro-5-ethylpyrazolo[1,5-a]pyrimidine 16.1 g (98.7 mmol) of the compound of the previous step were mixed with 162 ml phosphorus oxytrichloride and 12 g (10.7 ml) of N,N-diethylaniline. The flask was dipped into a preheated oil bath and the mixture heated with reflux for 45 minutes. The $POCl_3$ was removed in vacuo and the remaining syrup poured on to crushed ice. After extraction for five times with dichloromethane the combined organic layers were washed with cold saturated sodium carbonate solution, dried over sodium sulfate, and evaporated in vacuo. The title compound was obtained after chromatography on silica gel with ethyl acetate / hexane 7:3 in pale yellow crystals, m.p. 66°–68° C.

Step C:

Preparation of N-(2'-Cyanobiphenyl-4-yl)methyl-N-methyl amine 62.1 g (228 mmol) 4-bromomethyl-2'-cyanobiphenyl (prepared according to D. J. Carini et al., J. Med. Chem. 1992, 34, 2525) were dissolved in 3 l THF. After addition of 1.5 l of a 40% aqueous solution of methylamine the mixture was stirred over night at room temperature, and the THF distilled off in vacuo. The remaining aqueous layer was extracted with ethyl acetate, the extract dried by stirring over night with 0.4 nm mole sieve, and evaporated in vacuo. The title compound was obtained as a viscous oil, which was pure enough according to its $^1$H-NMR spectrum for further conversions, Step D:

Preparation of 7-[N-(2'-Cyanobiphenyl-4-yl)methyl-N-methylamino]-5-ethylpyrazolo[1,5-a]pyrimidine 1.8 g (10 mmol) of the chloro compound of Step B and 2.2 g (10 mmol) of the amine of Step C were dissolved in 60 ml ethanol and heated with reflux for 4 h. After addition of 3 ml triethylamine the heating was continued for an additional hour. The mixture was diluted with water and extracted twice with dichloromethane. The combined organic layers were dried over sodium sulfate, evaporated in vacuo, and the title compound obtained as an oil after purification by column chromatography on silica gel using ethyl acetate / hexane 9:1 as eluent, Step E:

Preparation of 5-Ethyl-7-[N-methyl-N-((2'-(tetrazol-5-yl) biphenyl-4-yl)methyl)amino]pyrazolo[1,5-a]pyrimidine The compound was prepared according to a method from the patent WO 92 / 02508. 7.1 g (21.8 mmol) tributyltin chloride and 2.5 g (38.5 mmol) sodium azide were dissolved in 50 ml water. The mixture was stirred for 4 h at room temperature and extracted with 100 ml toluene. The extract was concentrated to a volume of about 30 ml and the remaining water azeotropically removed by this process. A solution of 2.0 g (5.4 mmol) of the nitrile from the previous step in 10 ml toluene was added and the whole heated with reflux for 90 h. The mixture was poured into a solution of 5.4 g sodium nitrite in 20 ml water and 20 ml 12% hydrochloric acid with ice cooling. After stirring for some minutes a solution of 3.2 g sulphamic acid in 20 ml water was added and the whole again stirred for a while. A viscous precipitate was formed, which after decantation of the solvent was washed three times with water. The title compound separated in colorless crystals after addition of THF. These were filtered, washed with THF, and dried in vacuo, m.p. 147°–150° C. (dec.)

EXAMPLE 2

5-Ethyl-7-[(2'-(tetrazol-5-yl)biphenyl-4-yl) methylamino]pyrazolo[1,5-a]pyrimidine Step A:

Preparation of 7-[(2'-Cyanobiphenyl-4-yl)methylamino]- 5-ethylpyrazolo[1,5-a]pyrimidine 5.5 g (30.3 mmol) of the chloride from Example 1, Step B and 6.3 g (30.3 mmol) of 4-aminomethyl-2'-cyanobiphenyl (prepared according to EP 459 136) were heated in 150 ml dry ethanol for 10 h. After removal of the solvent in vacuo yellow crystals formed. These were purified by suspension in acetone and dissolved, in ethyl acetate. The solution was washed with 10% sodium carbonate solution, the organic layer dried over sodium sulfate, and evaporated to dryness to give colorless crystals of the title compound, m.p. 230°–233° C.

Step B:

Preparation of 5-Ethyl-7-[(2'-(tetrazol-5-yl)biphenyl-4-yl)methylamino]pyrazolo[1,5-a]pyrimidine 3.5 g (9.9 mmol) of the nitrile of the previous step were convened to its tetrazol with an excess of in situ formed tributyltin azide by the method described in Example 1. Step E. The title compound was obtained in two crops of colorless crystals from comparable purity after crystallisation from THF, m.p. 177°–179° C.

EXAMPLE 3

3-Chloro-5-ethyl-7-[(2'-(tetrazol-5-yl)biphenyl-4-yl)methylamino]pyrazolo[1,5-a]pyrimidine Step A:

Preparation of 3,7-Dichloro-5-ethylpyrazolo[1,5-a]pyrimidine 5.5 g (30 mmol) of the chloro compound (Example 1, Step B) and 4.0 g (30 mmol) of N-chlorosuccinimide were dissolved in 150 ml chloroform, stirred for 4 h at room temperature, and finally heated for some minutes on a steam bath. The mixture was poured on to ice water, the aqueous layer extracted with dichloromethane, the combined organic layers washed twice with saturated sodium carbonate solution, dried over sodium sulfate, and evaporated in in vacuo. The title compound was obtained as an oil after chromatography on silica gel with dichloromethane.

Step B:

Preparation of 3-Chloro-7-[(2'-cyanobiphenyl-4-yl)methylamino]-5-ethylpyrazolo[1,5-a]pyrimidine 2.2 g (10.2 mmol) of the chloride from the previous step and 2.1 g (10.1 mmol) 4-aminomethyl-2'-cyanobiphenyl were heated with reflux in 30 ml t-butanol for 15 h. The solvent was removed in vacuo, and the residue dissolved in ethyl acetate. After washing with 10% sodium carbonate solution, the organic layer was dried over sodium sulfate, and evaporated in vacuo. The title compound was separated from remaining starting materials by column chromatography (silica gel, dichloromethane) and obtained in pale yellow crystals after evaporation to dryness, m.p. 152°–154° C.

Step C:

Preparation of 3-Chloro-5-ethyl-7-[(2'-(tetrazol-5-yl)biphenyl-4-yl)methylamino]pyrazolo[1,5-a]pyrimidine 3.9 g (10 mmol) of the nitrile of the previous step were converted to its tetrazol with an excess of in situ formed tributyltin azide by the method described in Example 1. Step E. The title compound was obtained from THF in colorless crystals from the crude mixture, m.p. 136°–138° C.

EXAMPLE 4

5-Ethyl-2-phenyl -7-[(2'-(tetrazol-5-yl )biphenyl -4-yl)methylamino]pyrazolo[1,5-a]pyrimidine Step A:

Preparation of 5-Ethyl-2-phenylpyrazolo[1,5-a]pyrimidine-7-ol 4.9 g (30.8 mmol) 3-amino-5-phenylpyrazole, which was prepared from 3-oxo-3-phenylpropionitrile and hydrazine (M. H. Elnagdi, M. R. H. Elmoghayar, G. E. H. Elgemeie, Synthesis 1984, 1), and 4.0 g (30.7 mmol) methyl 3-oxovalerate were heated for 70 min in 10 ml acetic acid. The title compound precipitated in colorless needles from the mixture upon cooling, which were filtered by suction, washed with water, and recrystallized from ethanol, m.p. 316°–318° C.

Step B:

Preparation of 7-Chloro-5-ethyl-2-phenylpyrazolo[1,5-a]pyrimidine 3.3 g (13.8 mmol) of the hydroxy compound from the previous step were heated in 25 ml $POCl_3$ containing 1.5 ml N,N-diethylaniline according to Example 1. Step B. The chloride was purified by column chromatography (silica gel, dichloromethane with ascending polarity by addition of up to 2% ethanol) and obtained in pale yellow crystals after evaporation to dryness, m.p. 81°–83° C.

Step C:

Preparation of 7-[(2'-Cyanobiphenyl-4-yl)methylamino]-5-ethyl-2-phenylpyrazolo[1,5-a]pyrimidine 2.6 g (10 mmol) of the chloro compound from the previous step and 2.1 g (10 mmol) of 4-aminomethyl-2'-cyanobiphenyl were heated in 30 ml dry ethanol for 10 h. The work-up procedure was described in Step B of the preceding example, and the title compound obtained as an oil after column chromatography (silica gel, dichloromethane), Step D:

Preparation of 5-Ethyl-2-phenyl-7-[(2'-(tetrazol-5-yl)biphenyl-4-yl)methylamino]pyrazolo[1,5-a]pyrimidine 2.1 g (4.9 mmol) of the nitrile from the previous step were heated with an excess of in situ formed tributyltin azide according to Example 1, Step E. The tetrazole was obtained as a white powder by crystallization from THF, m.p. 163°–165° C. (dec.)

EXAMPLE 5

5-Ethyl-3-nitro-7-[(2'-(tetrazol-5-yl)biphenyl-4-yl) methylamino]pyrazolo[1,5-a]pyrimidine Step A:

Preparation of 5-Ethyl-3-nitropyrazolo[1,5-a]pyrimidine-7-ol 6.0 g (46.8 mmol) 3(5)-amino-4-nitropyrazole (prepared according to H. Dorn, H. Dilcher, Liebigs Ann. Chem. 1967, 707, 141) and 6.1 g (46.8 mmol) methyl 3-oxo-n-valerate were heated in 20 ml acetic acid for 70 min. After cooling of the mixture to room temperature crystals precipitated, which were filtered by suction and treated with saturated sodium bicarbonate solution. The remaining crystals were filtered, and another crop of crystals precipitated from the filtrate upon acidification with hydrochloric acid Both crops were combined, washed with water, and dried in vacuo to give a pure sample of the title nitro compound in pale yellow crystals. m.p. 220°–222° C.

Step B:

Preparation of 7-Chloro-5-ethyl-3-nitropyrazolo[1,5-a]pyrimidine 7.3 g (35.1 mmol) of the hydroxy compound from the previous step were heated in 50 ml $POCl_3$ containing 3.2 ml N,N-diethylaniline according to Example 1, Step B. The title compound was purified by column chromatography (silica gel, dichloromethane) and obtained as a beige powder after evaporation to dryness, m.p. 139°–140° C.

Step C:

Preparation of 7-[(2'-Cyanobiphenyl-4-yl)methylamino]-5-ethyl-3-nitropyrazolo[1,5-a]pyrimidine 3.4 g (15.0 mmol) of the chloride from the previous step and 3.1 g (14.9 mmol) 4-aminomethyl-2'-cyanobiphenyl were heated in 75 ml dry ethanol for 10 h. Upon cooling to room temperature crystals precipitated, which were filtered by suction and dissolved in dichloromethane. The solution was washed with 10% sodium carbonate solution, dried over sodium sulfate, and evaporated to dryness in vacuo to give pale yellow crystals of the title compound, m.p. 205°–207° C.

Step D:

Preparation of 5-Ethyl-3-nitro-7-[(2'-(tetrazol-5-yl)biphenyl-4-yl)methylamino]pyrazolo[1,5-a]pyrimidine 2.8 g (7.0 mmol) of the nitrile from the previous step were heated with an excess of in situ formed tributyltin azide according to Example 1, Step E. The title tetrazole was obtained in yellow crystals from THF after the normal work-up procedure, m.p. 138°–139° C. (dec.)

EXAMPLE 6

3,5-Diethyl-7-[(2'-(tetrazol-5-yl)biphenyl-4-yl)methylamino]pyrazolo[1,5-a]pyrimidine Step A:

Preparation of 3,5-Diethylpyrazolo[1,5-a]pyrimidine-7-ol 5.0 g (45.0 mmol) 3(5)-amino-4-ethylpyrazole (prepared by the method of R. H. Springer, M. B. Scholten, D. E. O'Brien, T. Novinson, J. P. Miller, R. K. Robins, J. Med. Chem. 1982, 25, 235) and 5.85 g (45.0 mmol) methyl 3-oxo-n-valerate were heated in 14.5 ml acetic acid according to Example 1. Step A to give the title compound in colorless crystals, which were filtered by suction, washed with a small amount of acetic acid, stirred in 50 ml water, filtered again, and dried in vacuo, m.p.>310° C.

Step B:

Preparation of 7-Chloro-3,5-diethylpyrazolo[1,5-a]pyrimidine 2.2 g (11.5 mmol) of the compound from the previous step were heated in 19 ml POCl$_3$ containing 1.25 ml N,N-diethylaniline according to Example 1. Step B. After evaporation of the dichloromethane extract the crude title compound was obtained as a yellow oil, which was pure enough for the next step as detected by its $^1$H-NMR spectrum.

Step C:

Preparation of 7-[(2'-Cyanobiphenyl-4-yl)methylamino]-3,5-diethylpyrazolo[1,5-a]pyrimidine 2.4 g (11.4 mmol) of the chloride from the previous step and 2.4 g (11.5 mmol) of 4-aminomethyl-2'-cyanobiphenyl were heated with reflux in 25 ml dry ethanol for 4 h. After cooling to room temperature solid precipitates were removed from the mixture by filtration, and the filtrate was evaporated in vacuo. The residue was stirred three times with 50 ml t-butylmethylether, while it solidified. The crystals were filtered off, and the combined filtrates were evaporated in vacuo. The title compound was obtained from the residue after chromatography (silica gel, dichloromethane) and evaporation of the pure fractions to dryness as a pale yellow oil, which solidified upon standing.

Step D:

Preparation of 3,5-Diethyl-7-[(2'-(tetrazol-5-yl)biphenyl-4-yl)methylamino]pyrazolo[1,5-a]pyrimidine 1.0 g (2.6 mmol) of the nitrile from the previous step were heated with an excess of in situ formed tributyltin azide according to Example 1. Step E. The title tetrazole was obtained in pale yellow crystals after evaporation of its solution in THF in vacuo and stirring of the residue with hexane, m.p. 100°–102° C. (dec.)

EXAMPLE 7

5-Methyl-7-[(2'-(tetrazol-5-yl)biphenyl-4-yl)methylamino]pyrazolo[1,5-a]pyrimidine Step A:

Preparation of 7-[(2'-Cyanobiphenyl-4-yl)methylamino]-5-methylpyrazolo[1,5-a]pyrimidine 3.35 g (20 mmol) 7-chloro-5-methylpyrazolo[1,5-a]pyrimidine (prepared according to Y. Makisumi, Chem. Pharm. Bull. 1962, 10, 620) and 4.17 g (20 mmol) 4-aminomethyl-2'-cyanobiphenyl were heated with reflux in 40 ml dry ethanol for 4 hours. The solvent was distilled off in vacuo, and the remaining oil solidified after stirring with a mixture of 20 ml hexane and 20 ml t-butylmethylether to give a reddish powder of the pure title compound, m.p. 221°–223° C.

Step B:

Preparation of 5-Methyl-7-[(2'-(tetrazol-5-yl)biphenyl-4-yl)methylamino]pyrazolo[1,5-a]pyrimidine 6.6 g (19.4 mmol) of the nitrile from the previous step were heated with an excess of in situ formed tributyltin azide according to Example 1, Step E. After the normal work-up procedure an oil was obtained, which gave colorless crystals of the title compound by stirring with THF, m.p. 219° C. (dec.)

EXAMPLE 8

5-Butyl-7-[(2'-(tetrazol-5-yl)biphenyl-4-yl)methylamino]pyrazolo[1,5-a]pyrimidine Step A:

Preparation of 5-Butylpyrazolo[1,5-a]pyrimidine-7-ol 6.5 g (37.7 mmol) ethyl 3-oxoheptanoate (prepared according to W. Wierenga, H. I. Skulnick, J. Org. Chem. 1979, 44, 310) and 3.2 g (38.5 mmol) 3(5)-aminopyrazol were heated in 20 ml acetic acid for 70 min. The solvent was distilled off in vacuo and the residue dissolved in dichloromethane. After extraction with saturated sodium bicarbonate solution, drying over sodium sulfate, and evaporation in vacuo the title compound was obtained by crystallization from ethanol, m.p. 177°–178° C., colorless crystals Step B:

Preparation of 5-Butyl-7-chloropyrazolo[1,5-a]pyrimidine 5.0 g (26.1 mmol) of the hydroxy compound from the previous step were heated in 40 ml POCl$_3$ containing 2.8 ml N,N-diethylaniline according to Example 1. Step B, and the chloride was obtained after chromatography as a pale yellow oil.

Step C:

Preparation of 5-Butyl-7-[(2'-cyanobiphenyl-4-yl)methylamino]pyrazolo[1,5-a]pyrimidine 1.0 g (4.8 mmol) of the chloride from Step B and 1.0 g (4.8 mmol) of 4-aminomethyl-2'-cyanobiphenyl were heated in 40 ml ethanol for 5 h, and after removal of the solvent in vacuo the title compound was obtained from ethanol / hexane as a white powder, m.p. 200°–202° C.

Step D:

Preparation of 5-Butyl-7-[(2'-(tetrazol-5-yl)biphenyl-4-yl)methylamino]pyrazolo[1,5-a]pyrimidine 500 mg (1.3 mmol) of the nitrile from the previous step were heated with an excess of in situ formed tributyltin azide according to Example 1, Step E. The tetrazole was purified by chromatography (silica gel, dichloromethane containing 4% ethanol) and obtained in crystals after evaporation to dryness, m.p. 113°–120° C.

EXAMPLE 9

5-Methyl-7-[N-propyl-N-((2'-(tetrazol-5-yl)biphenyl-4-yl)methyl)amino]pyrazolo[1,5-a]pyrimidine Step A:

Preparation of 7-[N-(2'-Cyanobiphenyl-4-yl)methyl-N-propylamino]-5-methylpyrazolo[1,5-a]pyrimidine 2.5 g (10.0 mmol) of N-(2'-cyanobiphenyl-4-yl)methyl-N-propyl amine (prepared from n-propylamine and 4-bromomethyl-2'-cyanobiphenyl by the method described in EP 490 820) and 1.8 g (10.7 mmol) 7-chloro-5-methylpyrazolo[1,5-a]pyrimidine (prepared according to Y. Makisumi, Chem. Pharm. Bull. 1962, 10, 620) were heated with reflux in 20 ml dry ethanol for 4 h. The mixture was concentrated to halve of the volume in vacuo and cooled with ice, while the remaining starting amine crystallized. It was filtered with suction, and the rest of the solvent was removed. The title compound was obtained from the residue after column chromatography (silica gel, acetone / hexane 1:9 and 2:3) as a yellow oil.

Step B:

Preparation of 5-Methyl-7-[N-propyl-N-((2'-(tetrazol-5-yl)biphenyl-4-yl)methyl)amino]pyrazolo[1,5-a]pyrimidine 920 mg (2.4 mmol) of the nitrile from the previous step were heated with an excess of in situ formed tributyltin azide according to Example 1, Step E. After the normal work-up procedure the tetrazole was purified by chromatography (silica gel, dichloromethane containing 5% ethanol) and obtained as a beige powder after evaporation to dryness and stirring with hexane, m.p. 110°–112° C.

EXAMPLE 10

5-Ethyl-7-[(2'-(tetrazol-5-yl)biphenyl-4-yl)methylthio]pyrazolo[1,5-a]pyrimidine Step A:

Preparation of 5-Ethylpyrazolo[1,5-a]pyrimidine-7-thiol 5.0 g (27.5 mmol) of the chloride from Example 1, Step B and 4.2 g (55.2 mmol) thiourea were heated in 100 ml dry ethanol for 5 h. The solvent was distilled off in vacuo and the residue crystallized from ethanol / water to give the title compound in yellow crystals, m.p. 178°–180° C.

Step B:

Preparation of 7-[(2'-Cyanobiphenyl-4-yl)methylthio]-5-ethylpyrazolo[1,5-a]pyrimidine 1.7 g (9.5 mmol) of the thiol from the previous step and 2.6 g (9.5 mmol) of 4-Bromomethyl-2'-cyanobiphenyl were dissolved in 30 ml dry DMF. 250 mg (10.4 mmol) sodium hydride were carefully added and the mixture stirred at room temperature over night. After careful addition of 100 ml water the title compound precipitated in pale yellow crystals, which were recrystallized from ethanol and dried in vacuo, m.p. 153°–155° C.

Step C:

Preparation of 5-Ethyl-7-[(2'-(tetrazol-5-yl)biphenyl-4-yl)methylthio]pyrazolo[1,5-a]pyrimidine 2.5 g (6.75 mmol) of the nitrile from the previous step were heated with an excess of in situ formed tributyltin azide according to Example 1, Step E. After the normal work-up procedure the residue was recrystallized from ethanol and the title compound obtained in yellow crystals, m.p. 128°–135° C. (dec.)

EXAMPLE 11

5-Ethyl-7-[(2'-(tetrazol-5-yl)biphenyl-4-yl)amino]pyrazolo[1,5-a]pyrimidine

Step A:

Preparation of 4-Amino-2'-cyanobiphenyl 6.0 g (26.8 mmol) of 2'-cyano-4-nitrobiphenyl (prepared according to B. Sain, J. S. Sandhu, J. Org. Chem. 1990, 55, 2545) were dissolved in a mixture of 60 ml ethanol and 60 ml ethyl acetate, and the solution was filled into an autoclave. After addition of 660 mg 10% Pd on charcoal the mixture was set under an atmosphere of hydrogen (2–3 bar). The reduction was carried out at room temperature, the course of the reaction monitored by thin layer chromatography, and it had completed after 2.5 h. The catalyst was filtered and the solvent distilled off in vacuo. The title amine was obtained by crystallization from hexane as a white powder, m.p. 98°–100° C.

Step B:

Preparation of 7-[(2'-Cyanobiphenyl-4-yl)amino]-5-ethylpyrazolo[1,5-a]pyrimidine 1.4 g (7.7 mmol) of the chloride from Example 1, Step B and 1.5 g (7.7 mmol) 4-Amino-2'-cyanobiphenyl were heated in 30 ml dry ethanol for 5 h. After removal of the solvent in vacuo the nitrile was obtained in colorless crystals from ethanol, m.p. 247°–248° C.

Step C:

Preparation of 5-Ethyl-7-[(2'-(tetrazol-5-yl)biphenyl-4-yl)amino]pyrazolo[1,5-a]pyrimidine 2.2 g (6.5 mmol) of the nitrile from the previous step were heated with an excess of in situ formed tributyltin azide according to Example 1, Step E. The title compound was purified by column chromatography (silica gel, dichloromethane containing 4% to 10% ethanol), and it was obtained in yellow crystals after evaporation to dryness, m.p. 135° C.

EXAMPLE 12

4'-[(5-Ethylpyrazolo[1,5-a]pyrimidine-7-yl)amino]biphenyl-2-carboxylic acid

Step A:

Preparation of Ethyl 4'-[(5-Ethylpyrazolo[1,5-a]pyrimidine-7-yl)amino]biphenyl-2-carboxylate A solution of 800 mg (4.4 mmol) 7-chloro-5-ethylpyrazolo[1,5-a]pyrimidine (Example 1, Step B) and 1.0 g (4.1 mmol) ethyl 4'-amino-biphenyl-2-carboxylate (prepared from protected 4-bromoaniline and ethyl 2-bromobenzoate by the method of J. C. Adrian, Jr., C. S. Wilcox, J. Am. Chem. Soc. 1989, 111, 8055) in 40 ml dry ethanol was heated with reflux for 5 h. After cooling to room temperature pale yellow crystals of the title compound precipitated, which were filtered by suction and recrystallized from ethanol, m.p. 223°–225° C.

Step B:

Preparation of 4'-[(5-Ethylpyrazolo[1,5-a]pyrimidine-7-yl)amino]biphenyl-2-carboxylic acid 500 mg (1.3 mmol) of the ester from the previous step were dissolved in a mixture of 5 ml aqueous 2N sodium hydroxide solution and 20 ml ethanol and kept for 12 h with stirring at a temperature between 40° C. and 50° C. The solution was concentrated in vacuo to volume of about 10 ml and acidified with 2N hydrochloric acid. The title compound precipitated in beige crystals, which were filtered by suction after cooling with ice and recrystallized from ethanol, m.p. 251°–256° C. (dec.)

EXAMPLE 13

5-Ethyl-7-[(2'-(tetrazol-5-yl)biphenyl-4-yl) methylamino]-[1,2,4]triazolo[1,5-a]pyrimidine Step A:

Preparation of 5-Ethyl-[1,2,4]triazolo[1,5-a]pyrimidine-7-ol 33.6 g (0.4 mol) of 3-amino-1H-1,2,4-triazole and 52 g (0.4 mol) of methyl 3-oxo-n-valerate were heated in 130 ml acetic acid for 70 min. After cooling crystals precipitated, which were filtered by suction and dissolved in 1 l water. After several extractions with dichloromethane the combined organic layers were dried over sodium sulfate, and the solvent distilled off in vacuo. The title compound crystallized during the evaporation in colorless crystals, m.p. 212° C.

Step B:

Preparation of 7-Chloro-5-ethyl-[1,2,4]triazolo[1,5-a]pyrimidine 7.4 g (45.1 mmol) of the compound from the previous step were heated for 45 min in 80 ml POCl$_3$ containing 4.1 ml N,N-diethylaniline. A red crystalline material was obtained after work-up of the mixture according to Example 1, Step B. The title chloride was purified by column chromatography (silica gel, dichloromethane with ascending polarity by addition of up to 2% ethanol) and obtained in yellow crystals, m.p. 155°–157° C.

Step C:

Preparation of 7-[(2'-Cyanobiphenyl-4-yl)methylamino]-5-ethyl-[1,2,4]triazolo[1,5-a]pyrimidine 1.8 g (9.9 mmol) of the chloro compound from the previous step and 2.1 g (10.1 mmol) of 4-aminomethyl-2'-cyanobiphenyl were heated for 8 h in 30 ml t-butanol with reflux. The mixture was worked up according to Example 3, Step B, and the title compound obtained as an oil after column chromatography (silica gel, dichloromethane with ascending polarity by addition of up to 4% ethanol).

Step D:

Preparation of 5-Ethyl-7-[(2'-(tetrazol-5-yl)biphenyl-4-yl)methylamino]-[1,2,4]triazolo[1,5-a]pyrimidine 1.2 g (3.4 mmol) of the nitrile from the previous step were heated with an excess of in situ formed tributyltin azide according to Example 1, Step E. The tetrazole was obtained in colorless crystals from THF after the normal work-up procedure, m.p. 140°–142° C. (dec.)

EXAMPLE 14

5-Ethyl-7-[((4-phthalamido)phenyl)amino] pyrazolo[1,5-a]pyrimidine

Step A:

Preparation of 5-Ethyl-7-[(4-nitrophenyl)amino]pyrazolo [1,5-a]pyrimidine 4.5 g (24.8 mmol) of 7-Chloro-5-ethylpyrazolo[1,5-a] pyrimidine (Example 1, Step B) and 3.5 g (25.3 mmol) 4-nitroaniline were heated in 75 ml dry ethanol for 5 h. During evaporation of the mixture in vacuo crystals precipitated, which were dissolved in dichloromethane. The solution was washed with saturated sodium bicarbonate solution, dried over sodium sulfate, and evaporated to dryness in vacuo to give the title compound as a yellow powder, m.p. 158°–160° C.

Step B:

Preparation of 7-[(4-Aminophenyl)amino]-5-ethylpyrazolo[1,5-a]pyrimidine 3.71 g (13.1 mmol) of the nitro compound from the previous step were dissolved in a mixture of 75 ml ethanol and 75 ml acetic acid, and 500 mg of 10% Pd on charcoal were added. The mixture was filled into a hydrogenation vessel and stirred over night at room temperature under an atmosphere of hydrogen. The catalyst was filtered off, washed with ethanol and then washed with a mixture of equal volumes water and ethanol. The filtrate was evaporated in vacuo, the residue dissolved in dichloromethane, the solution extracted with saturated sodium bicarbonate solution, the organic layer dried over sodium sulfate, evaporated in vacuo, and the remaining crystals recrystallized from ethanol / hexane to give the title compound in pale yellow crystals, m.p. 153°–154° C.

Step C:

Preparation of 5-Ethyl-7-[((4-phthalamido)phenyl) amino]pyrazolo[1,5-a]pyrimidine 1.0 g (3.9 mmol) of the amine from the previous step and 580 mg (3.9 mmol) phthalic acid anhydride were dissolved in 40 ml dichloromethane and stirred for 3 days at room temperature, while a colorless precipitate was formed. In order to complete the reaction, the same amount of the anhydride, 600 mg of potassium carbonate, and a catalytic amount of triethylbenzylammonium chloride were added, and the mixture was stirred for additional 12 h at 40° C. After addition of 5 ml of water it was stirred for another 10 min, and the title compound was filtered by suction, dried in vacuo, and recrystallized from ethanol to give beige crystals, m.p. 165°–170° C.

EXAMPLE 15

2-[N-(4-(5-Ethylpyrazolo[1,5-a]pyrimidine-7-yl) aminophenyl)aminocarbonyl]benzene sulfonic acid 1.3 g (5.1 mmol) of the amine from Example 14, Step B and 940 mg (5.1 mmol) of 2-sulfobenzoic acid cyclic anhydride were dissolved in 20 ml dichloromethane. A solid material precipitated immediately from the clear solution, and the mixture was stirred at room temperature over night. The pale yellow crystals of the title compound were filtered by suction, heated with ethanol, filtered again after cooling to room temperature, and dried in vacuo, m.p.>320° C.

EXAMPLE 16

1-(4-(N-(5-Ethylpyrazolo[1,5-a]pyrimidine-7-yl) amino)benzamido)-2-(tetrazol-5-yl)benzene Hydrochloride Step A:

Preparation of 1-(4-Nitrobenzamido)-2-(tetrazol-5-yl) benzene 3.0 g (18.6 mmol) 2-(tetrazol-5-yl)aniline (prepared by heating of 2-aminobenzonitrile in the presence of sodium azide according to E. R. Wagner, J. Org. Chem. 1973, 38, 2976) and 3.2 ml pyridine were dissolved in 50 ml dichloromethane. A solution of 3.7 g (19.9 mmol) 4-nitrobenzoyl chloride in 50 ml dichloromethane was added via a dropping funnel, and the mixture was heated with reflux for 1 h. The title compound precipitated from the solution, was filtered with suction, washed with hexane, and dried in vacuo to give a yellow powder, m.p. 223–225 (dec.)

Step B:

Preparation of 1-(4-Aminobenzamido)-2-(tetrazol-5-yl)benzene 4.5 g (14.5 mmol) of the nitro compound from the previous step were dissolved in 120 ml dry THF. The solution was filled into a hydrogenation vessel, and 300 mg of 10% Pd on charcoal were added. The mixture was stirred over night at room temperature under an atmosphere of hydrogen. The catalyst was removed by filtration, and the filtrate was evaporated in vacuo to give the pure title compound as a pale yellow powder. m.p. 202°–204° C.

Step C:

Preparation of 1-(4-(N-(5-Ethylpyrazolo[1,5-a]pyrimidine-7-yl)amino)benzamido)-2-(tetrazol-5-yl)benzene Hydrochloride 1.8 g (9.9 mmol) 7-Chloro-5-ethylpyrazolo[1,5-a]pyrimidine (Example 1, Step B) and 2.7 g (9.6 mmol) of the amine from the previous step were dissolved in 50 ml dry ethanol and heated with reflux for 6 h. A precipitate was formed upon cooling, which was isolated by filtration. To remove remaining starting materials the solid was heated in a mixture of methanol and water, and the pure title compound was obtained as a pale yellow powder after filtration with suction and drying in vacuo, m.p. 300° C. (dec.)

EXAMPLE 17

6-Ethyl-7-[(2'-(tetrazol-5-yl)biphenyl-4-yl)methylamino]pyrazolo[1,5-a]pyrimidine Step A:

Preparation of 6-Ethylpyrazolo[1,5-a]pyrimidine-7-ol 2.9 g (34.9 mmol) 3(5)-aminopyrazole and 5.0 g (34.7 mmol) ethyl 2-formylbutyrate (prepared from ethyl butyrate and ethyl formate by the method of S. S. Klioze, F. P. Darmory, J. Org. Chem. 1975, 40, 1588) were dissolved in 20 ml dry ethanol and heated with reflux for 12 h. In order to complete the reaction, a solution of 800 mg (34.8 mmol) sodium in 5 ml dry ethanol was added and the mixture heated for additional 4 h. After cooling to room temperature solid precipitates were filtered off and the solution concentrated in vacuo. The residue was stirred with 150 ml water and adjusted to pH 4 with diluted hydrochloric acid. The title compound crystallized in colorless crystals, which were filtered with suction and dried in vacuo, m.p. 247°–248° C.

Step B:

Preparation of 7-Chloro-6-ethylpyrazolo[1,5-a]pyrimidine 1.13 g (6.9 mmol) of the compound from the previous step were heated in 11.5 ml $POCl_3$ containing 0.7 ml N,N-diethylaniline according to Example 1, Step B. The combined organic layers of dichloromethane were dried over sodium sulfate and evaporated in vacuo to give 1.3 g of the crude title compound as an oil, which was used for the next step without further purification.

Step C:

Preparation of 7-[(2'-Cyanobiphenyl-4-yl)methylamino]-6-ethylpyrazolo[1,5-a]pyrimidine 1.3 g (7 mmol) of the crude chloride from the previous step and 1.5 g (7.2 mmol) of 4-aminomethyl-2'-cyanobiphenyl were dissolved in 15 ml dry ethanol, heated with reflux for 4 h, and the solvent was removed in vacuo. Crystals were formed by stirring of the oily residue with hexane / t-butylmethylether, which were filtered by suction. These were suspended in water, the suspension was adjusted to pH 7 by diluted NaOH and extracted with dichloromethane. The organic layer was dried over sodium sulfate, evaporated in vacuo, and the residue gave beige crystals by stirring with hexane, m.p. 151°–153° C.

Step D:

Preparation of 6-Ethyl-7-[(2'-(tetrazol-5-yl)biphenyl-4-yl)methylamino]pyrazolo[1,5-a]pyrimidine 1.0 g (2.8 mmol) of the nitrile from the previous step were heated with an excess of in situ formed tributyltin azide according to Example 1, Step E. The tetrazol was purified by column chromatography (silica gel, dichloromethane and ascending polarity by addition of 5% ethanol) and obtained in beige crystals after stirring with hexane / t-butylmethylether from the pure fractions, m.p.101°–103° C. (dec.)

EXAMPLE 18

Ethyl 5-Ethyl-7-[(2'-(tetrazol-5-yl)biphenyl-4-yl)methylamino]pyrazolo[1,5-a]pyrimidine-3-carboxylate Step A:

Preparation of Ethyl 5-Ethylpyrazolo[1,5-a]pyrimidine-7-ol-3-carboxylate 4.7 g (30.3 mmol) of commercially available ethyl 3(5)-aminopyrazole-4-carboxylate (Aldrich) and 3.9 g (30.0 mmol) methyl 3-oxo-n-valerate were heated with reflux in 9 ml acetic acid for 2.5 h. After standing over night at room temperature crystals precipitated. 10 ml of water were added, and the precipitate was filtered with suction, washed with water, and dried in vacuo to give the title compound as a white powder, m.p. 173°–174° C.

Step B:

Preparation of Ethyl 7-Chloro-5-ethylpyrazolo[1,5-a]pyrimidine-3-carboxylate 5.9 g (25.1 mmol) of the compound from the previous step were heated in 30 ml $POCl_3$ containing 2 ml N,N-diethylaniline according to Example 1, Step B. After the normal work-up procedure the title compound was purified by column chromatography (silica gel, dichloromethane). The pure fractions were evaporated to dryness in vacuo, and the chloride was obtained in orange crystals, m.p. 115°–117° C.

Step C:

Preparation of Ethyl 7-[(2'-Cyanobiphenyl-4-yl)methylamino]pyrazolo[1,5-a]pyrimidine-3-carboxylate 1.3 g (5.1 mmol) of the chloride from the previous step and 1.0 g (4.8 mmol) 4-aminoethyl-2'-cyanobiphenyl were dissolved in 30 ml dry ethanol and heated with reflux for 10 h. After work-up of the mixture as described in Example 3, Step B the title compound was purified by column chromatography (silica gel, dichloromethane) and obtained in pale yellow crystals by crystallization from dichloromethane / ether, m.p. 148°–150° C.

Step D:

Preparation of Ethyl 5-Ethyl-7-[(2'-(tetrazol-5-yl)biphenyl-4-yl)methylamino]pyrazolo[1,5-a]pyrimidine-3-carboxylate 1.0 g (2.35 mmol) of the nitrile from the previous step were heated with an excess of in situ formed tributyltin azide according to Example 1, Step E. After normal work-up the title compound was isolated from the crude mixture by column chromatography (silica gel, dichloromethane containing 8% ethanol), and the remaining yellow oil of the pure fractions was treated with ethanol to give colorless crystals of the tetrazole, m.p. 215°–217° C. (dec.)

EXAMPLE 19

5-Ethyl-7-[(2'-(tetrazol-5-yl)biphenyl-4-yl)methylamino] pyrazolo[1,5-a]pyrimidine-3-carboxylic acid 320 mg (0.68 mmol) of the ester from the previous example were heated on a steam bath in 20 ml 2N aqueous sodium hydroxide solution for 30 min. The clear solution was cooled to room temperature and adjusted to pH 6 by diluted hydrochloric acid. The title compound precipitated from the mixture, and it was filtered by suction, washed with ice cold water, and dried in vacuo to give a white powder, m.p. 186°–188° C. (dec.)

EXAMPLE 20

7-[(2'-(Tetrazol-5-yl)biphenyl-4-yl)methylamino] pyrazolo[1,5-a]pyrimidine

Step A:

Preparation of 5-Chloro-7-[(2'-cyanobiphenyl-4-yl)methylamino]pyrazolo[1,5-a]pyrimidine 5.7 g (30.3 mmol) 5,7-dichloropyrazolo[1,5-a]pyrimidine (prepared according to T. Novinson, B. Bhooshan, T. Okabe, G. R. Revankar, R. K. Robins, K. Senga, H. R. Wilson, J. Med. Chem. 1976, 19, 512) and 6.3 g (30.25 mmol) 4-aminomethyl-2'-cyanobiphenyl were dissolved in 150 ml dry ethanol and heated with reflux for 10 h. The solvent was removed in vacuo, the residue dissolved in ethyl acetate, washed with 10% aqueous sodium carbonate solution, and dried over sodium sulfate. After evaporation in vacuo the title compound crystallized from ethyl acetate/ether in colorless crystals, m.p. 162°–163° C.
Step B:

Preparation of 7-[(2'-Cyanobiphenyl-4-yl)methylamino] pyrazolo[1,5-a]pyrimidine 1.8 g (5.0 mmol) of the chloride from the previous step were dissolved in a mixture of 75 ml ethanol and 50 ml acetic acid. The solution was filled into a hydrogenation vessel and stirred over night under an atmosphere of hydrogen after addition of 300 mg of 10% Pd on charcoal. The catalyst was removed by filtration, and the mixture was worked up as described in the preceding step. The title compound was separated from remaining starting material by column chromatography (silica gel, dichloromethane) and obtained as a colorless oil, which solidified upon standing, m.p. 170°–170° C.
Step C:

Preparation of 7-[(2'-(Tetrazol-5-yl)biphenyl-4-yl)methylamino]pyrazolo[1,5-a]pyrimidine 430 mg (1.32 mmol) of the nitrile from the previous step were heated with an excess of in situ formed tributyltin azide according to Example 1, Step E. The title compound was obtained in beige crystals after the normal work-up procedure and crystallization from THF, m.p. 150°–155° C.

EXAMPLE 21

3-Chloro-5-ethyl-7-[N-methyl-N-((2'-(tetrazol-5-yl)biphenyl-4-yl)methyl)amino]pyrazolo [1,5-a]pyrimidine Step A:

Preparation of 3-Chloro-7-[N-(2'-cyanobiphenyl-4-yl)methyl-N-methylamino]-5-ethylpyrazolo[1,5-a]pyrimidine 3.1 g (14.4 mmol) of the chloro compound (Example 3, Step A) and 3.2 g (14.4 mmol) of the amine (Example 1, Step C) were heated in 75 ml ethanol according to Example 4, Step C. The title compound was obtained as an oil after chromatography (silica gel; dichloromethane with ascending polarity by addition of up to 3% ethanol).
Step B:

Preparation of 3-Chloro-5-ethyl-7-[N-methyl-N-((2'-(tetrazol-5-yl)biphenyl-4-yl)methyl)amino]pyrazolo[1,5-a]pyrimidine 2.8 g (7.0 mmol) of the nitrile from the previous step were converted to its tetrazole with an excess of in situ formed tributyltin azide by the method described in Example 1, Step E. The title compound was isolated by crystallization from THF /ether in colorless crystals, m.p. 130°–131° C. (dec.)

EXAMPLE 22

5-Ethyl-3-propyl-7-[(2'-(tetrazol-5-yl)biphenyl-4-yl) methylamino]pyrazolo[1,5-a]pyrimidine Step A:

Preparation of 5-Ethyl-3-propylpyrazolo[1,5-a]pyrimidine-7-ol 12.5 g (100 mmol) 3(5)-amino-4-propylpyrazole (prepared from 2-formylvaleronitrile and hydrazine according to M. H. Elnagdi, M. R. H. Elmoghayar, G. E. H. Elgemeie, Synthesis 1984, 1) and 13.0 g (100 mmol) methyl 3-oxovalerate were heated with reflux for 70 min in 35 ml acetic acid. The title compound precipitated from the mixture upon cooling. It was filtered with suction, washed with water, and dried in vacuo to give colorless crystals, m.p. 279°–281° C.
Step B:

Preparation of 7-Chloro-5-ethyl-3-propylpyrazolo[1,5-a] pyrimidine 8.9 g (43.3 mmol) of the hydroxy compound from the previous step were heated in 70 ml POCl$_3$ containing 4.6 ml N,N-diethylaniline according to Example 1, Step B. After the above described work-up procedure the crude title compound was obtained as a red oil, which solidified upon standing and which was used without further purification in the reaction of the next step.
Step C:

Preparation of 7-[(2'-Cyanobiphenyl-4-yl)methylamino]-5-ethyl-3-propylpyrazolo[1,5-a]pyrimidine 2.87 g (12.8 mmol) of the crude chloride from the previous step and 2.∂g (12.8 mmol) 4-aminomethyl-2'-cyanobiphenyl were dissolved in 30 ml dry ethanol and heated with reflux for 14 h. The solvent was removed in vacuo, and the residue was stirred with hexane and with t-butylmethylether to give crystals, which were filtered by suction and suspended in water. The mixture was neutralized by diluted aqueous sodium hydroxide solution, extracted with dichloromethane, dried over sodium sulfate, and evaporated in vacuo, and the title compound was obtained as a yellow oil after column chromatography (silica gel, dichloromethane).
Step D:

Preparation of 5-Ethyl-3-propyl-7-[(2'-(tetrazol-5-yl)biphenyl-4-yl)methylamino]pyrazolo[1,5-a]pyrimidine 1.0 g (2.5 mmol) of the nitrile from the previous step were converted to its tetrazole with an excess of in situ formed tributyltin azide by the method described in Example 1, Step E. After the normal work-up procedure the title compound was isolated from the residue by column chromatography (silica gel, dichloromethane and enhanced polarity by addition of 2.5% ethanol) and obtained as a pale grey powder after stirring with hexane, m.p. 125° C. (dec.)

EXAMPLE 23

2,5-Diethyl-3-methyl-7-[(2'-(tetrazol-5-yl)biphenyl-4-yl)methylamino]pyrazolo[1,5-a]pyrimidine Step A:

Preparation of 2,5-Diethyl-3-methylpyrazolo[1,5-a]pyrimidine-7-ol 16.0 g (128 mmol) 3(5)-amino-5(3)-ethyl-4-methylpyrazole (prepared from 2-methyl-3-oxovaleronitrile and hydrazine according M. H. Elnagdi, M. R. H. Elmoghayar, G. E. H. Elgemeie, Synthesis 1984,1) and 16.7 g (128 mmol) methyl 3-oxovalerate were heated with reflux for 70 min in 40 ml acetic acid. The title compound was isolated from the mixture as described in Step A of the preceding example to give colorless crystals, m.p. 287° C.

Step B:

Preparation of 7-Chloro-2,5-diethyl-3-methylpyrazolo[1,5-a]pyrimidine 5.5 g (26.8 mmol) of the hydroxy compound from the previous step were heated in 45 ml POCl$_3$ containing 2.8 ml N,N-diethylaniline according to Example 1, Step B. After the above described work-up procedure the crude title compound was obtained as a red oil, which solidified upon standing and which was used without further purification in the reaction of the next step.

Step C:

Preparation of 7-[2'-(Cyanobiphenyl-4-yl)methylamino]-2,5-diethyl-3-methyl-pyrazolo[1,5-a]pyrimidine 2.87 g (12.8 mmol) of the crude chloride from the previous step and 2.67 g (12.8 mmol) 4-aminomethyl-2'-cyanobiphenyl were dissolved in 30 ml dry ethanol and heated with reflux for 14 h. The title compound was obtained as a yellow oil after work-up as described in Step. C of the preceding example.

Step D:

Preparation of 2,5-Diethyl-3-methyl-7-[(2'-(tetrazol-5-yl)biphenyl-4-yl)methylamino]pyrazolo[1,5-a]pyrimidine 1.7 g (4.3 mmol) of the nitrile from the previous step were converted to its tetrazole with an excess of in situ formed tributyltin azide by the method described in Example 1, Step E. The title compound was isolated from the mixture as described in Step D of the preceding example and obtained as a pale grey powder, m.p. 125° C. (dec.)

EXAMPLE 24

5-Chloro-7-[(2'-(tetrazol-5-yl)biphenyl-4-yl)methylamino]pyrazolo[1,5-a]pyrimidine 1.8 g (5.0 mmol) of the nitrile from Example 20, Step A were heated with an excess of in situ formed tributyltin azide according to Example 1, Step E. After the normal work-up procedure the title compound was purified by column chromatography (silica gel, dichloromethane containing 3% ethanol) and recrystallized from ethanol to give a pale yellow powder, m.p. 210°–211° C. (dec.)

EXAMPLE 25

2-[4-(N-(5-Ethylpyrazolo[1,5-a]pyrimidine-7-yl)amino)phenyl]-3-phenylpropionic acid Step A:

Preparation of Diethyl 2-(4-Nitrophenyl)malonate 12.0 g (74.9 mmol) diethyl malonate were dissolved in 50 ml DMSO and 8.6 g (76.6 mmol) potassium t-butoxide were added. A solution of 7.9 g (50.1 mmol) 1-chloro-4-nitrobenzene in 50 ml DMSO was added via a dropping funnel. The mixture was heated at 100° C. for 4 h and poured on to crushed ice. It was extracted twice with ethyl acetate, the combined organic layers washed with brine, dried over sodium sulfate, and evaporated in vacuo to afford a brown oil, which contained the title compound in an amount of about 75% and which was used in the reaction of the next step.

Step B:

Preparation of Diethyl 2-(4-Nitrophenyl)-2-(phenylmethyl)malonate

The remaining residue from the previous step was dissolved in 150 ml acetone, and 6.9 g (49.9 mmol) potassium carbonate and 8.55 g (50.0 mmol) benzyl bromide were added. The mixture was heated with reflux for 5 h, and after cooling to room temperature the inorganic material was filtered off. The filtrate was concentrated in vacuo, and the remaining oil was used in the next step without further purification.

Step C:

Preparation of 2-(4-Nitrophenyl)-3-phenylpropionic acid

The oil from the previous step was dissolved in a mixture of 100 ml acetic acid and 50 ml 5N hydrochloric acid and heated with reflux for 40 h. The mixture was poured on to crushed ice and extracted with toluene, and the organic layer was extracted with 2N sodium hydroxide solution. The alkaline aqueous extract was acidified with 12% hydrochloric acid, while the title compound precipitated. The solid was filtered with suction, washed with water, and dried in vacuo to give the pure compound as a yellow powder, m.p. 148°–150° C.

Step D:

Preparation of 2-(4-Aminophenyl)-3-phenylpropionic acid 6.8 g (25.5 mmol) of the nitro compound from the previous step were dissolved in a mixture of 50 ml ethanol and 50 ml acetic acid. The solution was filled into a hydrogenation vessel, 500 mg of 10% Pd on charcoal were added, and the mixture stirred over night under an atmosphere of hydrogen, while crystals of the title compound were formed. The precipitate was filtered through celite, and a first crop of the title amino acid was obtained by extraction of the remaining solids with dichloromethane and with hot ethanol and evaporation of the extracts in vacuo. Treatment of the rest of the solids with warm 2N aqueous sodium hydroxide solution and acidification of the alkaline extract with diluted hydrochloric acid gave a second crop, which was filtered with suction and washed with water. The combined crops were dried in vacuo to give the pure title compound as a beige powder, m.p. 196°–198° C.

Step E:

Preparation of 2-[4-(N-(5-Ethylpyrazolo[1,5-a]pyrimidine-7-yl)amino)phenyl]-3-phenylpropionic acid 1.8 g (9.9 mmol) of 7-chloro-5-ethylpyrazolo[1,5-a]pyrimidine (Example 1, Step B) and 2.4 g (10.2 mmol) of the amine from the previous step were heated with reflux in 30 ml dry ethanol for 10 h. The solvent was removed in vacuo, the residue dissolved in dichloromethane, and washed with saturated sodium bicarbonate solution. The organic layer was dried over sodium sulfate, evaporated in vacuo, and the remaining solid recrystallized from ethanol to give the title compound as a pale yellow powder, m.p. 195°–197° C.

EXAMPLE 26

5-Ethyl-7-[(4-((phenyl)(tetrazol-5-yl)methyl)phenyl)amino]pyrazolo[1,5-a]pyrimidine Step A:

Preparation of 7-[(4-((Cyano)(phenyl)methyl)phenyl)amino]-5ethylpyrazolo[1,5-a]pyrimidine 2.1 g (10.1 mmol) 2-(4-Aminophenyl)-2-phenylacetonitrile (prepared by catalytic hydrogenation of phenylcyanomethylenequinone oxime according to the method of R. B. Davis, D. D. Carlos, G. S. Mattingly, J. Org. Chem. 1965, 30, 2607) and 1.8 g (9.9 mmol) 7-Chloro-5-ethylpyrazolo [1,5-a]pyrimidine (Example 1, Step B) were dissolved in 50 ml dry ethanol and heated with reflux for 10 h. Solid materials, which precipitated after cooling to room temperature, were filtered, the filtrate evaporated in vacuo, the residue treated with 10% aqueous sodium carbonate solution, and extracted with dichloromethane. The organic layer was dried over sodium sulfate, and the solvent was removed in vacuo to afford the crude title compound as an oil, which was pure enough for the next step as detected by its $^1$H-NMR spectrum.

Step B:

Preparation of 5-Ethyl-7-[(4-((phenyl)(tetrazol-5-yl)methyl)phenyl)amino]pyrazolo[1,5-a]pyrimidine 2.3 g (6.5 mmol) of the nitrile from the previous step were convened to its tetrazole by heating with an excess of in situ formed tributyltin azide according to the method described in Example 1, Step E. The title compound was isolated by crystallization from THF / ether and obtained in grey crystals, m.p. 220°–222° C. (dec.)

EXAMPLE 27

7-[(3-Bromo-2-(2-(tetrazol-5-yl)phenyl)benzofuran-5-yl)methylamino]-5-ethylpyrazolo[1,5-a]pyrimidine Step A:

Preparation of 7-[(3-Bromo-2-(2-cyanophenyl)benzofuran-5-yl)methylamino]-5-ethylpyrazolo[1,5-a]pyrimidine 540 mg (1.65 mmol) 5-(aminomethyl)-3-bromo-27(2-cyanophenyl)benzofuran (prepared according to WO 92/09600) and 300 mg (1.65 mmol) 7-Chloro-5-ethylpyrazolo[1,5-a]pyrimidine (Example 1, Step B) were heated with reflux in 4 ml dry ethanol for 13 h. In order to complete the conversion of the amine 200 mg of the chloride and 0.24 ml triethylamine in 4 ml dry ethanol were added, and the mixture was heated for additional 21 h. The solvent was removed in vacuo, and the title compound isolated from the residue by chromatography (hexane / acetone 95:5 to 75:25) to give colorless crystals after evaporation to dryness, m.p. 186°–194° C.

Step B:

Preparation of 7-[(3-Bromo-2-(2-(tetrazol-5-yl)phenyl) benzofuran-5-yl)methylamino]-5-ethylpyrazolo[1,5-a]pyrimidine 380 mg (0.8 mmol) of the nitrile from the previous step were converted to its tetrazole by heating with an excess of in situ formed tributyltin azide according to the method described in Example 1, Step E. After the normal work-up procedure the tetrazole was purified by column chromatography (silica gel, dichloromethane and ascending polarity by addition of 5% ethanol), and it was obtained as a beige powder after evaporation of the pure fractions to dryness, m.p. 210° C. (dec.)

EXAMPLE 28

7-[N-((3-Bromo-2-(2-(tetrazol-5-yl)phenyl) benzofuran-5-yl)methyl)-N-methylamino]-5-ethylpyrazolo[1,5-a]pyrimidine Step A:

Preparation of N-((3-Bromo-2-(2-cyanophenyl)benzofuran-5-yl)methyl)-N-methyl amine 3.1 g (7.9 mmol) 3-Bromo-5-(bromomethyl)-2-(2-cyanophenyl)benzofuran (prepared according to EP 434 249) were dissolved in 50 ml THF, and 25 ml of a 40% aqueous solution of methylamine was added via a dropping funnel. The mixture was stirred at room temperature over night and warmed for 2 h at 40° C. The solvent was removed in vacuo, the residue stirred with water, filtrated by suction, and washed with water. The title compound was purified by column chromatography (silica gel, dichloromethane / ethanol 99:1 to 90:10) and obtained as a colorless powder after evaporation to dryness, m.p. 114° C.

Step B:

Preparation of 7-[N-((3-Bromo-2-(2-cyanophenyl)benzofuran-5-yl)-methyl)-N-methylamino]-5-ethylpyrazolo[1,5-a]pyrimidine 800 mg (2.34 mmol) of the amine from the previous step and 410 mg (2.26 mmol) of 7-Chloro-5-ethylpyrazolo[1,5-a]pyrimidine (Example 1, Step B) were heated with reflux in 8 ml dry ethanol for 14 h. Additional 100 mg of the chloride were added, and the heating was continued for 3 h. The solvent was removed in vacuo, the residue stirred with acetone, and the remaining solid filtered with suction. It was dissolved in ethyl acetate, washed successively with saturated sodium bicarbonate solution and with water, the organic layer dried over sodium sulfate, and evaporated to dryness in vacuo to give the pure title compound as a beige powder, m.p. 130°–136° C.

Step C:

Preparation of 7-[N-((3-Bromo-2-(2-(tetrazol-5-yl)phenyl)benzofuran-5-yl)methyl)-N-methylamino]-5-ethylpyrazolo[1,5-a]pyrimidine 530 mg (1.09 mmol) of the nitrile from the previous step were converted to its tetrazole by heating with an excess of in situ formed tributyltin azide according to the method described in Example 1, Step E. After the normal work-up procedure the tetrazole was purified by column chromatography (silica gel, dichloromethane and ascending polarity by addition of 8% ethanol). The title compound was obtained as a beige powder after recrystallization from acetone, m.p. 244 ° C. (dec.)

EXAMPLE 29

5-Ethyl-7-[N-methyl-N-((2-(2-(tetrazol-5-yl) phenyl)benzofuran-5-yl)methyl)amino]pyrazolo [1,5-a]pyrimidine Step A:

Preparation of N-((2-(2-Cyanophenyl)benzofuran-5-yl) methyl)-N-methyl amine 5.3 g (17.0 mmol) 5-(bromomethyl)-2-(2-cyanophenyl) benzofuran (prepared according to EP 434 249) were dissolved in 100 ml THF, and 25 ml of a 40% aqueous solution of methylamine were added via a dropping funnel. The mixture was stirred at room temperature over night. 2×15 ml of the solution of methylamine were added, and the mixture was stirred for additional 5 h in each case. The work-up and the isolation of the title compound was carried out as described in Step A of the preceding example to give a colorless powder after crystallization of the remaining oil upon stirring with t-butylmethylether, m.p. 180° C. Step Step B:

Preparation of 7-[N-((2-(2-Cyanophenyl)benzofuran-5-yl)methyl)-N-methylamino]-5-ethylpyrazolo[1,5-a]pyrimidine 750 mg (2.86 mmol) of the amine from the previous step and 500 mg (2.75 mmol) 7-Chloro-5-ethylpyrazolo[1,5-a]pyrimidine (Example 1, Step B) were heated with reflux in 7 ml dry ethanol for 7 h. 100 mg of the chloride were added, and the mixture was heated for additional 10 h. The title compound was isolated as described in Step B of the preceding example to give a beige powder, m.p. 143° C.

Step C:

Preparation of 5-Ethyl-7-[N-methyl-N-((2-(2-(tetrazol-5-yl)phenyl)benzofuran-5-yl)methyl)amino]pyrazolo[1,5-a]pyrimidine 410 mg (1.0 mmol) of the nitrile from the previous step were convened to its tetrazole by heating with an excess of in situ formed tributyltin azide according to the method described in Example 1, Step E. The title compound was obtained in colorless crystals after the normal work-up procedure, chromatographic purification (silica gel, dichloromethane with ascending polarity by addition of 0.5% to 15% ethanol), and recrystallization from acetone, m.p. 168° C. (dec.)

EXAMPLE 30

5-Ethyl-7-[(4-(2-(tetrazol-5-yl)pyrrol-1-yl)phenyl) methylamino]pyrazolo[1,5-a]pyrimidine Step A:

Preparation of 2-Cyano-1-[4-((1,3-dihydro-1,3-dioxo-2H-isoindol-2-yl)methyl)phenyl]pyrrole 17.0 g (65.1 mmol) 1-(4-(bromomethyl)phenyl)-2-cyanopyrrole (prepared according to P. R. Bovy et al., J. Med Chem. 1993, 36, 101) and 22.0 g (119 mmol) potassium phthalimide were dissolved in 2 ml dry DMF and stirred at 70° C. for 10 h. It was cooled to room temperature, and 600 ml ice-cold water were added. After extraction with ethyl acetate, the organic layer was dried over sodium sulfate, and evaporated in vacuo. The remaining oil solidified upon standing, and it was stirred with t-butylmethylether to give pale yellow crystals of the title compound, which were filtered with suction and dried in vacuo, m.p. 167°–168° C.

Step B:

Preparation of 1-(4-(Aminomethyl)phenyl)-2-cyanopyrrole 11.2 g (34.2 mmol) of the compound from the previous step were dissolved in 420 ml dry methanol, and 1.1 ml of hydrazine hydrate were added. The mixture was heated with reflux, and for two times additional 0.5 ml hydrazine hydrate were added after 1 h and 3 h. The heating was continued for another 5 h. It was cooled with ice, and crystals precipitated, which were removed by filtration. The filtrate was evaporated in vacuo, treated with 2N aqueous sodium hydroxide solution, and extracted with ethyl acetate. The organic layer was washed with water, dried over sodium sulfate, and the solvent was distilled off in vacuo. The residue was treated with t-butylmethylether to give colorless crystals, which were removed by filtration. The filtrate was concentrated, and the title compound was isolated by column chromatography (silica gel, acetone /hexane 1:2) to give a viscous yellow oil.

Step C:

Preparation of 7-[(4-(2-Cyanopyrrol-1-yl)phenyl)methylamino]-5-ethylpyrazolo[1,5-a]pyrimidine 2.3 g (11.7 mmol) of the amine from the previous step and 2.18 g (12.0 mmol) 7-Chloro-5-ethylpyrazolo[1,5-a]pyrimidine (Example 1, Step B) were heated with reflux in 27 ml dry ethanol for 4 h. The solvent was removed in vacuo, and the title compound was isolated from the residue by column chromatography (silica gel, dichloromethane/ethanol 97:3) to give a pale yellow oil.

Step D:

Preparation of 5-Ethyl-7-[(4-(2-(tetrazol-5-yl)pyrrol-1-yl)phenyl)methylamino]pyrazolo[1,5-a]pyrimidine 900 mg (2.'mmol) of the nitrile from the previous step were convened to its tetrazole by heating with an excess of in situ formed tributyltin azide according to the method described in Example 1, Step E. The title compound was isolated from the residue by column chromatography (silica gel, dichloromethane containing 3 and 5% ethanol). It was obtained in beige crystals from the pure fractions after evaporation to dryness in vacuo, m.p. 129°–130° C.

EXAMPLE 31

5-Ethyl-7-[N-methyl-N-((4-(2-(tetrazol-5-yl) pyrrol-1-yl)phenyl)methyl)amino]pyrazolo[1,5-a] pyrimidine Step A:

Preparation of 2-Cyano-1-((4-(N-methylamino)methyl)phenyl)pyrrole 7.5 g (28.7 mmol) of 1-(4-(bromomethyl)phenyl)-2-cyanopyrrole (prepared according to P. R. Bovy et al., J. Med Chem. 1993, 36, 101) were dissolved in 1=ml THF, and 90 ml of a 40% aqueous solution of methylamine were added to this solution via a dropping funnel. The mixture was stirred over night at room temperature, and the THF removed in vacuo. The residue was treated with 100 ml water, extracted with ethyl acetate, the organic layer dried over sodium sulfate, and evaporated in vacuo. The title compound was purified by column chromatography (silica gel, acetone / hexane with ascending polarity from 1:16 to 1:1). An analytical sample was obtained from acetone in colorless crystals, m.p. 198°–199° C.

Step B:

Preparation of 7-[N-((4-(2-Cyanopyrrol-1-yl)phenyl)methyl)-N-methylamino]-5-ethylpyrazolo[1,5-a]pyrimidine 2.0 g (9.5 mmol) of the amine from the previous step and 1.72 g (9.5 mmol) of 7-Chloro-5-ethylpyrazolo[1,5-a]pyrimidine (Example 1, Step B) were dissolved in 25 ml dry ethanol and heated with reflux for 4 h. The solvent was removed in vacuo, the residue treated was saturated aqueous sodium bicarbonate solution, and extracted with ethyl acetate. The organic layer was dried over sodium sulfate and evaporated in vacuo to give the pure title compound as a yellow oil.

Step C:

Preparation of 5-Ethyl-7-[N-methyl-N-((4-(2-(tetrazol-5-yl)pyrrol-1-yl)phenyl)methyl)amino]pyrazolo[1,5-a]pyrimidine 900 mg (2.53 mmol) of the nitrile from the previous step were heated with an excess of in situ formed tributyltin azide according to Example 1, Step E. After the normal work-up procedure the title compound was purified by column chromatography (silica gel, dichloromethane containing 5% ethanol) to give the title compound in beige crystals after evaporation to dryness, m.p. 115°–117° C. (dec.)

EXAMPLE 32

7-Ethyl-5-[(2'-(tetrazol-5-yl)biphenyl-4-yl) methylamino]imidazo[1,2-a]pyrimidine Step A:

Preparation of 7-Ethylimidazo[1,2-a]pyrimidine-5-ol 20.0 g (151.4 mmol) commercially available (Aldrich) 2-aminoimidazole sulfate and 19.7 g (151.4 mmol) methyl 3-oxo-n-valerate were heated with reflux in 27 ml acetic acid for 7 h. After cooling to room temperature remaining solids were removed by filtration, and the filtrate was diluted with water, neutralized with sodium hydroxide, and extracted with dichloromethane. The organic layer was dried over sodium sulfate, evaporated in vacuo, while the title compound crystallized in colorless crystals, which were filtered with suction, washed with hexane, and dried in vacuo, m.p. 93°–94° C.

Step B:

Preparation of 5-[(2'-Cyanobiphenyl-4-yl)methylamino]-7-ethylimidazo [1,2-a]pyrimidine 1.68 g (10.3 mmol) of the compound from the previous step, 2.13 g (10.2 mmol) 4-aminomethyl-2'-cyanobiphenyl, and 2.13 g (10.3 mmol) dicyclohexyl carbodiimide (DCC) were dissolved in 80 ml dry dioxane and stirred over night at 50° C. Another 1 g (4.8 mmol) of DCC was added, and the reaction was continued for 8 h at 50° C. and over night at 80 ° C. The mixture was cooled to room temperature, solids were filtered, and the solvent was distilled off in vacuo. The title compound was isolated from the residue by column chromatography (silica gel, dichloromethane/ethanol 20:1) and obtained in colorless crystals after stirring with t-butylmethylether, m.p. 99°–100° C.

Step C:

Preparation of 7-Ethyl-5-[(2'-(tetrazol-5-yl)biphenyl-4-yl)methylamino]imidazo[1,2-a]pyrimidine 1.3 g (3.7 mmol) of the nitrile from the previous step were converted to its tetrazole by heating with an excess of in situ formed tributyltin azide according to the method described in Example 1, Step E. After work-up as described above the solution in THF was concentrated in vacuo, and the title compound crystallized upon treatment with hexane. It was purified by column chromatography (silica gel, dichloromethane with ascending polarity by addition of 1% to 3% ethanol), and obtained from the pure fractions in pale yellow crystals, m.p. 92°–93° C.

EXAMPLE 33

(S)-2-[(4-(5-Ethylpyrazolo[1,5-a]pyrimidine-7-yl)amino)benzamido]-3-phenylpropanoic acid Step A:

Preparation of Methyl (S)-2-(4-Nitrobenzamido)-3-phenylpropanoate 2.0 g (9.3 mmol) L-phenylalanine methylester hydrochloride and 1.73 g (9.3 mmol) 4-nitrobenzoyl chloride were dissolved in a mixture of 10 ml dichloromethane and 5 ml pyridine and stirred over night at room temperature. The mixture was evaporated in vacuo, while a colorless solid precipitated, which was filtered by suction, recrystallized from ethanol, washed with diisopropylether, and dried in vacuo to give the title compound in colorless needles, m.p. 115°–116° C.

Step B:

Preparation of Methyl (S)-2-(4-Aminobenzamido)-3-phenylpropanoate 2.4 g (7.3 mmol) of the nitro compound from the previous step were dissolved in 30 ml dry methanol, and 300 mg of 10% Pd on charcoal were added. The mixture was filled into a hydrogenation vessel and stirred for 18 h at room temperature under an atmosphere of hydrogen. The catalyst was filtered off and washed with ethanol. After removal of the solvent in vacuo the remaining solid was recrystallized from ethanol to give the title compound in colorless crystals, m.p. 145°–146° C.

Step C:

Preparation of Methyl (S)-2-[(4-(5-Ethylpyrazolo[1,5-a]pyrimidine-7-yl)amino)benzamido]-3-phenylpropanoate 1.8 g (6.0 mmol) of the amine from the previous step and 1.1 g (6.0 mmol) of 7-chloro-5-ethylpyrazolo[1,5-a]pyrimidine (Example 1, Step B) were dissolved in 20 ml dry ethanol and heated with reflux for 5 h. The solvent was removed in vacuo, and the title compound obtained from the residue after chromatography (silica gel, ethyl acetate / hexane 4:1) and evaporation of the pure fractions to dryness in colorless crystals, m.p. 207°–209° C.

Step D:

Preparation of (S)-2-[(4-(5-Ethylpyrazolo[1,5-a]pyrimidine-7-yl)amino)benzamido]-3-phenylpropanoic acid 1.0 g (2.25 mmol) of the ester from the previous step was stirred at room temperature for 4 h in 20 ml aqueous 2N sodium hydroxide solution. The mixture was acidified to pH 2 with diluted hydrochloric acid and concentrated to halve of the volume in vacuo. The formed precipitate was filtered by suction, recrystallized from methanol, washed with diisopropylether, and dried in vacuo to give the title compound in colorless crystals, m.p. 227°–232° C.

EXAMPLE 34

Ethyl 2-[N-(5-Ethylpyrazolo[1,5-a]pyrimidine-7-yl)-N-((2'-(tetrazol-5-yl)biphenyl-4-yl)methyl)amino]acetate Step A:

Preparation of Ethyl 2-[N-(5-Ethylpyrazolo[1,5-a]pyrimidine-7-yl)amino]acetate 1.8 g (9.9 mmol) 7-Chloro-5-ethylpyrazolo[1,5-a]pyrimidine (Example 1, Step B) and 1.4 g (10.0 mmol) ethyl 2-aminoacetate hydrochloride were dissolved in 50 ml dry ethanol. 500 mg (4.7 mmol) sodium carbonate were added, and the mixture was heated with reflux for 2 h. The inorganic material was filtered off, the residue treated with saturated aqueous sodium bicarbonate solution, and extracted with ethyl acetate. The organic layer was dried over sodium sulfate, and evaporated in vacuo to give the crude title compound as an oil, which was pure enough according to its 1H-NMR spectrum and was used for the reaction of the next step without further purification.

Step B:

Preparation of Ethyl 2-[N-(5-Ethylpyrazolo[1,5-a]pyrimidine-7-yl)-N-((2'-(N-triphenylmethyl-tetrazol-5-yl)biphenyl-4-yl)methyl)amino]acetate 2.1 g (8.5 mmol) of the crude ester from the previous step were dissolved in 40 ml dry THF, and the solution was poured on to 200 mg (8.3 mmol) sodium hydride. The mixture was kept with stirring at 75° C. for 1 h, 4.7 g (8.4 mmol) 4-(bromomethyl)-2'-(N-triphenylmethyl-tetrazol-5-yl)biphenyl were added, and the heating was continued for 2 h. The mixture was poured on to crushed ice, extracted with ethyl acetate, the organic layer dried over sodium sulfate, and evaporated in vacuo. The title compound was isolated by column chromatography (silica gel, dichloromethane / ethanol 98:2) and obtained as an oil.

Step C:

Preparation of Ethyl 2-[N-(5-Ethylpyrazolo[1,5-a]pyrimidine-7-yl)-N-((2'-(tetrazol-5-yl)biphenyl-4-yl)methyl)amino]acetate 340 mg (0.47 mmol) of the protected tetrazole from the previous step were dissolved in 4 ml ethanol containing 0.25 ml concentrated aqueous hydrochloric acid, and the mixture was stirred at room temperature for 90 minutes. The alcohol was removed in vacuo, the residue treated with water, neutralized by addition of sodium acetate, and extracted with ethyl acetate. The organic layer was dried over sodium sulfate, evaporated in vacuo, and the title compound was obtained as a colorless oil after column chromatography (silica gel, dichlormethane/ethanol 96:4).

EXAMPLE 35

2-[N-(5-Ethylpyrazolo[1,5-a]pyrimidine-7-yl)-N-((2'-(tetrazol-5-yl)biphenyl-4-yl)methyl)amino]acetic acid 900 mg (12.4 mmol) of the protected tetrazole from Step B of the previous example were heated with a mixture of 25 ml aqueous 2N sodium hydroxide solution and 10 ml ethanol on a steam bath for 2 h, while it became a clear solution. It was cooled to room temperature, brought to pH 4 with diluted aqueous hydrochloric acid, and extracted with ethyl acetate. The organic layer was dried over sodium sulfate, evaporated in vacuo, and the title acid was purified by column chromatography (silica gel, dichloromethane / ethanol 9:1). It was obtained in colorless crystals after evaporation to dryness, m.p. 224°–225° C. (dec.)

EXAMPLE 36

7-[(3-Bromo-2-(2-(tetrazol-5-yl)phenyl)benzofuran-5-yl)methylamino]-5methylpyrazolo[1,5-a]pyrimidine Step A:

Preparation of 7-[(3-Bromo-2-(2-cyanophenyl)benzofuran-5-yl)methylamino]-5-methylpyrazolo[1,5-a]pyrimidine A solution of 1.7 g (10.1 mmol) 7-chloro-5-methylpyrazolo[1,5-a]pyrimidine (prepared according to Y. Makisumi, Chem. Pharm. Bull. 1962, 10, 620) and 3.27 g (10.0 mmol) 5-(aminomethyl)-3-bromo-2-(2-cyanophenyl)benzofuran (prepared according to WO 92/09600) in 50 ml dry ethanol was heated with reflux for 5 h. The title compound precipitated upon cooling to room temperature, was filtered with suction, and recrystallized from ethanol to give colorless crystals. yield: 3.5 g (76%), m.p. 210°–215° C.

Step B:

Preparation of 7-[(3-Bromo-2-(2-(tetrazol-5-yl)phenyl)benzofuran-5-yl)methylamino]-5-methylpyrazolo[1,5-a]pyrimidine 1.8 g (3.9 mmol) of the nitrile from the previous step were heated with an excess of in situ formed tributyltin azide according to Example 1, Step E. The title compound was obtained as a colorless powder after the normal work-up procedure, stirring with THF, and recrystallization from ethanol. yield: 1.8 g (91%), m.p.>250° C.

We claim:

1. A compound of the formula

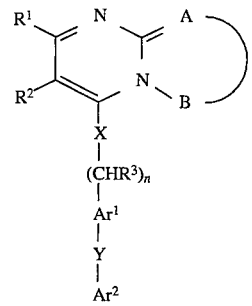

in which $R^1$ is either $R^{1a}$ selected from
- a) hydrogen,
- b) $C_{1-8}$-alkyl, $C_{3-8}$-cycloalkyl, $C_{4-8}$-cycloalkylalkyl, or $C_{4-8}$-alkylcycloalkyl, which optionally are substituted by one or more fluoro or chloro substituents, or by a single hydroxy, $C_{1-4}$-alkoxy, or $C_{1-4}$-alkylthio,
- c) phenyl or phenyl-$C_{1-3}$-alkyl,
- d) $C_{2-8}$-alkenyl, $C_{3-8}$-cycloalkenyl, or $C_{2-8}$-alkynyl, which optionally are substituted by phenyl, or $R^{1b}$ selected from
- a) $C_{1-6}$-alkylthio, $C_{3-6}$-cycloalkylthio, $C_{1-6}$-alkoxy, $C_{3-6}$-cycloalkoxy, mono-$C_{1-6}$-alkylamino, or mono-$C_{3-6}$-cycloalkylamino, in which an alkyl group optionally is substituted by phenyl or by one or more fluoro substituents,
- b) phenylthio or phenoxy,
- c) di-$C_{1-4}$-alkylamino, in which the alkyl groups are the same or different or together form a polymethylene ring with three, four, five, or six carbon atoms, which optionally are interrupted by an oxygen atom and optionally is substituted by one or more fluoro substituents,
- d) mono-phenylamino or mono-$C_{1-4}$-alkyl-monophenylamino, in which the alkyl groups optionally are substituted by one or more fluoro substituents,
- e) halo, $R^2$ is
- a) hydrogen,
- b) $C_{1-8}$-alkyl, which optionally is substituted by one or more fluoro substituents,
- c) phenyl, or $R^1$ and $R^2$ together form a polymethylene chain containing three, four or five carbon atoms, which optionally is interrupted by an oxygen or sulfur atom, $R^3$ is hydrogen or $C_{1-4}$-alkyl, and n is 0 or 1, X is O, S, or $NR^4$, and $R^4$ is
- a) hydrogen,
- b) $C_{1-8}$-alkyl, $C_{3-8}$-cycloalkyl, $C_{4-8}$-cycloalkylalkyl, or $C_{4-8}$-alkylcycloalkyl, which optionally may be substituted by phenyl or by one or more fluoro substituents,
- c) phenyl,
- d) $(CH_2)_m COOR^{22}$,
- e) $(CH_2)_m CONR^{23}R^{24}$,
- f) $(CH_2)_m COOP^{16}$, in which $P^1$ is a carboxy-protecting group,
- g) $(CH_2)_m CN$,
- h) $(CH_2)_m$(5-tetrazolyl), and m is 1 or 2 in groups d), e), f), g) or h), =A - B - together with the pyrimidine ring forms, a [1,2,4]triazolo[1,5-a]pyrimidine of formula (B),

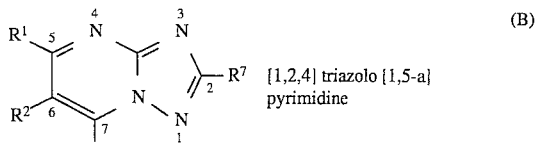

in which

R⁷ is
- a) hydrogen,
- b) $C_{1-8}$-alkyl, $C_{3-8}$-cycloalkyl, $C_{4-8}$-cycloalkylalkyl, or $C_{4-8}$-alkylcycloalkyl, which optionally are substituted by one or more fluoro or chloro substituents,
- c) phenyl-$C_{1-3}$-alkyl,
- d) hydroxy, $C_{1-6}$-alkoxy, $C_{3-6}$-cycloalkoxy, $C_{1-3}$-phenylalkoxy, or phenoxy, in which the alkyl and cycloalkyl groups optionally are substituted by one or more fluorine atoms,
- e) halo,
- f) mercapto,
- g) $C_{1-6}$-alkylthio, $C_{1-6}$-alkylsulfinyl, $C_{1-6}$-alkylsulfonyl, $C_{3-6}$-cycloalkylthio, $C_{3-6}$-cycloalkylsulfinyl, or $C_{3-6}$-cycloalkylsulfonyl, which optionally are substituted by one or more fluorine atoms,
- h) phenylthio, phenylsulfinyl, phenylsulfonyl, phenyl-$C_{1-3}$-alkylthio, phenyl-$C_{1-3}$-alkylsulfinyl, or phenyl-$C_{1-3}$-sulfonyl,
- i) phenyl,
- j) cyano,
- k) $COOR^{22}$,
- l) $CONR^{23}R^{24}$,
- m) 5-tetrazolyl,
- n) $COOP^1$, in which $P^1$ is a carboxy-protecting group,
- o) $SO_3H$,
- p) $SO_2NR^{23}R^{24}$,
- r) $NR^{23}R^{24}$,
- s) $C_{1-6}$-alkanoyl or 1-hydroxy-$C_{1-6}$-alkyl, which optionally are substituted by one or more fluorine atoms,
- t) benzoyl or phenylhydroxymethyl,
- u) NH($C_{1-6}$-alkanoyl) or NH($C_{1-6}$-alkylsulfonyl), in which the alkyl groups optionally are substituted by one or more fluorine atoms,
- v) NH(benzoyl) or NH(benzenesulfonyl), Ar¹ is a group selected from
a) 1,4-phenylene of formula (E),

b) 1,4-substituted pyridine of formula (F) or formula (G),

or c) benzofuran, benzothiophene, or indole of formula (H),

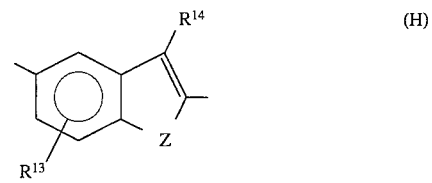

in which the group Z is O, S, or $NR^{12}$, and $R^{12}$ is hydrogen or $C_{1-4}$-alkyl, and in each of the groups Ar¹ the substituent R¹³ is
- a) hydrogen,
- b) halo,
- c) $C_{1-4}$-alkyl,
- d) $C_{1-4}$-alkoxy,
- e) trifluoromethyl,
- f) nitro, R¹⁴ is
- a) hydrogen,
- b) $C_{1-6}$-alkyl, $C_{3-6}$-cycloalkyl, $C_{4-6}$-cycloalkylalkyl, or $C_{4-6}$-alkylcycloalkyl, which optionally are substituted by one or more fluoro or chloro substituents,
- c) $C_{2-6}$-alkenyl or $C_{3-6}$-cycloalkenyl,
- d) halo,
- e) cyano,
- f) nitro,
- g) $C_{1-6}$-alkanoyl, in which the alkyl group optionally is substituted by one or more fluorine atoms,
- h) $C_{1-6}$-alkoxy,
- i) $COOR^{22}$,
- j) $CONR^{23}R^{24}$, Ar² is a group selected from
a) phenyl of formula (I),

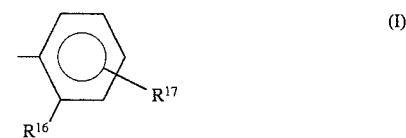

b) pyridine of formula (J),

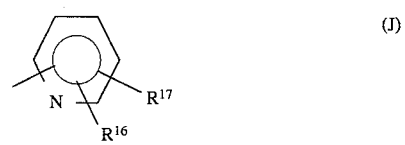

c) 1-pyrrolyl of formula (K),

or d) a five-membered heterocycle of formula (L),

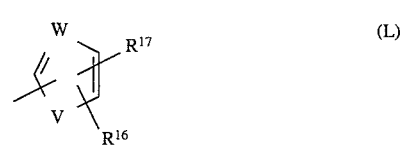

in which the group V is O, S, SO, $SO_2$, or $NR^{15}$, the group W is CH or N, and $R^{15}$ is hydrogen or $C_{1-4}$-alkyl, with the proviso that in groups Ar² of formula (J) and (L) the substituent $R^{16}$ and the group Y are in ortho positions, and in each of the groups $Ar^2$ the substituent $R^{16}$ is hydrogen, an acidic substituent, the group $COOP^1$ in which $P^1$ is a carboxy-protecting group or a group selected from
 a) cyano,
 b) a protected 5-tetrazolyl of formula (M)

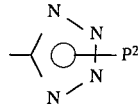

(M)

in which the group $P^2$ is a protecting group,
 c) $COO(C_{1-4}$-alkyl),
 d) nitro,
 e) amino,
 f) mercapto,
 g) $SO_2Cl$,
 h) $SO_2(OC_{1-4}$-alkyl),
 i) $PO(OC_{1-4}$-alkyl)$_2$, $R^{17}$ has independently the same meaning as $R^{13}$, $R^{18}$ and $R^{19}$ are independently selected from
 a) hydrogen,
 b) $C_{1-6}$-alkyl, $C_{3-6}$-cycloalkyl, $C_{4-6}$-cycloalkylalkyl, or $C_{4-6}$-alkylcycloalkyl, which optionally are substituted by one or more fluoro or chloro substituents,
 c) $C_{2-6}$-alkenyl or $C_{3-6}$-cycloalkenyl,
 d) halo,
 e) nitro,
 f) cyano,
 g) $C_{1-4}$-alkylthio, Y is a group selected from
 a) a direct bond, $CHR^{20}$, $CHR^{20}CH_2$, $OCHR^{20}$, $OCHR^{20}CH_2$, $SCHR^{20}$ $SCHR^{20}CH_2$, $NR_{21}CHR^{20}$, $NR^{21}CHR_{20}CH_2$, $CH_2CHR^{20}$, $CH_2CHR^{20}CH_2$,
 b) O, S, $SO_2$, $NR^{21}$, CO, CONH, NHCO, $CH_2O$, $CH_2S$, $CH_2NR^{21}$, with the proviso that when Y is (b) $Ar^1$ is 1,4-phenylene of formula (E) and $Ar^2$ is phenyl of formula (I), $R^{20}$ is hydrogen or
 a) COOH,
 b) $COOP^1$, in which $P^1$ is a carboxy-protecting group,
 d) 5-tetrazolyl,
 e) cyano,
 f) a protected 5-tetrazolyl of formula (M), with the proviso that one of the substituents $R^{16}$ and $R^{20}$ is hydrogen and the other is a substituent other than hydrogen, $R^{21}$ and $R^{22}$ are independently selected from hydrogen or $C_{1-6}$-alkyl, and $R^{23}$ and $R^{24}$ are independently selected from hydrogen or $C_{1-4}$-alkyl, or together may form a polymethylene chain containing three, four or five carbon atoms, which optionally are interrupted by an oxygen atom; the phenyl group of $R^{1a}c$), $R^{1b}b$), $R^{1b}d$), $R^2c$), $R^4c$), $R^7d$), $R^7h$), $R^7i$), $R^7t$), $R^7v$), being unsubstituted or substituted by at least one member selected from the group consisting of halo, $C_{1-4}$-alkoxy, $C_{1-4}$-alkylthio, $C_{1-4}$-alkylsulfinyl, $C_{1-4}$-alkylsulfonyl, cyano, nitro, trifluoromethyl or hydroxy, or a pharmaceutically acceptable salt thereof.

2. A compound according to claim 1, in which $R^{16}$ is an acidic substituent or a group $COOP^1$, and $R^{20}$ is COOH, 5-tetrazolyl or a group $COOP^1$.

3. A compound according to claim 2, in which $R^1$ is hydrogen, $C_{1-6}$ alkyl or $C_{3-6}$ cycloalkyl.

4. A compound according to claim 3, in which $R^1$ is Me or Et.

5. A compound according to claim 4, in which $R^2$ is hydrogen.

6. A compound according to claim 5, in which —X—$(CHR^3)$n— is [—$NHCH_2$—, $NR^4CH_2$—, —NH—, or —$SCH_2$—.

7. A compound according to claim 5, in which —X—$(CHR^3)_n$ is —$NR^4CH_2$— and $R^4$ is H, Me or $CH_2COOH$.

8. A compound according to claim 2, in which $Ar^2$ is phenyl, pyrrol-1-yl or 3-thienyl.

9. A pharmaceutical formulation comprising a compound according to claim 2, or a pharmaceutically-acceptable salt thereof, together with a pharmaceutically-acceptable diluent or carrier therefor.

10. A method of treating a cardiovascular or circulatory disorder which comprises administering an effective amount of a compound according to claim 2, or a pharmaceutically-acceptable salt thereof.

* * * * *

UNITED STATES PATENT AND TRADEMARK OFFICE
CERTIFICATE OF CORRECTION

PATENT NO. : 5,602,137
DATED : February 11, 1997
INVENTOR(S) : Ruhter, et al.

It is certified that error appears in the above-indentified patent and that said Letters Patent is hereby corrected as shown below:

Col. 64, line 62  Delete " $(CH_2)_m COOP^{16}$ " and substitute -- $(CH_2)_m COOP^1$ --

Col. 67, lines 35-36  Delete " $NR_{21}CHR^{20}$ " and substitute -- $NR^{21}CHR^{20}$ --; delete " $NR^{21}CHR_{20}CH_2$ " and substitute $NR^{21}CHR^{20}CH_2$ --.

Signed and Sealed this

Fifteenth Day of July, 1997

Attest:

BRUCE LEHMAN

*Attesting Officer*    *Commissioner of Patents and Trademarks*